United States Patent
Mahnon

(10) Patent No.: US 7,718,070 B2
(45) Date of Patent: May 18, 2010

(54) METHOD OF OBTAINING AN ORGANIC SALT OR ACID FROM AN AQUEOUS SUGAR STREAM

(75) Inventor: Daphne Mahnon, Ottawa (CA)

(73) Assignee: Iogen Energy Corporation, Ontario (CA)

( * ) Notice: Subject to any disclaimer, the term of this patent is extended or adjusted under 35 U.S.C. 154(b) by 277 days.

(21) Appl. No.: 11/774,113

(22) Filed: Jul. 6, 2007

(65) Prior Publication Data

US 2008/0041366 A1 Feb. 21, 2008

Related U.S. Application Data

(60) Provisional application No. 60/822,783, filed on Aug. 18, 2006.

(51) Int. Cl.
| | |
|---|---|
| *B01J 49/00* | (2006.01) |
| *C02F 1/42* | (2006.01) |
| *B01D 15/04* | (2006.01) |
| *B01D 15/00* | (2006.01) |
| *C13J 1/06* | (2006.01) |
| *C13J 1/02* | (2006.01) |
| *C13D 3/16* | (2006.01) |

(52) U.S. Cl. ............... 210/670; 210/638; 210/660; 210/661; 210/673; 210/674; 127/46.2; 127/46.3; 127/50; 127/51

(58) Field of Classification Search ............ 210/638, 210/660, 661, 670, 673, 674; 127/43, 46.2, 127/46.3, 50, 51
See application file for complete search history.

(56) References Cited

U.S. PATENT DOCUMENTS 4,102,705 A 7/1978 Pfeiffer et al.

(Continued)

FOREIGN PATENT DOCUMENTS

CA 2 479 248 9/2003

(Continued)

OTHER PUBLICATIONS

Wooley et al. A Nine-Zone Simulating Moving Bed for the Recovery of Gulcose and Xylose from Biomass Hydrolyzate. Ind. Eng. Chem. Res. 1998, 37, p. 3699-3709.*

(Continued)

*Primary Examiner*—Karl E Group
*Assistant Examiner*—Noah S Wiese
(74) *Attorney, Agent, or Firm*—Fitzpatrick, Cella, Harper & Scinto

(57) ABSTRACT

A process for obtaining one or more than one salt of an organic acid(s), or organic acid(s), from an aqueous sugar stream comprising one or more than one mineral acid and the organic acid(s) is provided. The process comprises introducing the aqueous sugar stream to a separation system comprising one or more beds of anion exchange resin and obtaining a stream therefrom comprising the sugar. The one or more beds of anion exchange resin are then regenerated in one or more stages to produce at least one product stream comprising the organic acid, a salt of the organic acid, or a combination thereof, and a separate outlet stream comprising the mineral acid, a salt of the mineral acid, or a combination thereof. The product stream is then recovered. The separation may be conducted with two separation units, or using a single anion exchange unit.

47 Claims, 11 Drawing Sheets

U.S. PATENT DOCUMENTS

| | | | |
|---|---|---|---|
| 4,237,110 A * | 12/1980 | Forster et al. | 423/488 |
| 4,461,648 A | 7/1984 | Foody et al. | |
| 4,818,409 A | 4/1989 | Puetter et al. | |
| 4,851,573 A | 7/1989 | Kulprathipangja et al. | |
| 4,968,353 A * | 11/1990 | Kawasaki et al. | 127/46.2 |
| 5,175,357 A * | 12/1992 | Van Brunt | 562/513 |
| 5,434,255 A * | 7/1995 | Katayama et al. | 536/117 |
| 5,789,210 A | 8/1998 | Ho et al. | |
| 6,419,828 B1 * | 7/2002 | Russo, Jr. | 210/635 |
| 6,451,123 B1 | 9/2002 | Saska et al. | |
| 2004/0231661 A1 * | 11/2004 | Griffin et al. | 127/1 |
| 2005/0244934 A1 * | 11/2005 | Foody et al. | 435/101 |

FOREIGN PATENT DOCUMENTS

| | | |
|---|---|---|
| EP | 0 106 466 | 4/1984 |
| JP | 1-127049 | 5/1989 |
| WO | WO 03/095627 | 11/2003 |
| WO | WO 2006/007691 | 1/2006 |

OTHER PUBLICATIONS

Anderson, et al., "Sulfate-Bisulfate Equilibrium on Anion Exchange Resins", Industrial and Engineering Chemistry, vol. 47, No. 8 (1955) 1620-23.

Wooley, et al., "Lignocellulosic Biomass to Ethanol Process Design and Economics Utilizing . . . ", NREL (National Renewable Energy Laboratory), (1999) 16-17.

Wooley, et al., "A Nine-Zone Simulating Moving Bed for the Recovery of Glucose and Xylose from Biomass Hydrolyzate", Ind. Eng. Chem. Res., vol. 37 (1998), 3699-709.

Barrier, et al., "Acid hydrolisis with corn stover at TVA's experimental Plant" (1985).

Barrier, et al., "Integrated Fuel Alcohol Production Systems for Agriculture Feedstockss, Phase III", Quarterly Technical Report for the period Apr.-Jun. 1985.

* cited by examiner

METHOD OF OBTAINING AN ORGANIC SALT OR ACID FROM AN AQUEOUS SUGAR STREAM

CROSS REFERENCE TO RELATED APPLICATIONS

This application claims priority to, and the benefit of, U.S. Provisional Patent Application Ser. No. 60/822,783, filed Aug. 18, 2006, which is hereby incorporated by reference in its entirety.

BACKGROUND OF THE INVENTION

1. Field of the Invention

The present invention provides a process for obtaining one or more than one organic salt or organic acid from an aqueous sugar stream. More particularly, the invention relates to a process for obtaining one or more than one organic salt or organic acid from an aqueous sugar stream comprising one or more than one mineral acid and a sugar(s).

2. Related Art

Fuel ethanol is currently produced from feedstocks such as corn starch, sugar cane, and sugar beets. However, the potential for production of ethanol from these sources is limited as most of the farmland which is suitable for the production of these crops is already in use as a food source for humans. Furthermore, the production of ethanol from these feedstocks has a negative impact on the environment because fossil fuels used in the conversion process produce carbon dioxide and other byproducts.

The production of ethanol from cellulose-containing feedstocks, such as agricultural wastes, grasses, and forestry wastes, has received much attention in recent years. The reasons for this are that these feedstocks are widely available and inexpensive and their use for ethanol production provides an alternative to burning or landfilling lignocellulosic waste materials. Moreover, a byproduct of cellulose conversion, lignin, can be used as a fuel to power the process instead of fossil fuels. Several studies have concluded that, when the entire production and consumption cycle is taken into account, the use of ethanol produced from cellulose generates close to nil greenhouse gases.

The lignocellulosic feedstocks that are the most promising for ethanol production include (1) agricultural wastes such as corn stover, wheat straw, barley straw, oat straw, rice straw, canola straw, and soybean stover; (2) grasses such as switch grass, miscanthus, cord grass, and reed canary grass; and (3) forestry wastes such as aspen wood and sawdust.

The three primary constituents of lignocellulosic feedstocks are cellulose, which comprises 30% to 50% of most of the key feedstocks; hemicellulose, which comprises 15% to 35% of most feedstocks, and lignin, which comprises 15% to 30% of most feedstocks. Cellulose and hemicellulose are comprised primarily of carbohydrates and are the source of sugars that can potentially be fermented to ethanol. Lignin is a phenylpropane lattice that is not converted to ethanol.

Cellulose is a polymer of glucose with beta-1,4 linkages and this structure is common among the feedstocks of interest. Hemicellulose has a more complex structure that varies among the feedstocks. For the feedstocks of interest, the hemicellulose typically consists of a backbone polymer of xylose with beta-1,4 linkages, with side chains of 1 to 5 arabinose units with alpha-1,3 linkages, or acetyl moieties, or other organic acid moieties such as glucuronyl groups.

The first process step for converting lignocellulosic feedstock to ethanol involves breaking down the fibrous material. The two primary processes are acid hydrolysis, which involves the hydrolysis of the feedstock using a single step of acid treatment, and enzymatic hydrolysis, which involves an acid pretreatment followed by hydrolysis with cellulase enzymes.

In the acid hydrolysis process, the feedstock is subjected to steam and a mineral acid, such as sulfuric acid, hydrochloric acid, or phosphoric acid. The temperature, acid concentration and duration of the hydrolysis are sufficient to hydrolyze the cellulose and hemicellulose to their monomeric constituents, which is glucose from cellulose and xylose, galactose, mannose, arabinose, acetic acid, galacturonic acid, and glucuronic acid from hemicellulose. Sulfuric acid is the most common mineral acid for this process. The sulfuric acid can be concentrated (25-80% w/w) or dilute (3-8% w/w). The resulting aqueous slurry contains unhydrolyzed fiber that is primarily lignin, and an aqueous solution of glucose, xylose, organic acids, including primarily acetic acid, but also glucuronic acid, formic acid, lactic acid and galacturonic acid, and the mineral acid. The aqueous solution is separated from the fiber solids to produce a sugar hydrolyzate stream.

In the enzymatic hydrolysis process, the steam temperature, mineral acid (typically sulfuric acid) concentration and treatment time of the acid pretreatment step are chosen to be milder than that in the acid hydrolysis process. Similar to the acid hydrolysis process, the hemicellulose is hydrolyzed to xylose, galactose, mannose, arabinose, acetic acid, glucuronic acid, formic acid and galacturonic acid. However, the milder pretreatment does not hydrolyze a large portion of the cellulose, but rather increases the cellulose surface area as the fibrous feedstock is converted to a muddy texture. The pretreated cellulose is then hydrolyzed to glucose in a subsequent step that uses cellulase enzymes. Prior to the addition of enzyme, the pH of the acidic feedstock is adjusted to a value that is suitable for the enzymatic hydrolysis reaction. Typically, this involves the addition of alkali to a pH of between about 4 and about 6, which is the optimal pH range for cellulases, although the pH can be higher if alkalophilic cellulases are used.

In one type of pretreatment process, the pressure produced by the steam is brought down rapidly with explosive decompression, which is known as steam explosion. Foody, (U.S. Pat. No. 4,461,648) describes the equipment and conditions used in steam explosion pretreatment. Steam explosion with sulfuric acid added at a pH of 0.4 to 2.0 has been the standard pretreatment process for two decades. It produces pretreated material that is uniform and requires less cellulase enzyme to hydrolyze cellulose than other pretreatment processes.

Regardless of whether acid hydrolysis or enzymatic hydrolysis is carried out, the resulting aqueous hydrolyzate stream is likely to contain glucose, xylose, arabinose, galactose, mannose, and organic acids, such as acetic acid, glucuronic acid, formic acid and galacturonic acid and the mineral acid, such as sulfuric acid. However, it will be appreciated that salts of the mineral acid and organic acid may be present and that the fraction of these acids in the salt form will increase with increasing pH. The glucose in this stream can be readily fermented to ethanol by conventional yeast or to butanol by bacteria. The pentose sugars can be fermented to ethanol by recombinant yeast (see U.S. Pat. No. 5,789,210 (Ho et al.) and WO 03/095627 (Boles and Becker)) or bacteria. Alternatively, the pentose sugars may be used as starting materials for the generation of other high value products using chemical, microbial or enzymatic means or simply recovered. For example, xylitol may be produced by the fermentation or hydrogenation of xylose or the xylose may be simply recovered.

The presence of the organic acid and mineral acid, or the corresponding salts, in a hydrolyzate stream decrease the efficiency of processes for converting glucose or other sugars to ethanol or other valuable products. In particular, during any neutralization conducted prior to enzymatic hydrolysis or fermentation (both of which take place at moderate pH values such as at pH values of about 4.0 to about 6.0), these compounds will consume alkali, such as sodium hydroxide, ammonium hydroxide, or potassium hydroxide. In addition, the mineral acids and organic acids, and their salts, may be inhibitory to yeast, bacteria and, to a lesser extent, cellulase enzymes. Any such inhibition can decrease the efficiency of the fermentation and enzymatic hydrolysis operations by lengthening the time required for carrying out the fermentation or enzyme hydrolysis, increasing the amount of yeast or enzyme catalyst required and/or decreasing the final yields. It therefore may be desirable to remove these compounds from the hydrolyzate to produce a clean sugar stream. In addition it may also be advantageous to remove these compounds from sugar streams obtained from other than hydrolysis, depending on the circumstances.

Pfeiffer (U.S. Pat. No. 4,102,705) discloses the deacidification of xylose streams by the removal of acetic acid and the mineral acids of sulfuric, hydrochloric, or nitric acid by using a two-stage ion exchange process. Pfeiffer feeds the aqueous stream to the first anion exchange system to bind the mineral acid and allow xylose and acetic acid to pass through. The resin is regenerated with sodium hydroxide, thereby producing sodium chloride, sodium sulfate, or sodium nitrate salt. The stream containing xylose and acetic acid is evaporated to remove 90% of the acetic acid. The resulting xylose stream with the remaining acetic acid is fed to a second ion exchange system, which binds the acetic acid and allows the deacidified xylose stream to pass through. The ion exchange resin is regenerated with sodium hydroxide to generate sodium acetate salt.

The evaporation taught by Pfeiffer would be very extensive in order to remove 90% of the acetic acid from the aqueous stream. Acetic acid is less volatile than water, so this evaporation would dewater the stream almost to dryness. It is very difficult to carry out such an evaporation as the presence of precipitated solids leads to scale deposition and fouling of heat exchange surfaces.

Wooley et al. (In Lignocellulosic Biomass to Ethanol Process Design and Economics Utilizing Co-Current Dilute Acid Prehydrolysis and Enzyme Hydrolysis Current and Future Scenarios, (1999) Technical Report, National Renewable Energy Laboratory pp. 16-17), reports removing 88% of the acetic acid and 100% of the sulfuric acid from a sugar hydrolyzate stream by using a continuous ion exchange separations unit. The ion exchange media is a weak base anion exchange resin and the resin is regenerated with ammonia. The acetic acid and sulfuric acid are discharged from the unit in the same stream and disposed of in a wastewater treatment unit.

WO 2006/007691 (Foody and Tolan) discloses the use of ion exclusion chromatography at pH 5.0 to 10.0 to separate ammonium acetate and ammonium sulfate salts from sugar streams prior to fermentation of the sugar. This separation method relies on the use of a cation exchange resin in the ammonium form.

Wooley et al., (Ind. Eng. Chem. Res., 1998, 37:3699-3709) discloses the use of ion exclusion chromatography with cation exchange resins in the hydronium form to separate acetic acid and sulfuric acid from sugar hydrolyzate streams. In this process, sulfuric acid is excluded from the resin and passes through the resin first while the non-ionic sugars move more slowly through the resin. The feed streams are at pH 3.0 and below, and the resulting process separates the stream into sulfuric acid, sugar, and acetic acid streams. However, control and recovery of the three product streams in the process would be difficult and costly.

Anderson et al. (Ind. Eng. Chem., 1955, 47:1620-1623) discloses the use of strong base anion exchange resins as a means of separating a strong mineral acid from water soluble organic material. In this process, the strong base anion exchange resin is first converted to the sulfate form. The mineral acid is retained by the resin bed and the water soluble organic material passes through the resin bed and is not bound. The method is useful for binding and recovering strong acids such as sulfuric and hydrochloric acids and relies on the absence of a significant interaction between the water soluble organic material and the resin bed. As long as the sulfate form of the resin is available, the mineral acid will bind the resin. However, the process does not result in the separation of an organic acid or its salt from an aqueous sugar stream.

Barrier et al. (Integrated Fuel Alcohol Production Systems for Agricultural Feedstocks, Phase III, Quarterly Technical Report for the Period April-June 1995. Submitted by Tennessee Valley Authority Office of Agricultural and Chemical Development, TVA Contract No. TV-540881, 1985) discloses the use of anion exchange resins, including weak base anion exchange resins, to recover sulfuric acid from a hydrolyzate stream. The method is useful for the recovery of sulfuric acid but results in a mixed sugar-organic acid stream. The mixed sugar-organic acid stream is sent directly to a yeast fermentation to produce ethanol. Caustic is added to adjust the fermentation pH and yeast media components are also added. The ethanol containing solution is subsequently distilled to produce a fuel ethanol. However, there is no disclosure of recovery of the organic acid which is understood to remain in the still bottoms after ethanol distillation and is not recovered.

Therefore, there is not a satisfactory process for recovering organic acids, or their corresponding salts, from aqueous sugar streams. The ability to remove organic acids, or their salts, from sugar streams remains a critical requirement to improve the efficiency of converting sugar to ethanol or other valuable products.

SUMMARY OF THE INVENTION

The present invention provides a process for obtaining one or more than one organic salt or organic acid from an aqueous sugar stream. More particularly, the invention relates to a process for obtaining one or more than one organic salt or organic acid from an aqueous sugar stream comprising one or more than one mineral acid and a sugar.

It is an object of the present invention to provide an improved method of obtaining an organic acid or salt from an aqueous sugar stream.

According to a first aspect of the invention, there is provided a process (A) for obtaining an organic salt or organic acid from an aqueous sugar stream comprising a mineral acid, an organic acid, and a sugar selected from the group consisting of xylose, glucose, arabinose, galactose, mannose and a combination thereof, said process comprising the steps of:

(i) introducing the aqueous sugar stream to a separation system comprising one or more beds of anion exchange resin and obtaining at least one stream therefrom comprising the sugar;

(ii) regenerating the one or more beds of anion exchange resin in one or more stages, thereby producing at least one stream comprising the mineral acid, a salt of the mineral acid, or a combination thereof, and at least one separate product stream comprising the organic acid, a salt of the organic acid, or a combination thereof; and (iii) recovering the at least one product stream.

According to this aspect of the invention, the anion exchange separation system may comprise separate first and second anion exchange units as described below. Alternatively, steps (i)-(iii) may be carried out in a single anion exchange unit comprising at least one resin bed. When the separation is carried out in a single anion exchange unit, the mineral acid, organic acid, and/or anions of these acids, bind to the resin bed(s) of the unit and the resin bed(s) is subsequently regenerated to displace the bound species.

According to a second aspect of the invention, there is provided a process (B) for obtaining one or more than one organic salt or organic acid from an aqueous sugar stream comprising one or more than one mineral acid, the one or more than one organic acid, and a sugar selected from the group consisting of xylose, glucose, arabinose, galactose, mannose and a combination thereof, said process comprising:

(i) introducing the aqueous sugar stream to a first anion exchange unit comprising one or more than one bed comprising an anion exchange resin, wherein the mineral acid, an anion of the mineral acid or a combination thereof binds to the resin;

(ii) producing an effluent stream comprising the sugar and the organic acid from the first anion exchange unit and regenerating the anion exchange resin with one or more regenerant, thereby producing one or more outlet streams comprising the mineral acid, a salt of the mineral acid or a combination thereof;

(iii) feeding the effluent stream comprising the sugar and the organic acid to a second anion exchange unit comprising one or more than one bed comprising an anion exchange resin, wherein the organic acid or an anion of the organic acid binds to the resin;

(iv) obtaining a stream from the second anion exchange unit comprising the sugar, which stream is substantially free of the mineral acid and the organic acid and regenerating the second anion exchange unit with one or more regenerant, thereby producing one or more product streams comprising a salt of the organic acid, the organic acid or a combination thereof; and (v) recovering the one or more product streams.

The present invention also pertains to the process (B) defined above, wherein, in the step of feeding (step (iii)), at least about 70% of the organic acid present in the aqueous stream is fed to the second anion exchange unit.

The anion exchange resin bed in the first anion exchange unit, the second anion exchange unit or both the first and the second anion exchange units may comprise a weak or a strong base anion exchange resin. Preferably, the anion exchange resin is a weak base resin.

The present invention also pertains to the processes (A or B) as defined above which further comprise a step of recovering the salt of the mineral acid, the mineral acid or a combination thereof.

The present invention also pertains to the processes (A or B) as defined above, wherein the mineral acid is selected from the group consisting of sulfuric acid, sulfurous acid, hydrochloric acid, phosphoric acid and a combination thereof. Preferably, the mineral acid is sulfuric acid.

Furthermore, the present invention relates to the processes (A or B) as defined above, wherein the organic acid is selected from the group consisting of acetic acid, formic acid, galacturonic acid, glucuronic acid and a combination thereof. Preferably, the organic acid is acetic acid.

The present invention also relates to the processes (A or B) as defined above, wherein the acetic acid is recovered from the one or more product streams. Acetic acid may be recovered from the product stream by distillation, by liquid-liquid extraction or by stripping with air or steam. In one embodiment of the invention, the one or more product streams comprise a salt of acetic acid and the pH of the product stream(s) is adjusted to 4 or lower by the addition of acid prior to recovering the acetic acid.

The present invention also relates to the processes (A or B) as defined above, wherein the regenerant(s) is an aqueous solution selected from an acid solution, an alkali solution or water. Preferably, the regenerant is an alkali or acid solution. If the regenerant is alkali, it is preferably an alkali solution selected from the group consisting of aqueous ammonia (also referred to as ammonium hydroxide), a sodium hydroxide solution and a potassium hydroxide solution. Most preferably, the base is aqueous ammonia or ammonium hydroxide.

The present invention also relates to the processes (A or B) as defined above, wherein the anion exchange is a Simulated Moving Bed (SMB) system or an Improved Simulated Moving Bed (ISMB) system.

The present invention also relates to the processes (A or B) as defined above, wherein the aqueous sugar stream is obtained by pretreating a lignocellulosic feedstock at a pH of about 0.4 to about 5.0 by adding one or more than one acid to the lignocellulosic feedstock to hydrolyze at least a portion of the hemicellulose in the feedstock. The present invention also relates to the processes (A or B) as defined above, wherein the aqueous sugar stream is at a pH of 0.4 to about 5.0. Alternatively, the aqueous sugar stream is a hydrolyzate stream resulting from adding an acid to a lignocellulosic feedstock to hydrolyze both hemicellulose and cellulose present in said lignocellulosic feedstock to their respective sugar monomers.

According to another aspect of the invention, there is provided a process (C) for obtaining acetate salt, acetic acid or a combination thereof, from a lignocellulosic feedstock comprising the steps of:

(i) obtaining an aqueous sugar stream resulting from hydrolysis of the lignocellulosic feedstock, said hydrolysis comprising one or more stages of sulfuric acid addition, said sugar stream comprising acetic acid, acetate salt, or a combination thereof, sulfuric acid and one or more sugars selected from xylose, glucose, arabinose, galactose, mannose or a combination thereof;

(ii) introducing the aqueous sugar stream to a Simulated Moving Bed separation system comprising one or more beds of anion exchange resin and obtaining at least one product stream therefrom comprising the one or more sugars;

(iii) regenerating the one or more beds of anion exchange resin with sulfuric acid, thereby producing at least one organic acid product stream comprising the acetic acid and thereafter, regenerating the one or more beds of anion exchange resin with ammonium hydroxide to produce at least one separate outlet stream comprising ammonium sulfate; and (iv) recovering the product stream.

The present invention also relates to the process (C) as defined above, wherein the sulfuric acid addition is conducted to pretreat the lignocellulosic feedstock, thereby hydrolyzing at least a portion of hemicellulose present in said lignocellulosic feedstock to sugar monomers. Alternatively, the sulfuric acid addition is conducted to hydrolyze both the hemicellulose and cellulose present in said lignocellulosic feedstock to their respective sugar monomers.

The present invention overcomes the limitations of the prior art. The ion exchange process is suitable for acidic hydrolyzate streams, unlike ion exclusion processes. Moreover, the anion exchange process of the invention typically does not require large amounts of dilution water typical of ion exclusion operations, but rather the mineral and organic salts or their acids can be obtained in their concentrated form. The process of the invention does not depend on the use of evaporation to remove the organic acid, and therefore can avoid this cost. Furthermore, the process of the invention can produce mineral salt and organic salt, or their respective acids, in separate streams at higher concentrations than present in the original feed stream. The separate and concentrated nature of the mineral and organic salt or acid streams facilitates recovery and further processing of these compounds.

The invention therefore represents a significant step forward in the processing of lignocellulosic feedstocks for the production of ethanol or other products.

BRIEF DESCRIPTION OF THE DRAWINGS

These and other features of the invention will become more apparent from the following description in which reference is made to the appended drawings wherein:

FIG. 8A shows the xylose elution profile from a weak base anion exchange resin bed subsequent to feeding an aqueous stream comprising xylose, sulfuric acid and acetic acid. The aqueous stream was fed until just prior to 1% breakthrough of acetic acid. FIG. 8B shows the regeneration profiles of acetate, sulfate and ammonium after two regeneration stages, wherein each of the regeneration stages involved the addition of aqueous ammonia.

DETAILED DESCRIPTION OF THE INVENTION

Figure 1:
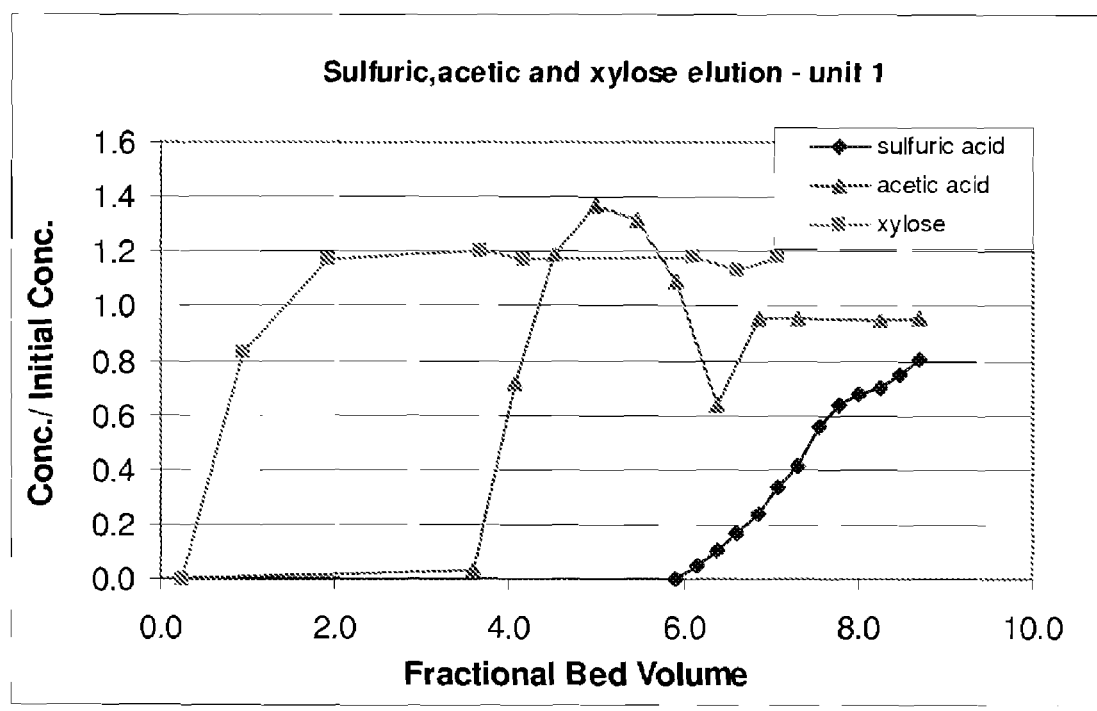
FIG. 1 shows the elution profiles of sulfuric acid, acetic acid and xylose from a weak base anion exchange column. The column was fed with an aqueous sugar stream obtained from the pretreatment of wheat straw.

The present invention provides a process for obtaining one or more than one organic salt or organic acid from an aqueous sugar stream. More particularly, the invention relates to a process for obtaining one or more than one organic salt or organic acid from an aqueous sugar stream comprising one or more than one mineral acid and a sugar monomer, for example, selected from xylose, glucose, arabinose, galactose, mannose or a combination thereof.

The following description is of a preferred embodiment.

The process of the invention involves the use of anion exchange resins to achieve separation of the mineral acid and organic acid from the aqueous sugar stream. This comprises the exchange of anions in the aqueous stream with anions on the resin (strong base anion exchange) or acid adsorption onto the resin (weak base anion exchange), followed by a subsequent regeneration step to displace the bound species. Sugars have low affinity for the resin and elute from the resin first while the mineral acid and organic acid or their anions are retained. The process of the invention is distinguished from ion exclusion chromatographic separation techniques which rely on a different mechanism of separation. Ion exclusion uses ion exchange resins in a form such that the target ionic compounds are excluded from the resin due to charge repulsion. The excluded compounds elute from the column quickly, while uncharged compounds absorb into the resin and elute from the column more slowly.

The aqueous stream may originate from the processing of a lignocellulosic feedstock. Representative lignocellulosic feedstocks are (1) agricultural wastes such as corn stover, wheat straw, barley straw, oat straw, rice straw, canola straw, and soybean stover; (2) grasses such as switch grass, miscanthus, cord grass, and reed canary grass; and (3) forestry wastes such as aspen wood and sawdust. These feedstocks contain high concentrations of cellulose and hemicellulose that are the source of the sugar, including sugar monomers for example glucose and xylose, in the aqueous stream. However, the practice of the invention is not limited by the feedstock used.

The aqueous sugar stream used in the practice of the invention comprises mineral acid(s), organic acid(s), and sugar(s). Preferably, the aqueous sugar stream is produced by subjecting the feedstock to acid hydrolysis or pretreatment, with the acid used being a mineral acid. The acid hydrolysis or pretreatment processes can be any that are familiar to those of skill in the art. In one embodiment of the invention, the pretreatment is conducted at pH 0.4 to 5.0 to hydrolyze hemicellulose present in the feedstock. For example, the pretreatment may be conducted at 0.4, 0.5, 1.0, 1.5, 2.0, 2.5, 3.0, 3.5, 4.0, 4.5 or 5.0. However, the practice of the invention is not limited to the use of acid hydrolysis or pretreatment, or a specific process used to produce the aqueous sugar stream.

The sugar may include a sugar monomer, for example, a sugar monomer selected from xylose, glucose, arabinose, galactose, mannose or a combination thereof.

The mineral acid preferably arises from an acid hydrolysis or pretreatment process, and is carried into the aqueous sugar stream. Regardless of its source, the mineral acid may be selected from, but is not limited to, sulfuric acid, sulfurous acid, hydrochloric acid, or phosphoric acid. Preferably, the mineral acid is sulfuric acid. Although the sugar stream for use in the invention may comprise hydrochloric acid, this acid suffers from the disadvantage that it introduces chloride ions into solution. Thus, for certain applications, it may be preferred that the aqueous sugar stream does not comprise hydrochloric acid, especially in cases where the metallurgy of the system must be protected from the corrosive effect of this acid.

The organic acids may include acetic acid, galacturonic acid, formic acid, lactic acid, glucuronic acid or a combination thereof. The group of organic acids preferably includes acetic acid. Acetic acid may be generated by acid hydrolysis or pretreatment of the lignocellulosic feedstock. Many lignocellulosic feedstocks contain hemicellulose with acetyl groups attached to xylan. The acid hydrolysis or pretreatment processes liberate acetic acid from the acetyl groups. However, the practice of the invention is not limited to the use of sugar hydrolyzate streams which comprise acetic acid formed by the hydrolysis of acetyl groups.

The aqueous sugar stream may be subjected to cation exchange prior to being fed to an anion exchange separation system. Cation exchange can be employed to remove potassium, calcium, magnesium, sodium, and other cations that are present in the sugar stream. Removal of these cations reduces the likelihood of precipitation of compounds of low solubility, for example calcium hydroxide and calcium sulfate. Removal of the cations can also benefit the subsequent anion exchange.

The aqueous sugar stream is preferably substantially free of undissolved or suspended solids. This may be achieved by filtration, centrifugation, or other processes for removing fiber solids or suspended solids from aqueous streams that are familiar to those skilled in the art. Optionally, the aqueous sugar stream is concentrated, for example, by evaporation or with membranes, or the like. It is also contemplated that a portion of the mineral acid is removed from the aqueous sugar stream prior to feeding it to the anion exchange separation system, for example, by chromatographic separation or other means.

The mineral acid may be present in the aqueous sugar stream at a concentration of about 0.5 g/L to about 100 g/L, or any concentration range therebetween. A more preferred mineral acid concentration is about 1 g/L to about 50 g/L, or any concentration range therebetween.

The organic acids concentration in the aqueous sugar stream may be about 1 g/L to about 60 g/L, or any concentration range therebetween. In a more preferred embodiment, the organic acids concentration is about 2 g/L to about 50 g/L, or any concentration range therebetween. Preferably, the aqueous sugar stream comprises acetic acid and sulfuric acid. The concentration of acetic acid can be less than or greater than sulfuric acid. The ratio of the concentration of acetic acid to that of sulfuric acid may be less than about 4.0:1.0.

The combined concentration of sugars in the aqueous sugar stream may be about 10 g/L to about 250 g/L, or any concentration range therebetween. In a more preferred embodiment, the combined concentration of sugars is 25 g/L to 100 g/L, or any concentration range therebetween. With respect to the glucose and xylose in the aqueous sugar stream, the weight ratio of glucose to xylose may range from 0:100 to 100:0, or any ratio therebetween; for example, the weight ratio of glucose to xylose may be 0:100, 5:95, 10:90, 20:80, 30:70, 40:60, 50:50, 60:40, 70:30, 80:20, 90:10 or 100:0 or any ratio therebetween.

The total solutes concentration in the aqueous sugar stream may be as low as about 20 g/L and as high as about 600 g/L, or any concentration range therebetween. For example, the total solutes concentration may be about 30 g/L to about 400 g/L, or any range therebetween. Preferably, the total solutes concentration is about 40 g/L to about 300 g/L, or any range therebetween.

The aqueous stream is at an acidic pH for effective processing by anion exchange. In a non-limiting example, the aqueous stream is at a pH of 0.4 to about 5.0, or any pH range therebetween, as it is fed to the anion exchange separation system. In this pH range, the pH is approximately equal to, or lower than, the pKa of the organic acids present. For example, the pKa of acetic acid is 4.75. In a more preferred embodiment, the aqueous stream is at a pH of 0.4 to about 4.0, or any pH range therebetween. In a most preferred embodiment, the aqueous stream is at a pH of 0.4 to about 3.0, or any pH range therebetween. For example, the pH may be 0.4, 0.5, 1.0, 1.5, 2.0, 2.5, 3.0, 3.5, 4.0, 4.5 or 5.0, or any pH range therebetween.

The aqueous stream is preferably at a temperature of about 20° C. to about 90° C., or any temperature therebetween. More preferably, the temperature is about 45° C. to about 75° C., or about 55° C. to about 70° C., or any temperature therebetween. For example, the temperature may be 20, 25, 30, 35, 40, 45, 50, 55, 60, 65, 70, 75, 80, 85 or 90° C., or any temperature therebetween.

The aqueous sugar stream may comprise compounds other than the mineral acids, organic acids and sugars. For example, the aqueous sugar stream may comprise other inorganic compounds, including, but not limited to, potassium sulfate, calcium sulfate, magnesium sulfate, or sodium sulfate. The aqueous sugar stream may also contain other organic compounds, including but not limited to, furfural, hydroxymethyl furfural, dissolved lignin, and the like. The concentration of these compounds may be from about 0% to about 75% of the total solutes present in the aqueous stream, or from about 0% to about 50% of the total solutes present in the aqueous sugar stream.

The anion exchange resin may be a weak base anion exchange resin. By a weak base anion exchange resin, it is meant a resin with a polymeric structure comprising a weak base functional group. A common weak base functional group found in weak base anion exchange resins is a tertiary amine. Amines such as trialkyl amines and pyridine are found commonly in weak base anion exchange resins, although it should be appreciated that other functional groups may be used.

Alternatively, the anion exchange resin is a strong base anion exchange resin. By a strong base anion exchange resin, it is meant a resin with a polymeric structure comprising a strong base functional group. A common strong base functional group found in strong base anion exchange resins is a quaternary amine, although it should be appreciated that other functional groups may be used. The strong base anion exchange resin may be a Type I or Type II (Dianion Manual of Ion Exchange Resins and Synthetic Adsorbent, Mitsubishi Chemical Corporation, $2^{nd}$ edition, 1995) strong base anion exchange resin. Type I strong base anion exchange resins comprise a stronger base functional group than Type II resins. Typically, a Type II resin comprises a quarternary ammonium functional group where one of the four nitrogen substituents comprises an aminoethanol group. However, any functional group that renders the quaternary ammonium functional group less basic may be present in Type II strong base anion exchange resins.

A common polymeric structure for a strong or weak base resin is formed using divinyl benzene cross-linked polystyrene; however, any suitable polymer or cross-linking agent known to those skilled in the art can be used. For example, anion exchange resins may also be formed using an acrylic polymeric support. A polymeric backbone can also be formed using various levels of cross-linking agent to control the porosity of the polymeric structure.

The weak base or strong base anion exchange resins may be macroporous, i.e., containing discrete pores, microporous (gel resins) or may contain elements of both these structures. Weak or strong base anion exchange resins may be prepared to contain a narrow range of particle shape and size or a wide range of particle shape and sizes. The total operating capacity of the anion exchange resin may vary depending on the process used to prepare the resin. Furthermore, anion exchange resins can vary depending on the nature of the polymeric structure, supplier, lots, synthesis methods, process parameters, or functional group. This results in resins that differ in certain parameters such as pressure drop, swelling and shrinking, moisture holding capacity, diameter, porosity, thermal stability, physical stability, and the like. However, it is to be understood that the invention is not limited by the specific physical and chemical properties of the resin employed.

Although the use of weak and strong base resins falls within the scope of the invention, weak base resins are preferred over strong base resins for various reasons. A weak base resin typically consumes lower quantities of alkali when regeneration is carried out compared to strong base resins. In addition, weak base resins can be regenerated using a weak base, such as ammonium hydroxide, which can be advantageous for recovering the mineral and organic acids from the regenerated salts. Furthermore, a weak base resin does not increase the pH of the sugar streams in the resin bed to highly alkaline values. Such highly alkaline conditions can cause the degradation of sugars (for example xylose) and the ionization of sugars which can bind to strong base anion exchange resins reducing yields.

In one embodiment of the invention, the process comprises two anion exchange units to achieve separation of the mineral acid and organic acid from the aqueous sugar stream. According to this embodiment, the aqueous sugar stream is fed to the first anion exchange unit comprising a resin bed that binds the mineral acid or its anion. A low-affinity effluent stream is obtained from the first unit that comprises the organic acid(s) and the sugar(s) which, in turn, is fed to the second anion exchange unit. The resin of the first anion exchange unit is then regenerated by an aqueous regenerant, which may be water, to obtain an outlet stream comprising the mineral acid, the mineral salt, or a combination thereof. The resin is preferably regenerated by an alkali, including, but not limited to, ammonium hydroxide, potassium hydroxide, or sodium hydroxide to produce a mineral salt. The mineral salt may be recovered or may be processed and recovered as the mineral acid.

The second anion exchange unit uses an anion exchange resin to bind the organic acid or an anion of the organic acid. Preferably, more than about 70% of the organic acid in the aqueous sugar stream proceeds to the second unit. The stream obtained from the second anion exchange unit is then a stream comprising, but not limited to, a sugar monomer, for example, xylose, glucose, or a combination thereof, that is essentially free of organic acid and mineral acid. The resin is subsequently regenerated with an aqueous regenerant, which may be water, to obtain a product stream comprising the organic acid, the organic salt, or a combination thereof. In one embodiment, the resin is regenerated by an alkali, including, but not limited to, ammonium hydroxide, potassium hydroxide, or sodium hydroxide to produce an organic salt. The organic salt may then be recovered or is processed and recovered as the organic acid.

The anion exchange resin(s) are typically packed in vertical columns, horizontal beds, or a combination thereof. The first and/or the second anion exchange units may comprise multiple beds which are arranged in parallel, in series, or may include a combination of beds arranged in series and in parallel. However, the practice of the invention is not limited by the arrangement of beds. As would be apparent to one of skill in the art, in either case, the volume of the resin bed is typically chosen based on the flow rate and the concentration of acids or anions in the aqueous stream. The sizing of resin beds may be carried out by combining the data from laboratory, or other experiments, on the aqueous sugar stream with design principles that are familiar to those skilled in the art.

The mineral acid, or its anion, binds to the resin since it has the highest affinity for the resin of the major compounds present. Without wishing to be bound by theory, if a strong base anion exchange resin is used, the anion of the mineral acid will bind to the resin and if a weak base anion exchange resin is used, the mineral acid will bind to the resin. The sugars and most other inorganic and organic compounds have limited affinity for the resin and pass through the resin bed. The organic acids have an intermediate level of affinity for the resin and bind to the resin initially, but are displaced by the mineral acid and desorb. The effluent stream from the resin bed of the first anion exchange unit comprising the sugar and organic acids may be fed directly to the second anion exchange unit, or may be collected and pooled, and subsequently fed to the second anion exchange unit.

Preferably, the aqueous feed continues until the mineral acids are detected in the effluent stream. This is the point at which, if the feed was continued, a significant concentration of mineral acid would exit the resin bed. The amount of feed that can be added prior to mineral acid leakage can be determined by bed overload experiments familiar to those skilled in the art and shown in Examples 1 and 2. In a non-limiting example, the aqueous sugar stream is fed to one or more than one resin bed in the first anion exchange unit until the mineral acids are first detected in the effluent. The detection can be carried out by a direct measurement of the amount of mineral acid in the effluent or other indicators known to those of skill in the art, for example, conductivity, pH or other means. Once the mineral acids are detected, the feed is stopped. However, it should be appreciated that if the beds are arranged in series, the leaked acids would, in practice, be detected from the final bed in the series. The liquid held up in the bed is optionally removed by rinsing, draining, or blowing out. The resin bed(s) is then regenerated with a suitable regenerant, including, but not limited to, an aqueous regenerant, including, but not limited to an alkali, for example, ammonium hydroxide, sodium hydroxide, or potassium hydroxide. The feeding of the regenerant with alkali produces salts of the mineral acids and any of the remaining organic acids. For example, if sulfuric acid is present in the aqueous stream, a sulfate salt of ammonium, sodium, or potassium is produced after the addition of ammonium hydroxide, sodium hydroxide or potassium hydroxide, respectively. If a sulfate salt is produced, it may be collected and can be recovered, for example for use as fertilizer. Alternatively, the sulfate salt can be processed, for example by cation exchange, to produce sulfuric acid.

The present invention is not limited by the amount or number of regenerants applied to the first anion exchange unit. It will be understood by those of skill in the art that the resin may be regenerated with one or more regenerants introduced in one or more separate steps and that it may be advantageous to use the minimum amount of regenerant necessary to displace a desired amount of bound acid or anion. Accordingly, it is preferred to use aqueous solutions comprising acids or alkali as the regenerants since they produce more concentrated streams resulting from the regeneration.

The concentration of the regenerant is about 2 g/L to about 250 g/L, or any concentration range therebetween. In the case of bound sulfuric acid, when the regenerant is alkali, a high regenerant concentration produces concentrated sulfate salts. Thus, the choice of operating conditions may be selected to avoid precipitation of sulfate salts. More preferably, the regenerant concentration is about 10 g/L to about 150 g/L, or any concentration range therebetween.

Preferably, the regenerant is fed until the mineral acid is completely desorbed from the resin bed. The regenerant may be fed until more than about 80%, or, preferably, more than about 90% of the mineral acid is desorbed from the resin bed.

The regenerant can be fed to the column(s) in the same direction as the aqueous feed, known as a co-current regeneration. Alternatively, the regenerant may be fed countercurrent, i.e., in the opposite direction to the aqueous feed. Following regeneration, the column(s) are optionally rinsed with water or other aqueous streams prior to resuming feed of the aqueous stream.

The stream with the lowest affinity for the resin, or effluent stream, comprising sugar and the organic acids is fed to the second anion exchange unit. This stream may optionally be concentrated by other means prior to feeding to the second unit. If evaporation is employed, then it should be carried out so that a substantial portion of the organic acids is carried forward. For example, it is preferred that at least about 70% of the organic acids, and more preferably greater than 70% of the acetic acid, present in the aqueous stream fed to the first stage are present in the second stage feed. Preferably, at least about 90% of the organic acids are fed to the second unit. More preferably, at least about 95% of the organic acids are fed to the second unit.

Although evaporation of the effluent from the first unit of the anion exchange falls within the scope of the invention, it is preferred that such an evaporation step is not carried out.

Preferably, at least about 90% of the sugars in the feed to the first unit pass through to the second unit. More preferably at least about 95%, or even more preferably about 98%, of the sugar passes through to the second unit.

Like the first anion exchange unit, the second anion exchange unit comprises a resin bed with an anion exchange resin. The first and the second anion exchange units may employ either a strong or a weak base anion exchange resin. For example, both anion exchange units may comprise strong anion exchange resins or weak base anion exchange resins or either one of the two units may employ a strong base anion exchange resin with the other using a weak base anion exchange resin.

As the effluent stream from the first unit is fed to the second anion exchange unit, the organic acids bind to the resin while sugars and other organics which have a low affinity for the resin pass through the resin bed. Without wishing to be bound by theory, if a strong base anion exchange resin is used, the anion of the organic acid binds to the resin and if a weak base anion exchange resin is used, the organic acid binds to the resin. The sugar stream from the second anion exchange unit may be fed to fermentation or other processing. This stream may be optionally concentrated by membrane filtration or other methods known to those skilled in the art prior to fermentation or to further processing.

Preferably, the effluent stream from the first anion exchange unit is fed to the second anion exchange unit until the organic acids are detected in the effluent stream from the second unit. The detection can be carried out by a direct measurement of the amount of organic acid in the effluent or by other indicators known to those of skill in the art, for example, conductivity, pH or other means. The amount of feed that can be added prior to organic acid leakage is determined by bed overload experiments familiar to those skilled in the art and shown in Examples 1 and 2. Preferably, once the organic acids are detected, the feed is stopped. However, it should be appreciated that if the beds are arranged in series, the leaked acids would, in practice, be detected from the final bed in the series. If the beds are arranged in parallel, the leaked acids are typically detected in the effluent from each column. The liquid held up in the bed is optionally removed by rinsing, draining, or blowing out.

The resin bed is then regenerated with one or more suitable regenerant, which may be any aqueous regenerant, which may be water, to obtain a stream comprising the organic acid, the organic salt, or a combination thereof. If the regenerant is alkali, it is preferably ammonium hydroxide, sodium hydroxide, or potassium hydroxide. In the case of acetic acid, if ammonium hydroxide, sodium hydroxide or potassium hydroxide are used as regenerants, their respective acetate salts are produced, namely ammonium acetate, sodium acetate, or potassium acetate. The acetate salt is then recovered. The concentration of regenerant may be about 2 g/L to about 250 g/L, or any concentration range therebetween. More preferably, the regenerant concentration is about 10 g/L to about 150 g/L, or any concentration range therebetween.

Similar to the first anion exchange unit, the second anion exchange unit may be regenerated using more than one regenerant in separate steps. Although any regenerant may be utilized, it may be advantageous to use an aqueous solution comprising acid or alkali to minimize the amount of regenerant necessary to displace a desired amount of bound acid or anion.

In a non-limiting example, the regenerant is fed until the organic acid is completely or substantially desorbed from the resin bed. The regenerant may be fed until more than about 80% of the organic acid is desorbed from the resin bed, or, preferably, more than about 90% of the organic acid is desorbed from the resin bed.

If an acetate salt is produced during regeneration, this salt may be recovered or further processed. The salt may also be recovered as acetic acid. The acetic acid may be recovered from the acetate salt by distilling the acetate salt, preferably after adjustment of the pH to below about 4.0 with a nonvolatile acid such as sulfuric acid. In one embodiment, the pH is adjusted to below about 3.5, 3.0, 2.5, 2.0 or 1.5 with a nonvolatile acid. Alternatively, the acetic acid may be recovered from the acetate salt solution by liquid-liquid extraction or by stripping the acetic acid with air or steam.

The process of the invention may be carried out using a Simulated Moving Bed (SMB) system. By the term "SMB system", it is meant any continuous chromatographic technique which simulates a flow of a liquid mobile phase moving countercurrent to a flow of a solid stationary phase, i.e., the SMB system simulates movement of the resin bed in a direction opposite to that of the liquid flow. Typically, an SMB system comprises a set of fixed beds connected in a closed circuit with two or more inlet and two or more outlet streams. The simulated movement may be carried out by periodically shifting four or more flow locations by some fraction of the total bed. A description of the operation of an SMB system is provided in WO 2006/007691 (Foody and Tolan), to which the reader is directed for reference and which is incorporated herein by reference. Improved SMB ("ISMB") systems (available for example from Eurodia Industrie S.A., Wissous, France; Applexion S.A., Epone, France; or Amalgamated Research Inc., Twin Falls, Id.) may also be used in the practice of the invention.

Although the use of a two-unit anion exchange separation system has been described, the process of the invention may alternatively comprise carrying out the separation on a single anion exchange unit. Similar to using a two-unit system, this embodiment relies on the differential affinity of the sugar(s), the organic acid(s) and the mineral acid(s) for the anion exchange resin. The aqueous feed is passed through the resin bed and the sugars and most other inorganic and organic compounds pass through the resin bed. Since the organic acids or the anions of the organic acids have an intermediate level of affinity for the resin, they bind to the resin initially. The mineral acid or the anion of the mineral acid, which has the highest affinity for the resin of the major compounds present, bind to the resin, displacing the organic acids which subsequently bind to another region of the resin bed. Preferably the feed is passed through the single anion exchange unit until the organic acids are first detected in the product stream. This is the point at which, if the feeding was continued, a significant concentration of organic acid would exit the resin bed. The amount of feed that can be added prior to organic acid leakage can be determined by bed overload experiments familiar to those skilled in the art and as set forth in the examples. The liquid held up in the bed is optionally removed by rinsing, draining or blowing out.

After the resin bed is loaded with both the organic acid and the mineral acid (or anions of these acids), it is regenerated. Similar to the process employing two-anion exchange units, when using a single anion exchange unit, the regeneration is conducted to produce two separate outlet streams, one comprising the organic acid or salts thereof, and one comprising the mineral acid, or salts thereof. However, in this embodiment, both arise from the same anion exchange unit rather than separate units as described previously.

The product stream comprising the organic acid or its salts may be obtained by regenerating the resin bed(s) with an aqueous regenerant, which may be water. The aqueous regenerant preferentially desorbs the organic acids or anions of the organic acids. The liquid held up in the bed is then optionally removed by rinsing, draining or blowing out. The resin bed(s) of the anion exchange unit comprising the bound mineral acid or anion of the mineral acid is subsequently regenerated with additional aqueous regenerant, which may be water, to obtain an outlet stream comprising the mineral acid or the mineral salt.

The preferred conditions and process equipment employed for the separation on a single anion exchange unit are as described in connection with the anion exchange system utilizing two separate units. Similar to the two-unit process, it is preferred that the regenerant(s) is selected from acid or alkali in order to minimize the amount of regenerant necessary to displace a desired amount of bound acid or anion. Furthermore, it should be appreciated that a different regenerant may be used in each regeneration stage. For example, the resin may be regenerated with acid, followed by the addition of alkali. Alternatively, the same regenerant is used to obtain both the product stream(s) containing the organic acid, or a salt thereof, and the outlet stream(s) comprising the mineral acid, or a salt thereof. The resin bed is typically a vertical column, horizontal bed, or a combination thereof, filled with anion exchange resin.

Although the process involves obtaining both the product and outlet streams from a single anion exchange unit, the system may further comprise multiple units arranged in parallel, with each unit being loaded with the organic acid and mineral acid (or their anions) and each subsequently regenerated to obtain separate product and outlet streams. The invention may also be practiced with a single unit comprising more than one resin bed in series.

The present invention will be further illustrated in the following examples.

EXAMPLES

Example 1

Separation of Sulfuric Acid from a Xylose Stream Using the First Unit of a Two-Unit Anion Exchange System An aqueous stream comprising xylose, sulfuric acid and acetic acid was prepared from wheat straw by using a steam and sulfuric acid pretreatment as described by Foody (U.S. Pat. No. 4,461,648, which is incorporated herein by reference). The pretreated wheat straw washed with water and the resulting sugar stream comprised the components shown in Table 1. The stream had a pH of 1.2. The sugar stream also comprised other organic acids, hexoses and other pentose sugars. Sulfuric and acetic acid concentration was measured using a Dionex ICS-2500 HPLC equipped with Chromeleon® software (version 6.6), an IonPac® AS11-HC column (4×250 mm), an AG11-HC guard column (4×50 mm), a conductivity detector and an anion self-regenerating suppression ultra-II system (ASRS-Ultra II). The method used an isocratic 1 mM NaOH mobile phase from 1 to 15 minutes, a 1 to 60 mM NaOH gradient mobile phase from 15 to 21 minutes and finally an isocratic 60 mM NaOH mobile phase from 25 to 30 minutes. Xylose was measured using the above HPLC system using a CarboPac™ PA1 column (4×250 mm) and guard (4×50 mm) column with pulsed amperometric detection. The method used a 10 mM NaOH isocratic mobile phase for fourteen minutes, an isocratic, 250 mM NaOH mobile phase from 14.1 to 16.7 minutes followed by an isocratic 10 mM NaOH mobile phase from 16.8 to 20 minutes.

TABLE 1

Aqueous stream feed to first unit of a two-unit anion exchange system

| Component | Concentration (g/L) |
| --- | --- |
| Sulfuric acid | 12.5 |
| Acetic acid | 4.82 |
| Xylose | 33.8 |

This aqueous stream was fed to the first unit of an anion exchange system. This first unit comprised a weak base anion exchange resin, DOWEX MARATHON WBA, which comprised a tertiary amine functional group and a styrene-divinylbenzene macroporous matrix. The mean particle size of this resin is 525 microns. The resin was first prepared by soaking in 85% methanol for 15 minutes and then rinsing with water. This wetting procedure is not necessary after the first time the resin is used and is not required for all weak base anion exchange resins. One hundred millilitres (100 mL) of prepared resin was used in a d=1.2 cm glass column. The stream was fed at a rate of 5.0 mL/minute through the column and samples of 23 mL were collected at the column exit. The first stage weak base anion exchange column was run at ambient temperature.

The elution profiles of xylose, acetic acid and sulfuric acid from the column are shown in FIG. 1. The xylose eluted from the bed almost immediately after the void volume exited the column. The void volume liquid (38 mL) is present in the column at the start of the experiment and is pushed out by the feed. The acetic acid bound to the resin until a volume of feed corresponding to nearly four times the volume of the resin bed had passed through the column. Beyond this point, acetic acid was detected in the effluent at concentrations up to 1.4 times the feed concentration.

Sulfuric acid has the highest affinity for the resin and was not detected in the effluent until 5.9 bed volumes had been fed. The 1% breakthrough capacity (point at which the effluent has 1% of the original concentration of sulfuric acid in the feed stream) of the resin for sulfuric acid was calculated to be 0.75 equivalents of sulfuric acid/L of resin (Equation 1). Feeding continued to 8.7 bed volumes to obtain a sufficient elution profile for sulfuric acid. In the process of the invention, wherein the effluent is fed into a second unit, feeding would stop when sulfuric acid is detected. The point at which feeding is stopped may be greater than or less than the 1% breakthrough point. The theoretical capacity for the MARATHON WBA resin used is 1.3 equivalents/L of resin.

$$(5.9 \text{ bed volumes})(0.1 \text{ L bed volume})(12.5 \text{ g/L sulfuric acid})/(98 \text{ g/equivalent})(0.1 \text{ L resin}) = 0.75 \text{ equivalents/Liter.} \quad \text{Equation 1}$$

Figure 2:
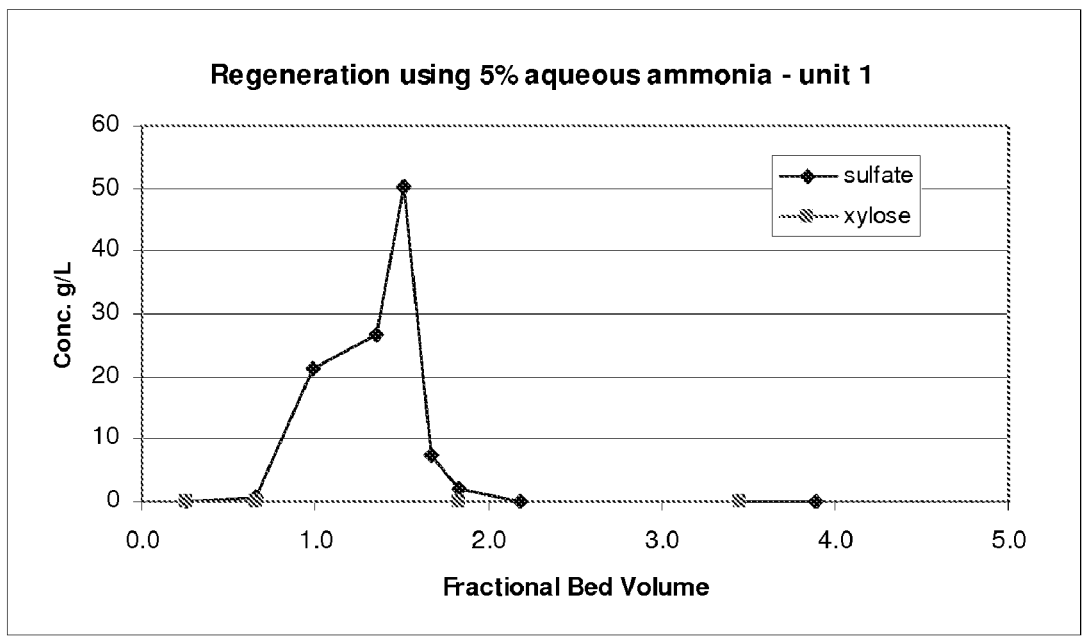
FIG. 2 shows the regeneration profile of the weak base anion exchange column subsequent to feeding 8.7 bed volumes of an aqueous sugar stream obtained from the pretreatment of wheat straw. Aqueous ammonia (5% w/v) was used as the regenerant.

After the feeding of 8.7 bed volumes of feed stream, the column was washed with one bed volume of water. The resin was then regenerated with 5 w/v % aqueous ammonia, which was fed at a rate of 5 mL/min. The amount of base used was 1.2 equivalents relative to the amount of sulfuric acid equivalents bound to the column. After feeding the base, water was used to wash the mineral salt off of the column. FIG. 2 shows the amount of sulfate obtained in g/L as a function of the fractional bed volume of combined liquid fed to the column. The bound sulfate was substantially removed from the column after 1.83 bed volumes of aqueous ammonia solution and wash water were fed. Table 2 indicates the concentration and yield of bound sulfate obtainable when sub-portions of the outlet streams are pooled. The pools are composed of the total volume collected between the indicated, initial (from fbv) and final (to fbv) outlet-stream fractional bed volume. The outlet streams contained sulfate (as ammonium sulfate) at higher concentrations than present (as sulfuric acid) in the original streams.

TABLE 2

Concentration and yield of sulfate in the outlet stream

| From fbv | To fbv | % Recovery | Concentration (g/L) |
|---|---|---|---|
| 1.4 | 1.5 | 32 | 50.2 |
| 0.66 | 1.5 | 91 | 26.4 |
| 0.66 | 1.83 | 97 | 20.2 |

Example 2

Separation of Acetic Acid from Xylose in the Second Unit of a Two-Unit Anion Exchange System An aqueous stream comprising xylose, sulfuric acid and acetic acid was produced from wheat straw by using a steam and sulfuric acid pretreatment as described by Foody in U.S. Pat. No. 4,461,648 and the pretreated wheat straw washed with water to produce a sugar stream which was then fed to a first unit of a two-unit anion exchange separation system as described in Example 1. The resulting aqueous sugar stream obtained from a pooled effluent of the first unit comprised the components reported in Table 3 below. The sugar stream also comprised other organic acids, hexoses and other pentose sugars. The pH of this stream was 3.5. This sugar stream was fed to the second unit of the two-unit system containing the same resin as in Example 1. This column had a bed volume of 50 mL and a diameter of 1.2 centimeters. The second weak base anion exchange column was run at ambient temperature.

TABLE 3

Feed to the second unit of a two-unit anion exchange system

| Component | Concentration (g/L) |
|---|---|
| Sulfuric acid | 0.23 |
| Acetic acid* | 6.57 |
| Xylose | 33.8 |

*Concentration is reported as acetic acid and corresponds to the total concentration of acetic acid and acetate in the feed.

Figure 3:
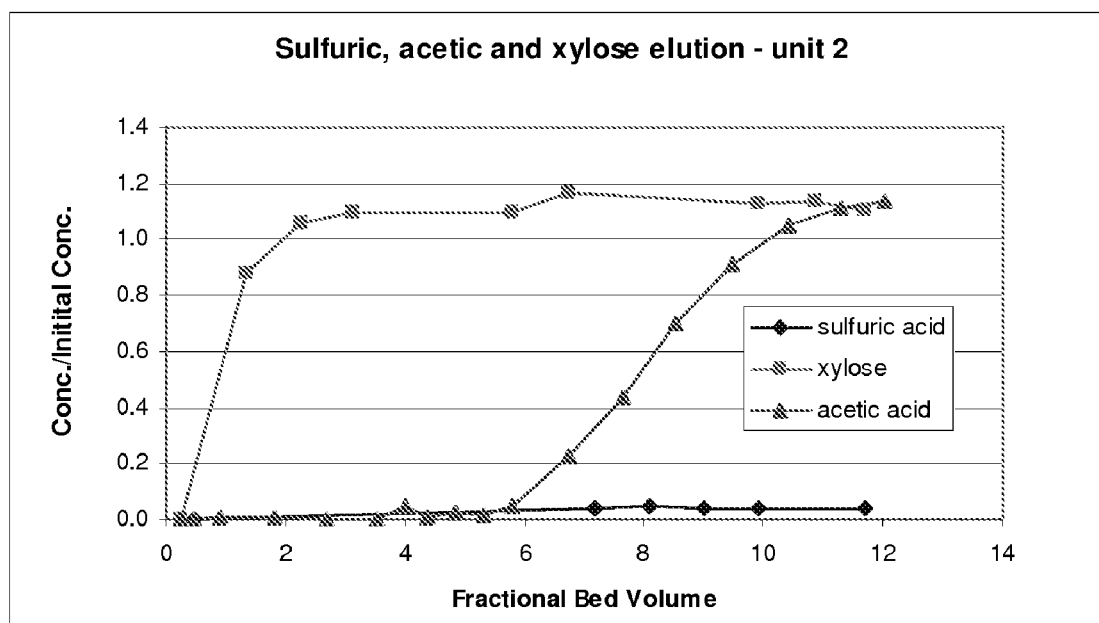
FIG. 3 shows the elution profiles of xylose and acetic acid from a weak base anion exchange column. The column was fed with a stream comprising xylose and acetic acid obtained from processing the aqueous sugar stream from the pretreatment of wheat straw through a first weak base anion exchange column.

The elution profile from the second unit of the anion exchange system is shown in FIG. 3. The acetic acid bound to the column and the 1% breakthrough for acetic acid was reached when approximately 5.9 bed volumes of the sugar stream was fed. The effluent from the column up to 5.9 bed volume comprised xylose and was substantially free of acetic acid. The 1% breakthrough capacity of the resin for acetic acid was calculated to be 0.65 equivalents of acetic acid per litre of resin (Equation 2). Typically in the process of the invention, if the product stream from the second unit comprising sugars were being collected or further processed, feeding to the column would stop at the first detection of acetic acid in the effluent stream. The point at which feeding is stopped can be greater than or less than the 1% breakthrough point. The theoretical capacity for the Marathon WBA resin used is 1.3 equivalents/L of resin.

$$(6.57 \text{ g/L acetic acid})(5.9 \text{ bed volumes})(0.05 \text{ L/bed volume})/(60 \text{ g/equivalent})(0.05 \text{ L bed volume}) = 0.65 \text{ equiv/L resin.} \quad \text{Equation 2}$$

Figure 4:
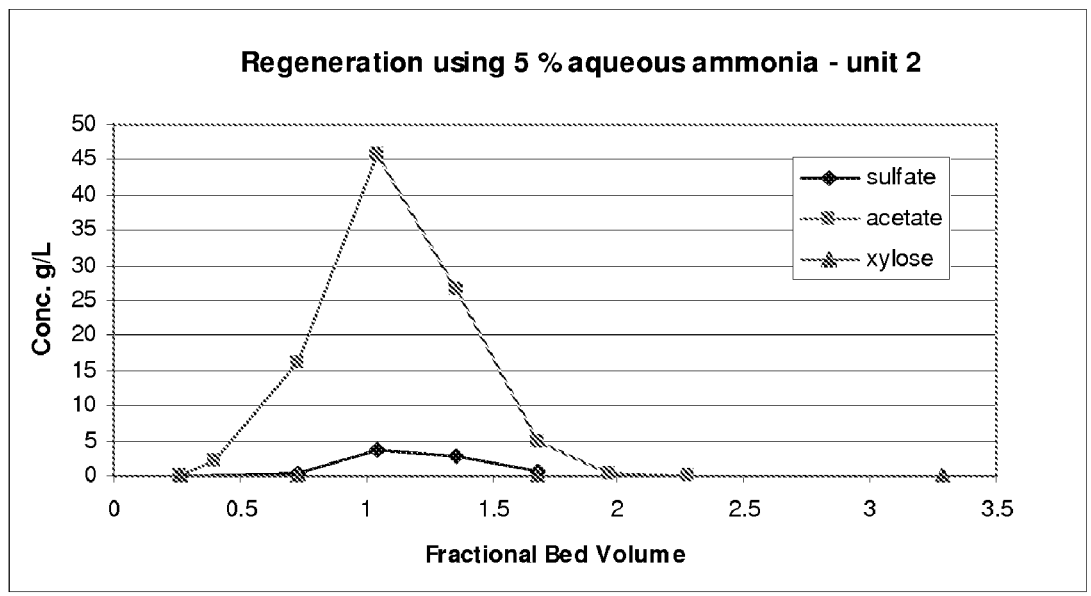
FIG. 4 shows the regeneration profile of a weak base anion exchange column subsequent to feeding 12 bed volumes of an aqueous sugar feed obtained from the pretreatment of wheat straw which had been processed through a first weak base anion exchange column. Aqueous ammonia (5% w/v) was used as the regenerant.

The resin was regenerated with 5% w/v aqueous ammonia which was added at a rate of 5 mL/min. The amount of base used was 1.2 equivalents relative to the amount of acetic acid equivalents bound to the column. After feeding the base, water was used to wash the salt off the column. FIG. 4 shows the amount of acetate obtained in g/L as a function of the fractional bed volume of combined liquid fed to the column. The acetate was substantially removed from the column after 1.9 bed volumes of ammonium hydroxide solution and wash water were fed. Table 4 indicates the concentration and yields of acetate obtainable when sub-portions of the outlet stream are pooled. The regeneration streams contained acetate (as ammonium acetate) at higher concentrations than the combined concentration of acetic acid and acetate in the original streams.

TABLE 4

Concentration and yield of acetate in the outlet stream

| From fbv | To fbv | % Recovery | Concentration (g/L) |
|---|---|---|---|
| 0.7 | 1.0 | 46.6 | 45.9 |
| 0.4 | 1.4 | 91.7 | 29.1 |
| 0.4 | 1.7 | 96.9 | 23.1 |

Example 3

Separation of Sulfuric Acid and Acetic Acid from Xylose in a Two-Unit Anion Exchange System An aqueous sugar stream comprising xylose, sulfuric acid and acetic acid was made from wheat straw by using a steam and sulfuric acid pretreatment as described by Foody (U.S. Pat. No. 4,461,648, which is incorporated herein by reference). The pretreated wheat straw washed with water and the resulting sugar stream comprised the components shown in Table 5. The sugar stream also comprised other organic acids, hexoses and other pentose sugars. The stream had a pH of 1.2.

TABLE 5

Feed to a two-unit anion exchange system

| Component | Concentration (g/L) |
|---|---|
| Sulfuric acid | 18.62 |
| Acetic acid | 9.81 |
| Xylose | 50.25 |

Figure 5:
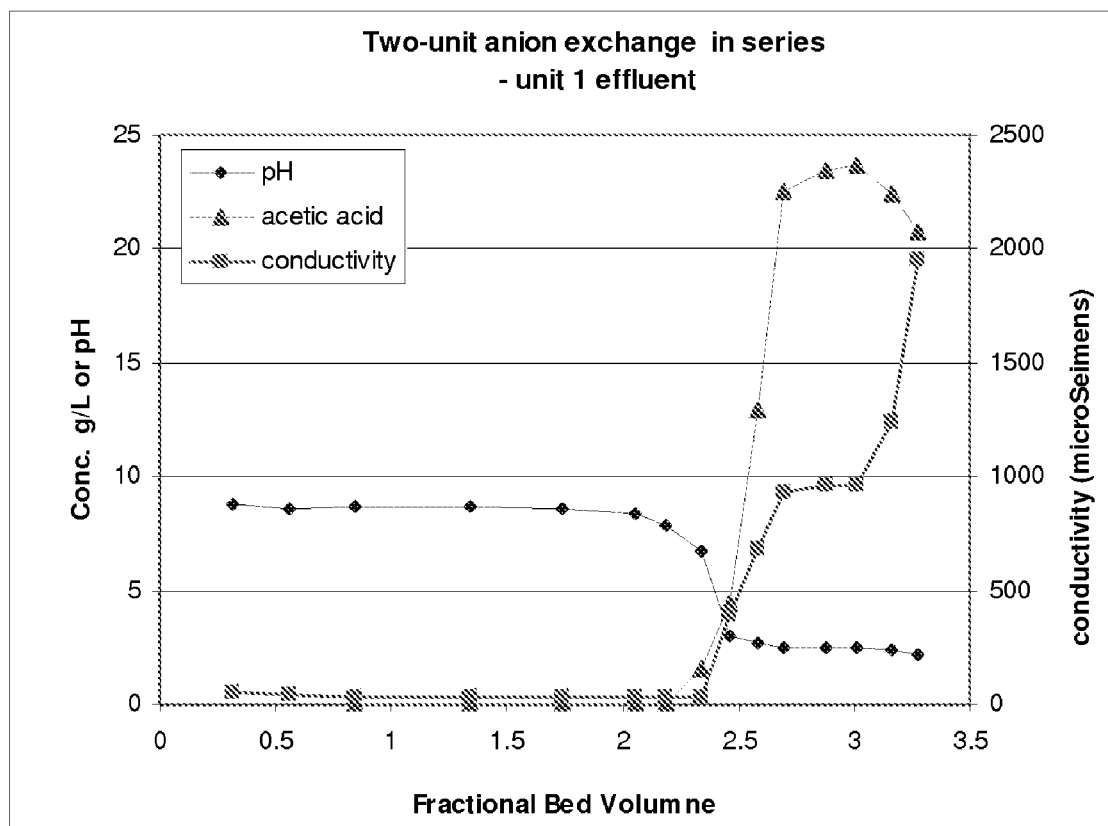
FIG. 5 shows the conductivity, pH and acetic acid elution profiles from a first weak base anion exchange column.

The stream was fed to the first unit of a two-unit anion exchange system prepared as described in Example 1. The effluent from the first unit was allowed to feed directly onto the second unit without first collecting in fractions or pooling the effluent from the first unit. The second unit was prepared as described in Example 2. The stream was fed at a rate of 5.0 mL/minute through the columns and samples of 10-13 mL were collected at the second column exit. Small aliquots were removed from the first column effluent to monitor conductivity and pH and to measure xylose, acetic and sulfuric acid. The results of the first column effluent monitoring are shown in FIG. 5. Conductivity rose to around 1000 μS when acetic acid entered the effluent stream then rose again when sulfuric acid began to enter the effluent stream. The pH decreased as acetic acid entered the effluent stream and then decreased further when sulfuric acid began to enter the effluent stream. Feeding continued until the second conductivity increase was detected. This took place after 3.28 bed volumes of feed had passed through the first column. After the two-unit anion exchange system, the sugar stream was substantially free of sulfuric and acetic acid. The fractions collected from the second column effluent comprised xylose, acetic and sulfuric acid as provided in Table 6. Where indicated, (<0.05) the acids could not be detected above the limit of detection using the HPLC procedure described above.

TABLE 6

Composition of fractions from the second column

| Fractional bed volume (L of feed/L of resin bed) | Xylose (g/L) | Acetic acid (g/L) | Sulfuric acid (g/L) |
|---|---|---|---|
| 2.17 | 50.54 | <0.05 | <0.05 |
| 3.93 | 51.53 | <0.05 | <0.05 |
| 5.44 | 51.60 | 0.01 | <0.05 |

Figure 6:
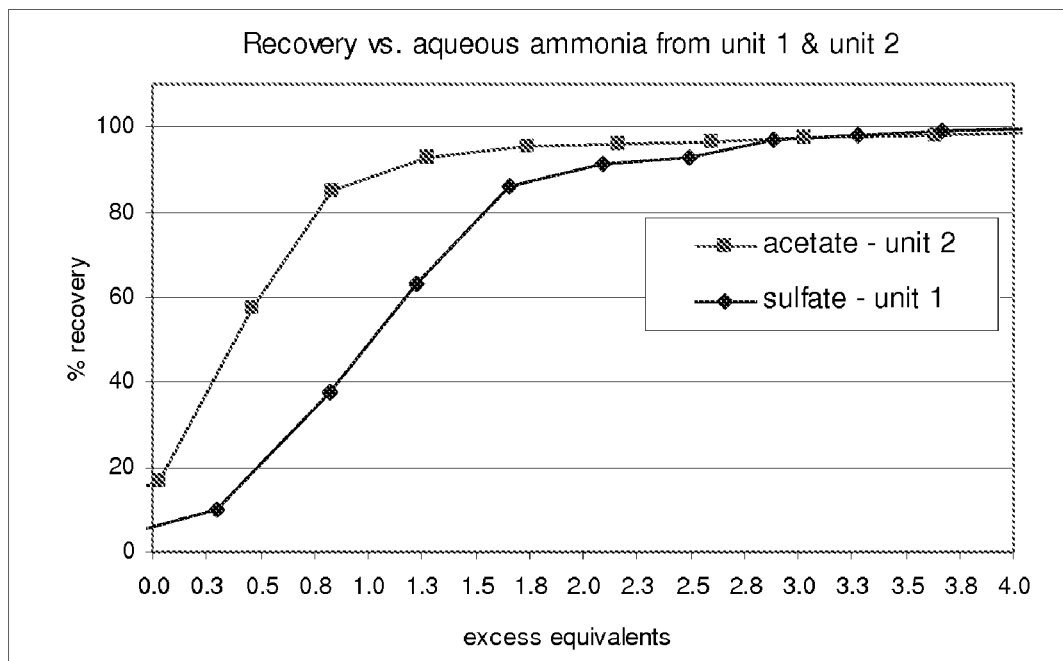
FIG. 6 shows the regeneration profile for the first and second weak base anion exchange columns subsequent to the feeding of 7.32 bed volumes of feed directly through a two-unit anion exchange system. The bound sulfuric and acetic acids are recovered as the organic salts using aqueous ammonia as a regenerant.

After the feeding of 3.28 bed volumes of feed stream (based on first column), the columns were separated and washed with one bed volume of water. Each column was then regenerated with 7% w/v aqueous ammonia, which was fed at a rate of 5 mL/min. FIG. 6 shows that the majority (>97%) of bound acetic acid can be recovered from the second column as ammonium acetate when 2.6 excess equivalents of aqueous ammonia are used (excess equivalents are calculated by dividing the number of equivalents of used aqueous ammonia by the theoretical capacity of the resin (capacity=1.3 equivalents/L of resin for MARATHON WBA)). The majority (>97%) of bound sulfuric acid can be recovered from the first column as ammonium sulfate when 3.0 excess equivalents of aqueous ammonia are used.

Example 4

Regeneration of Bound Acetic Acid with Aqueous Regenerants

An aqueous stream comprising acetic acid was prepared by diluting glacial acetic acid in deionized water. The aqueous stream comprised 11.64 g/L acetic acid. The aqueous stream was fed to a resin bed comprising the weak base anion exchange resin, Purolite® A103S. Purolite® A103S comprises a tertiary amine functional group and a stryrene-divinylbenzene macroporous polymer matrix. The typical particle size of this resin is 650-900 microns. One hundred millilitres (100 mL) of prepared resin was used in a d=1.2 cm glass column. The resin was first prepared by soaking in 85% methanol for 15 minutes, rinsing with water, conditioning with three bed volumes of a 7% w/v aqueous ammonia followed by a rinsing with water. Pre-washing with ammonia or a stronger base such as sodium hydroxide ensures that all tertiary amine functional groups in a weak base resin are available to bind acids and removes the small proportion of anions that can be bound to weak base anion exchange resins on functional groups other than the major tertiary amine group functionality.

Figure 7:
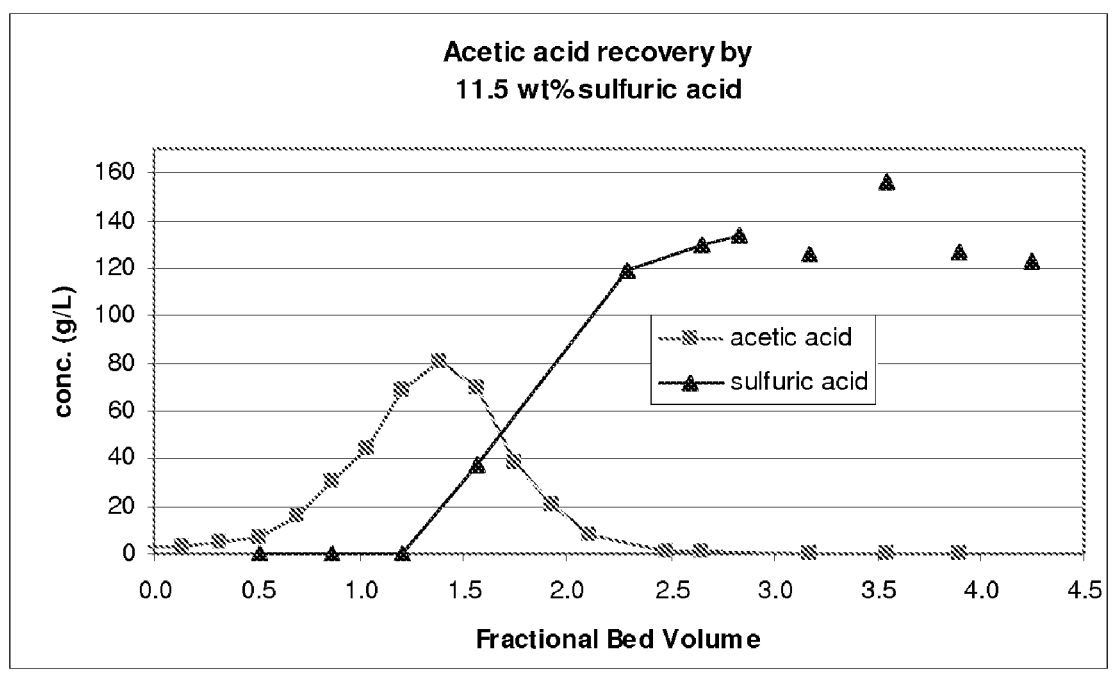
FIG. 7 shows the regeneration profile of a weak base anion exchange column subsequent to feeding an aqueous stream comprising acetic acid up to the 1% breakthrough point. Sulfuric acid (11.5 wt %) was used as the regenerant.

The aqueous stream comprising acetic acid was fed at a rate of 5.0 mL/minute until just prior to acetic 1% breakthrough (1.21 eq/L of resin). The 1% breakthrough capacity of this resin for acetic acid had been previously measured to be about 1.24 eq/L. The liquid held up in the resin bed was removed by rinsing with de-ionized water. In this example, one bed volume of wash water was used. Following the rinsing, a separate 11.5 wt % sulfuric acid solution was used to desorb the bound acetic acid from the resin bed. The product stream comprising acetic acid was collected in fractions for analysis. FIG. 7 shows the amount of acetic acid obtained in g/L as a function of the fractional bed volume of combined regeneration liquid fed to the column. Table 7 indicates the concentration and yields of bound acetic acid obtainable when sub-portions of the outlet stream are pooled. The product stream contained acetic acid at higher concentrations than in the original feed stream. The resin-bound mineral acid can be displaced using an additional aqueous regenerant such as, for example, aqueous ammonia as outlined in Example 1 and 3.

TABLE 7

Concentration and yield of acetic acid in the outlet stream

| From fbv | To fbv | Volume (mL) | % Recovery | Concentration (g/L) |
|---|---|---|---|---|
| 0.86 | 2.11 | 124.3 | 79.9 | 81.9 |
| 0.51 | 2.11 | 160.1 | 91.0 | 93.3 |
| 0.0 | 2.11 | 210.8 | 32.7 | 97.1 |

Example 5

Separation of Sulfuric Acid and Acetic Acid in a Single Anion Exchange Unit

An aqueous stream comprising xylose, sulfuric acid, and acetic acid was made from pure chemicals by dissolving the chemicals in deionized water.

TABLE 8

Feed to a single anion exchange unit

| Component | Concentration (g/L) |
|---|---|
| Sulfuric acid | 7.56 |
| Acetic acid | 8.27 |
| Xylose | 47.7 |

The aqueous stream was fed to a resin bed comprising the weak base anion exchange resin Dowex Marathon WBA. One hundred millilitres (100 mL) of prepared resin was used in a d=1.2 cm glass column. The resin was first prepared by treatment with 5-10 bed volumes of 7% w/v aqueous ammonia followed by rinsing with water.

The aqueous stream was fed at a rate of 6-7 mL/minute until just prior to acetic 1% breakthrough (1.03 eq/L of resin). The liquid held up in the resin bed was removed by rinsing with de-ionized water. In this example, one bed volume of wash water was used. Following the rinsing, a separate 9.1 mL pulse of 7% aqueous ammonia was added to the top of the bed followed by a "water push" that was followed by one bed volume of water wash through the column. This amount of aqueous ammonia was sufficient to completely release acetic acid and insufficient for complete release of sulfuric acid. An additional bed volume of water was added after this to ensure all of the liquid held up in the bed during the regeneration step had eluted. Finally, a second regeneration step was performed using one full bed volume of 7% aqueous ammonia. This excess amount of aqueous ammonia was sufficient for complete release of sulfuric acid. The resin effluent during all of the feeding, washing, and regeneration steps was collected in fractions for analysis. These fractions were analyzed for sulfate, ammonium, acetate, and/or xylose content.

Figure 8A:
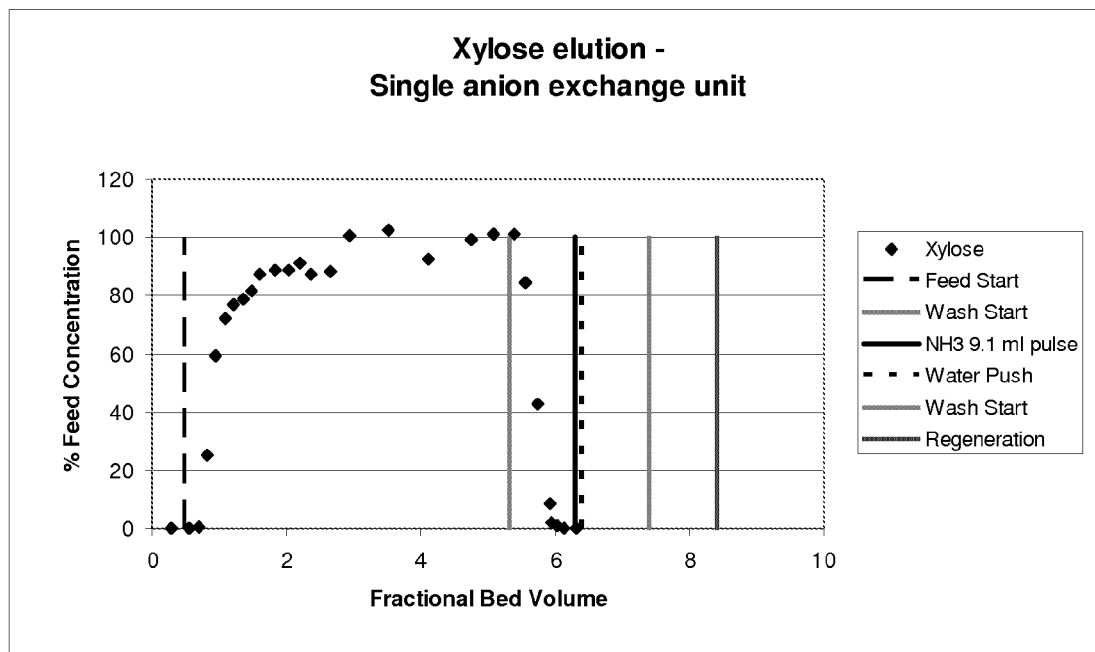
FIGS. 8A and 8B show the separation of sulfuric acid, acetic acid and xylose in a single anion exchange unit.

The elution profile for xylose is shown in FIG. 8A. The xylose eluted from the bed almost immediately after the void volume exited the column and elutes at about its feed concentration between about 2 and 5 fractional bed volumes. Shortly after the feeding is stopped, any residual xylose is completely removed from the bed with the first water wash.

Figure 8B:
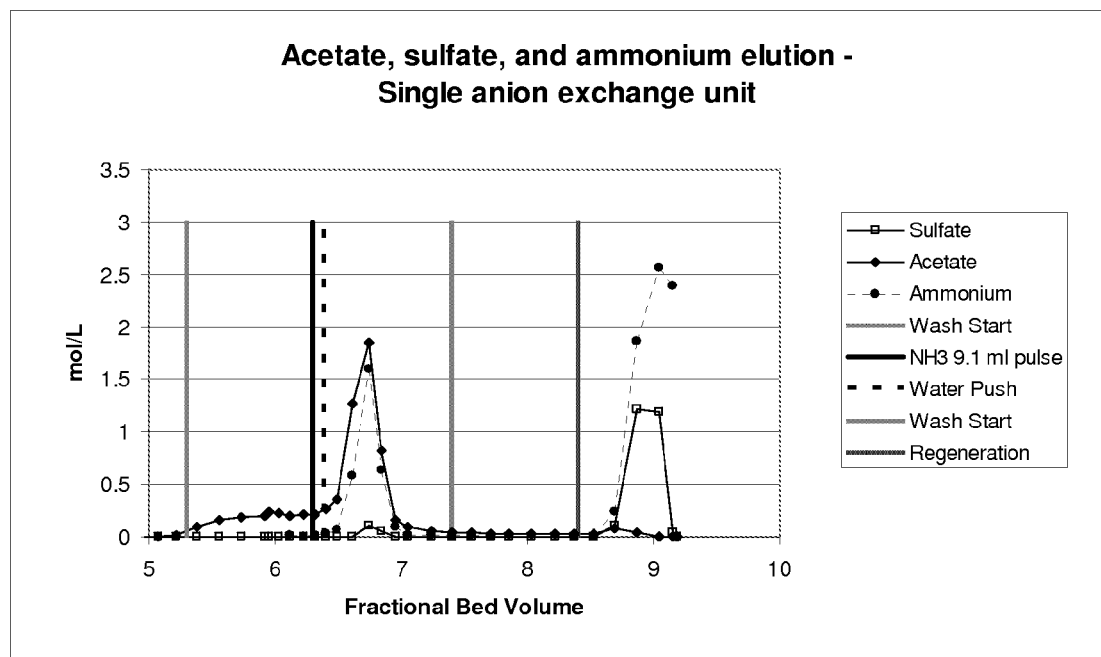

The regeneration profiles for acetic acid and sulfuric acid are shown in FIG. 8B. Shortly after the first ammonia aliquot is fed to the column, acetate and ammonium elute from the column at the same time, starting at about 6.5 bed volumes. This indicates the formation of ammonium acetate, which can be collected in discrete fractions. All of the ammonium acetate is collected during the water push. The ammonium and acetate elute in about a 1:1 molar ratio, which confirms the formation of ammonium acetate. Very little sulfuric acid is removed from the column during the first regeneration step.

Shortly after the bed is regenerated a second time with aqueous ammonia, sulfate and ammonium elute from the column at the same time, starting at about 8.5 bed volumes. This indicates the formation of ammonium sulfate, which can be collected in discrete fractions. All of the sulfate can be collected during this second regeneration step as ammonium sulfate. The ammonium and sulfate elute in about a 2:1 molar ratio, which confirms the formation of ammonium sulfate.

Example 6

Separation of Acetic Acid from Xylose in the Second Unit of a Two-Unit Anion Exchange System Comprising a Strong Base Anion Exchange Resin An aqueous stream comprising xylose and acetic acid was prepared from pure chemicals by dissolving the chemicals in deionized water (Table 9).

TABLE 9

Feed to the second unit of a two-unit anion exchange system

| Component | Concentration (g/L) |
|---|---|
| Acetic acid | 6.6 |
| Xylose | 49.48 |

The aqueous stream was fed to the second unit of an anion exchange system comprising the strong base anion exchange resin LEWATIT MonoPlus™ MP500. This resin comprises a quaternary amine functional group and a styrene-divinylbenzene macroporous matrix. The mean particle size of the resin is 600 microns. One hundred millilitres (100 mL) of prepared resin was used in a d=1.2 cm glass column. The resin was first prepared by rinsing with water and conditioning with 2 L of a 8.3 wt % sodium hydroxide at 5 mL/min to ensure that all the quaternary amine functional groups were in the hydroxide form. The resin is supplied from the manufacturer in the Cl⁻ form.

Figure 9:
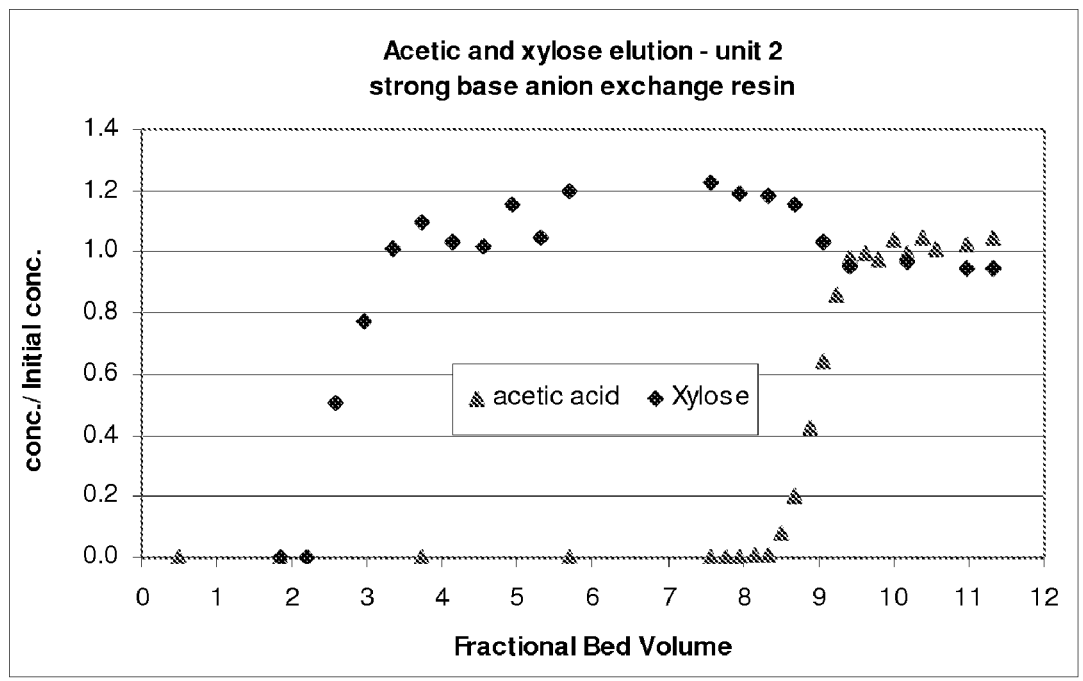
FIG. 9 shows the elution profile for acetic acid and xylose from a strong base anion exchange column.

The aqueous stream was fed at a rate of 5 mL/min until the column was fully saturated with acetate ion. This occurred at 0.99 eq/L of resin. FIG. 9 shows the elution profile for xylose and acetic acid. The 1% breakthrough of xylose occurs after only 2 fractional bed volumes and xylose elutes at approximately feed concentration after only 3 fractional bed volumes. Between 3 and 8.33 fractional bed volumes, xylose elutes while acetate ion is held back by the resin. The acetic acid 1% breakthrough occurs after 8.33 fractional bed volumes (0.89 eq/L of resin) of the aqueous stream have been fed.

Figure 10:
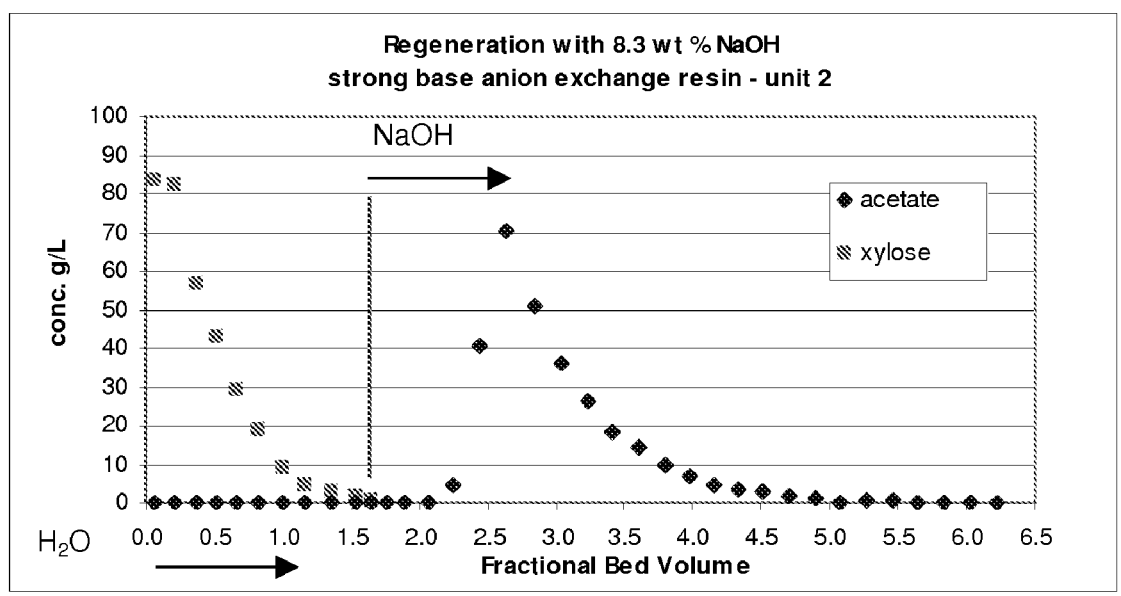
FIG. 10 shows the regeneration profile of a strong base anion exchange column subsequent to feeding an aqueous stream comprising acetic acid and xylose to the 1% breakthrough of acetic acid. After feeding the aqueous stream, the column was first washed with two fractional bed volumes of water then treated with a 8.3 wt % sodium hydroxide solution.
Figure 1:
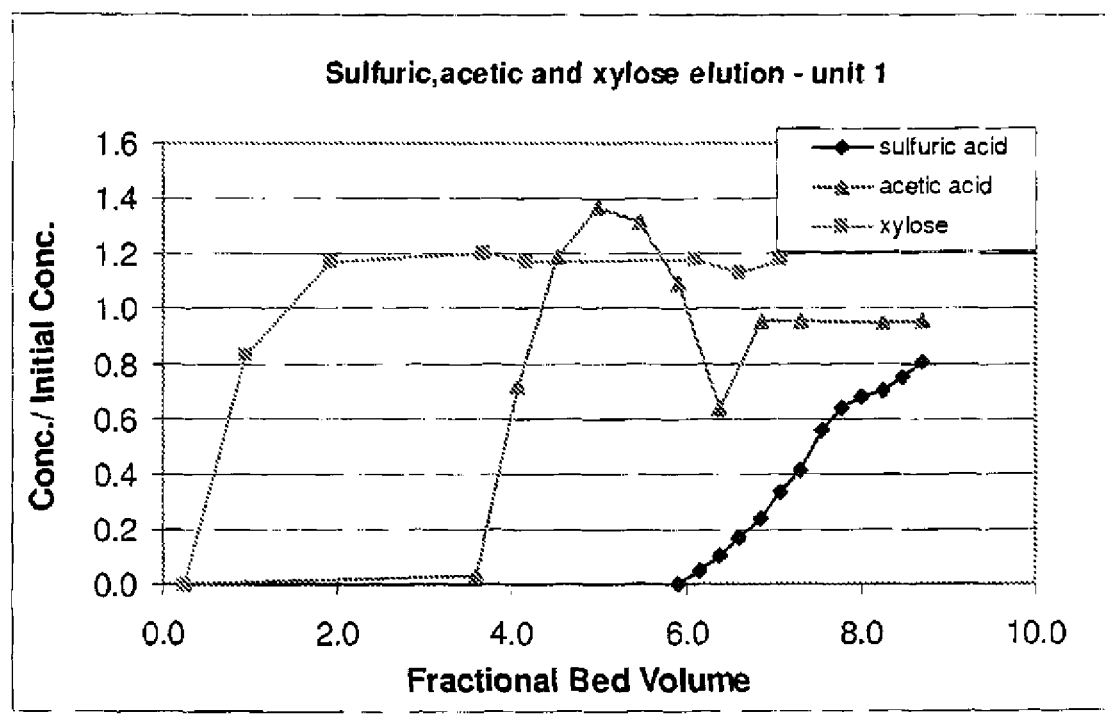
Figure 2:
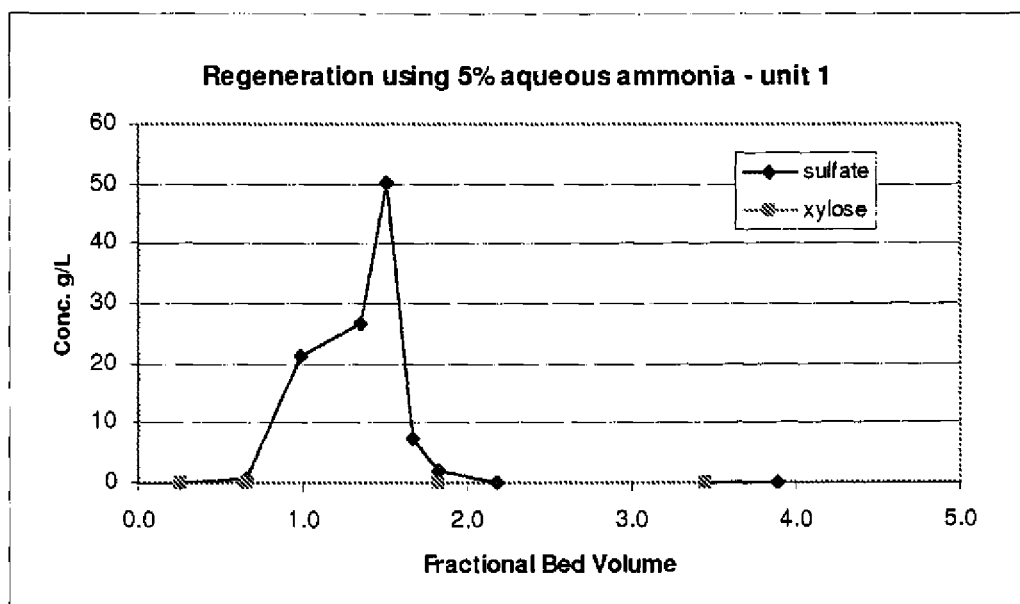
Figure 3:
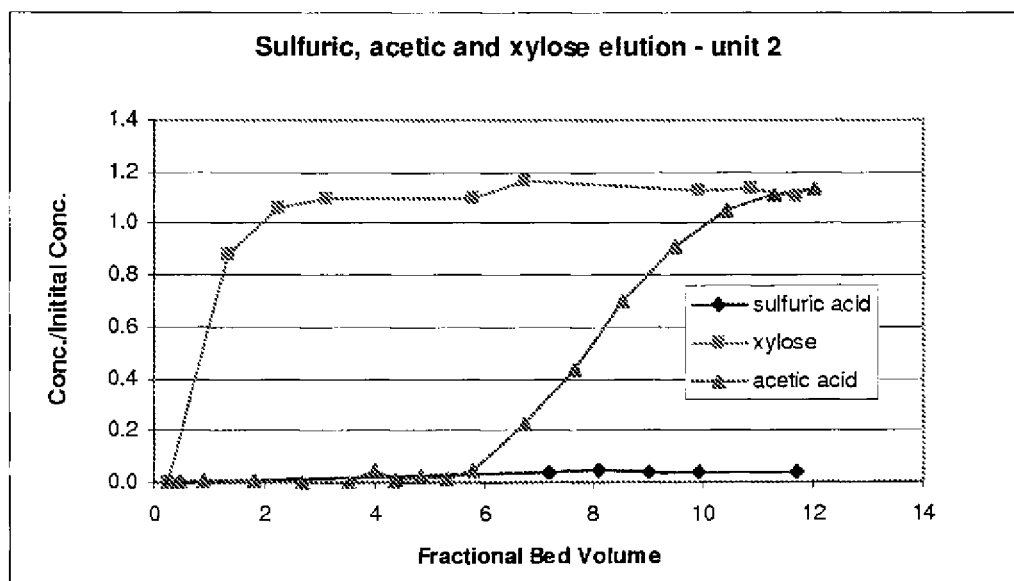
Figure 4:
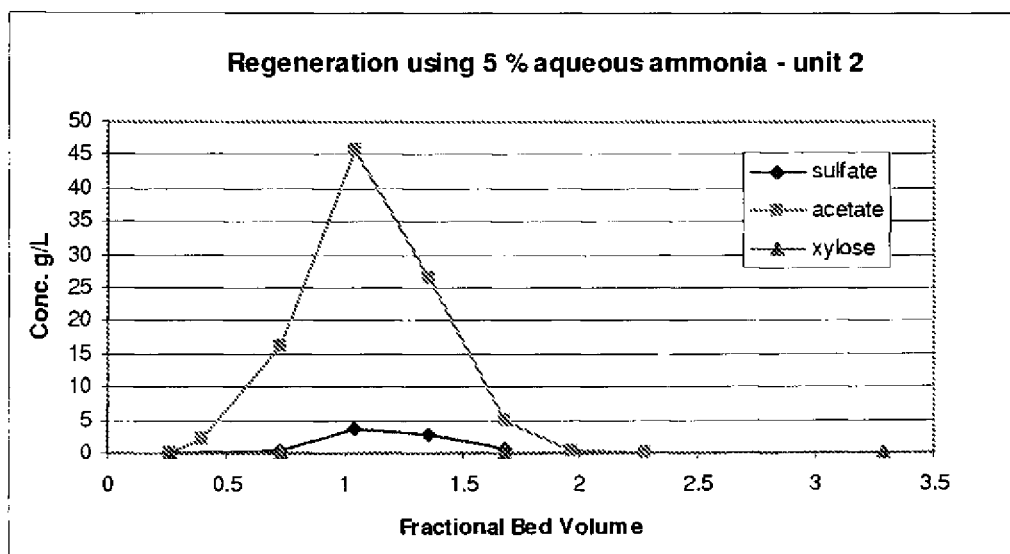
Figure 5:
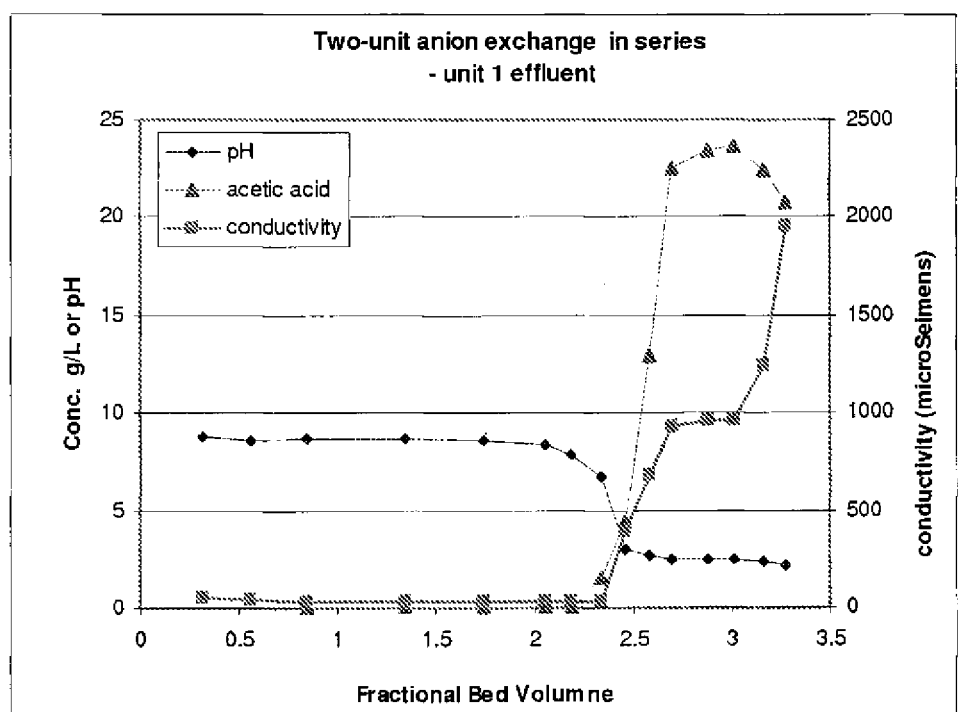
Figure 6:
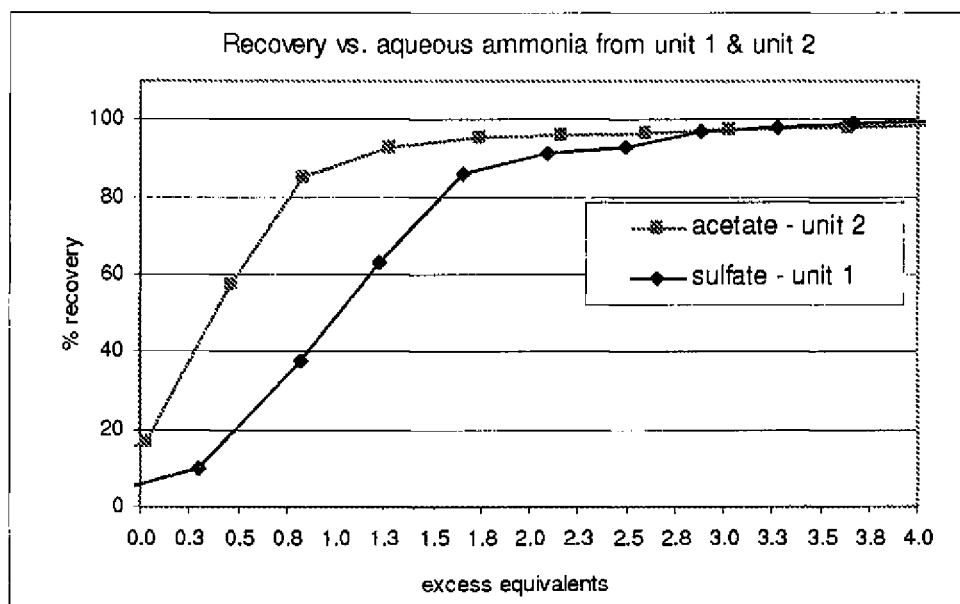
Figure 7:
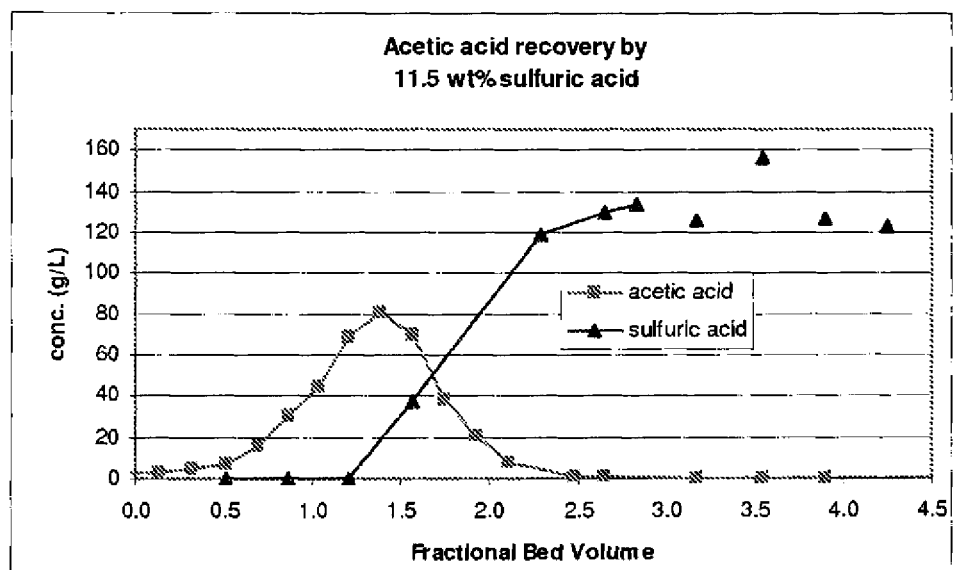
Figure 8A:
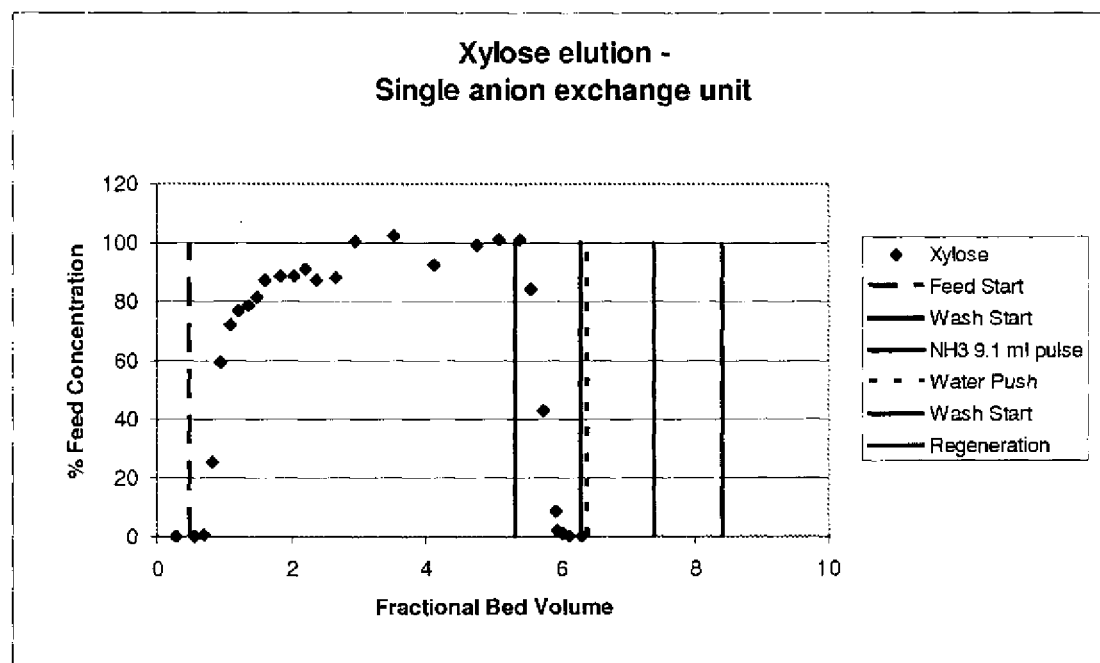
Figure 8B:
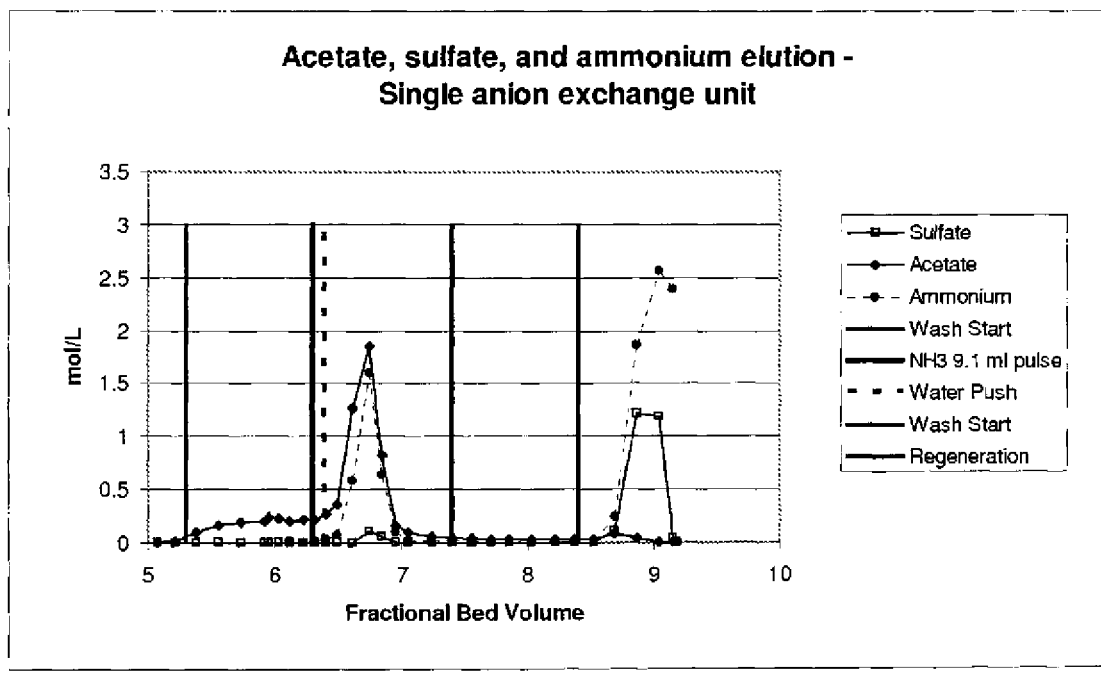
Figure 9:
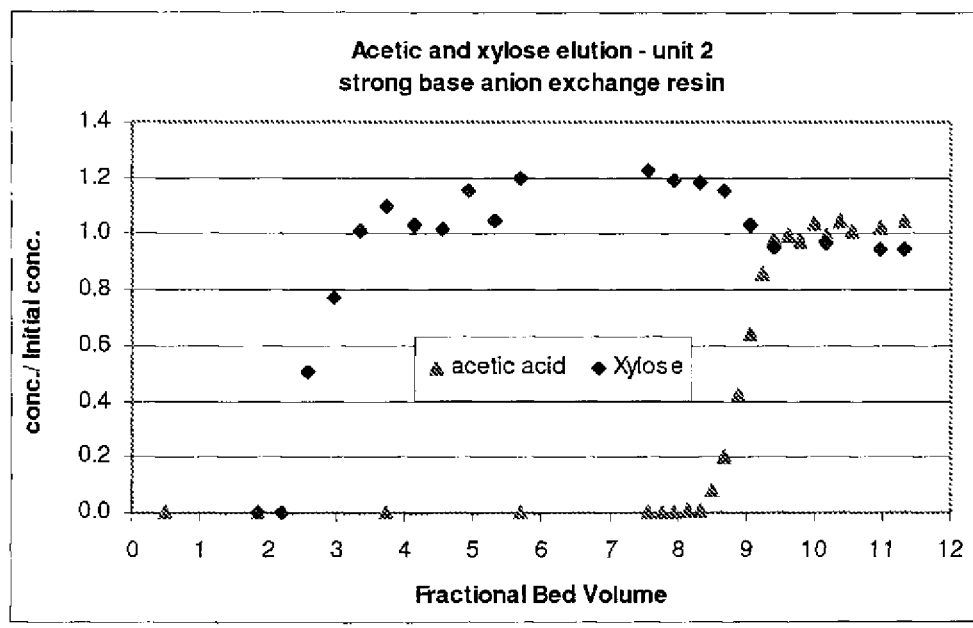
Figure 10:
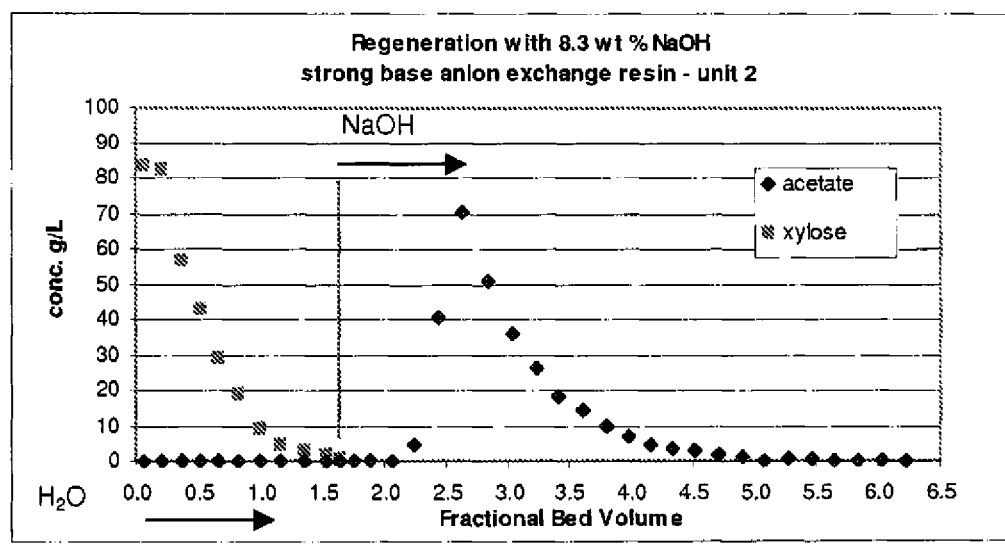

A second column comprising 100 mL of LEWATIT MonoPlus™ MP500 resin was prepared as described above in example 6. The aqueous feed stream described above in Table 9 was fed to the column until the 1% acetic acid breakthrough point. The liquid held up in the resin bed was removed by rinsing with de-ionized water. In this example, two bed volumes of water was used. Following the rinsing, a separate 8.3 wt % sodium hydroxide solution was used to recover the bound acetate from the column. The outlet stream comprising acetate was collected in fractions for analysis. FIG. 10 shows the amount of xylose and acetate obtained in g/L as a function of the fractional bed volume of combined rinse and regeneration liquid fed to the column. In the initial water rinse the void liquid (first ~38 mL or 0.38 fbv) contains some xylose that is un-retained. A small amount (~14%) of very weakly bound xylose elutes with the first 1.2 fbv of rinse water that is fed through the column. Table 10 indicates the concentration and yields of bound acetate obtainable when sub-portions of the outlet stream are pooled. The outlet stream contained acetate at higher concentrations than in the original feed stream.

TABLE 10

Concentration and yield of acetate in the outlet stream from unit 2 of an anion exchange system comprising a strong base anion exchange resin

| From fbv | To fbv | Volume (mL) | % Recovery | Concentration (g/L) |
|---|---|---|---|---|
| 2.08 | 4.33 | 225 | 99.9 | 24.62 |
| 2.25 | 4.15 | 190 | 97.2 | 28.8 |
| 2.25 | 3.61 | 136 | 90.4 | 36.9 |

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A process for obtaining one or more than one organic salt or organic acid from an aqueous sugar stream comprising one or more than one mineral acid, one or more than one organic acid, and a sugar selected from the group consisting of xylose, glucose, arabinose, galactose, mannose and a combination thereof, said process comprising:
  (i) introducing the aqueous sugar stream to a first anion exchange unit comprising one or more than one bed comprising an anion exchange resin, wherein the mineral acid, an anion of the mineral acid, or a combination thereof, binds to the resin;
  (ii) producing an effluent stream comprising the sugar and the organic acid from the first anion exchange unit and regenerating the anion exchange resin with one or more regenerants, thereby producing one or more outlet streams comprising the mineral acid, a salt of the mineral acid or a combination thereof;
  (iii) feeding the effluent stream comprising the sugar and the organic acid to a second anion exchange unit comprising one or more than one bed comprising an anion exchange resin, wherein the organic acid or an anion of the organic acid binds to the resin;
  (iv) obtaining a stream from the second anion exchange unit comprising the sugar, which stream is substantially free of the mineral acid and the organic acid and regenerating the second anion exchange unit with one or more regenerants, thereby producing one or more product streams comprising a salt of the organic acid, the organic acid or a combination thereof; and
  (v) recovering the one or more product streams, wherein the organic acid is selected from the group consisting of acetic acid, formic acid, glucuronic acid, galacturonic acid and a combination thereof and the mineral acid is selected from the group consisting of sulfuric acid, hydrochloric acid, sulfurous acid, phosphoric acid and a combination thereof.

2. The process according to claim 1, further comprising a step of recovering the mineral acid, the salt of the mineral acid or a combination thereof.

3. The process according to claim 1, wherein, in the step of feeding (step (iii)), at least about 70% of the organic acid present in the aqueous sugar stream is fed to the second anion exchange unit.

4. The process according to claim 1, wherein the anion exchange resin in the first anion exchange unit, the second anion exchange unit or both the first and the second anion exchange unit comprises a weak base anion exchange resin.

5. The process according to claim 4, wherein the anion exchange resin in both the first and the second anion exchange unit comprises a weak base anion exchange resin.

6. The process according to claim 1, wherein the anion exchange resin in the first anion exchange unit, the second anion exchange unit or both the first and the second anion exchange unit comprises a strong base anion exchange resin.

7. The process according to claim 1, wherein the mineral acid is sulfuric acid.

8. The process according to claim 1, wherein the organic acid is acetic acid.

9. The process according to claim 1, wherein the one or more regenerants in step (ii), step (iv) or both step (ii) and step (iv) is an alkali solution selected from the group consisting of an ammonium hydroxide solution, a sodium hydroxide solution and a potassium hydroxide solution.

10. The process according to claim 9, wherein the alkali solution is an ammonium hydroxide solution.

11. The process according to claim 1, wherein the first anion exchange unit, the second anion exchange unit or both the first anion exchange unit and the second anion exchange unit is a Simulated Moving Bed (SMB) system or an Improved Simulated Moving Bed (ISMB) system.

12. The process according to claim 1, wherein the organic acid is acetic acid and further comprising recovering the acetic acid from the one or more product streams by distillation.

13. The process according to claim 1, wherein the organic acid is acetic acid and further comprising recovering the acetic acid from the one or more product streams by liquid-liquid extraction.

14. The process according to claim 1, wherein the organic acid is acetic acid and further comprising recovering the acetic acid from the one or more product streams by stripping the acetic acid with air or steam.

15. The process according to claim 12, 13 or 14, wherein the one or more product streams comprise a salt of acetic acid and further comprising adjusting the pH of the one or more product streams to about 4 or lower by the addition of a second acid prior to recovering the acetic acid.

16. The process according to claim 1, wherein the aqueous sugar stream is at a pH of about 0.4 to about 5.0.

17. The process according to claim 1, wherein the aqueous sugar stream is obtained by pretreating a lignocellulosic feedstock at a pH of about 0.4 to about 5.0 by adding one or more than one acid to the lignocellulosic feedstock to hydrolyze at least a portion of the hemicellulose in the feedstock.

18. The process according to claim 1, wherein the aqueous sugar stream is a hydrolyzate stream obtained from adding one or more than one acid to a lignocellulosic feedstock to hydrolyze both hemicellulose and cellulose present in said lignocellulosic feedstock to their respective sugar monomers.

19. The process according to claim 1, wherein one or more regenerants in either or both of step (ii) and (iv) is an aqueous solution independently selected from the group consisting of an alkali solution, an acid solution and water.

20. The process according to claim 19, wherein one or more regenerants in either or both step (ii) and (iv) is an aqueous solution independently selected from the group consisting of an alkali solution and an acid solution.

21. A process for obtaining an organic salt or organic acid from an aqueous sugar stream comprising a mineral acid, an organic acid, and a sugar selected from the group consisting of xylose, glucose, arabinose, galactose, mannose and a combination thereof, said process comprising the steps of:
(i) introducing the aqueous sugar stream to a separation system comprising one or more beds of anion exchange resin and obtaining at least one stream therefrom comprising the sugar;
(ii) regenerating the one or more beds of anion exchange resin in one or more stages, thereby producing at least one stream comprising the mineral acid, a salt of the mineral acid, or a combination thereof, and at least one separate product stream comprising the organic acid, a salt of the organic acid, or a combination thereof; and
(iii) recovering the at least one product stream, wherein the organic acid is selected from the group consisting of acetic acid, formic acid, glucuronic acid, galacturonic acid and a combination thereof and the mineral acid is selected from the group consisting of sulfuric acid, hydrochloric acid, sulfurous acid, phosphoric acid and a combination thereof,
wherein steps (i) and (ii) are carried out by anion exchange.

22. The process of claim 21, wherein the anion exchange system comprises a first and a second anion exchange unit.

23. The process of claim 22, wherein said step of introducing comprises feeding the aqueous sugar stream to the first anion exchange unit, wherein the mineral acid, an anion of the mineral acid, or a combination thereof, binds to the resin of the first anion exchange unit;
said process further comprising obtaining an effluent stream comprising the sugar and the organic acid, a salt of the organic acid, or a combination thereof, from said first anion exchange unit and then feeding the effluent stream to the second anion exchange unit and said organic acid, an anion of the organic acid, or a combination thereof, binds to the resin of the second anion exchange unit; and wherein
said step of regenerating comprises adding at least one regenerant to the first anion exchange unit to produce the at least one stream comprising the mineral acid, a salt of the mineral acid, or a combination thereof, and adding at least one regenerant to the second anion exchange unit to produce the at least one product stream comprising the organic acid, a salt of the organic acid, or a combination thereof.

24. The process of claim 23, wherein at least about 70% of the organic acid present in the aqueous sugar stream is fed to the second anion exchange unit.

25. The process of claim 21, wherein steps (i)-(iii) are carried out in a single anion exchange unit.

26. The process of claim 23, wherein in said step of introducing, the mineral acid, organic acid, or anions thereof, bind to the resin.

27. The process according to claim 21, further comprising a step of recovering the mineral acid, a salt of the mineral acid, or a combination thereof.

28. The process according to claim 21, wherein the separation system comprises a weak base anion exchange resin.

29. The process according to claim 21, wherein the separation system comprises a strong base anion exchange resin.

30. The process according to claim 21, wherein the mineral acid is sulfuric acid.

31. The process according to claim 21, wherein the organic acid is acetic acid.

32. The process according to claim 23, wherein the organic acid is acetic acid.

33. The process according to claim 23, wherein the regeneration comprises adding one or more regenerants to the one or more resin bed to regenerate the anion exchange resin, and the one or more regenerants is an aqueous solution selected from the group consisting of an alkali solution, an acid solution, water and a combination thereof.

34. The process according to claim 33, wherein the one or more regenerants is an aqueous solution selected from the group consisting of an alkali solution, an acid solution and a combination thereof.

35. The process according to claim 34, wherein the alkali solution is selected from the group consisting of an ammonium hydroxide solution, a sodium hydroxide solution, a potassium hydroxide solution, and a combination thereof.

36. The process according to claim 35, wherein the alkali solution is an ammonium hydroxide solution.

37. The process according to claim 21, wherein the separation system is a Simulated Moving Bed System or an Improved Simulated Moving Bed system.

38. The process according to claim 31, further comprising recovering the acetic acid from the at least one product stream by distillation.

39. The process according to claim 31, further comprising recovering the acetic acid from the at least one product stream by liquid-liquid extraction.

40. The process according to claim 31, further comprising recovering the acetic acid from the at least one product stream by stripping the acetic acid with air or steam.

41. The process according to claim 38, 39 or 40, wherein the at least one product stream comprises a salt of acetic acid and further comprising adjusting the pH of the at least one product stream to about 4 or lower by the addition of an acid prior to recovering the acetic acid.

42. The process according to claim 21, wherein the aqueous sugar stream is at a pH of about 0.4 to about 5.0.

43. The process according to claim 21, wherein the aqueous sugar stream is a hydrolyzate stream resulting from pretreating a lignocellulosic feedstock at a pH of about 0.4 to about 5.0, to hydrolyze at least a portion of hemicellulose present in the feedstock.

44. The process according to claim 21, wherein the aqueous sugar stream is a hydrolyzate stream resulting from adding an acid to a lignocellulosic feedstock, to hydrolyze both hemicellulose and cellulose present in said lignocellulosic feedstock to their respective sugar monomers.

45. A process for obtaining acetate salt, acetic acid or a combination thereof, from a lignocellulosic feedstock, comprising the steps of:
(i) obtaining an aqueous sugar stream resulting from hydrolysis of the lignocellulosic feedstock, said hydrolysis comprising one or more stages of sulfuric acid addition, said sugar stream comprising acetic acid, acetate salt, or a combination thereof, sulfuric acid and one or more sugars selected from xylose, glucose, arabinose, galactose, mannose and a combination thereof;
(ii) introducing the aqueous sugar stream to a Simulated Moving Bed separation system comprising one or more beds of anion exchange resin and obtaining at least one stream therefrom comprising the one or more sugars;
(iii) regenerating the one or more beds of anion exchange resin with sulfuric acid, thereby producing at least one organic acid product stream comprising the acetic acid and, thereafter, regenerating the one or more beds of anion exchange resin with ammonium hydroxide to produce at least one separate outlet stream comprising ammonium sulfate; and (iv) recovering the at least one product stream.

46. The process according to claim 45, wherein the sulfuric acid addition is conducted to pretreat the lignocellulosic feedstock, thereby hydrolyzing at least a portion of hemicellulose present in said lignocellulosic feedstock to sugar monomers.

47. The process according to claim 45, wherein the sulfuric acid addition is conducted to hydrolyze both hemicellulose and cellulose present in said lignocellulosic feedstock to their respective sugar monomers.

* * * * *

UNITED STATES PATENT AND TRADEMARK OFFICE
CERTIFICATE OF CORRECTION

PATENT NO. : 7,718,070 B2  
APPLICATION NO. : 11/774113  
DATED : May 18, 2010  
INVENTOR(S) : Wahnon Page 1 of 28

It is certified that error appears in the above-identified patent and that said Letters Patent is hereby corrected as shown below:

Please delete patent 7718070 in its entirety and insert patent 7718070 in its entirety as shown on the attached pages.

Signed and Sealed this
Thirteenth Day of January, 2015

Michelle K. Lee
*Deputy Director of the United States Patent and Trademark Office*

(12) United States Patent
Wahnon

(10) Patent No.: US 7,718,070 B2
(45) Date of Patent: May 18, 2010

(54) METHOD OF OBTAINING AN ORGANIC SALT OR ACID FROM AN AQUEOUS SUGAR STREAM

(75) Inventor: Daphne Wahnon, Ottawa (CA)

(73) Assignee: Iogen Energy Corporation, Ontario (CA)

(*) Notice: Subject to any disclaimer, the term of this patent is extended or adjusted under 35 U.S.C. 154(b) by 277 days.

(21) Appl. No.: 11/774,113

(22) Filed: Jul. 6, 2007

(65) Prior Publication Data
US 2008/0041366 A1 Feb. 21, 2008

Related U.S. Application Data

(60) Provisional application No. 60/822,783, filed on Aug. 18, 2006.

(51) Int. Cl.
*B01J 49/00* (2006.01)
*C02F 1/42* (2006.01)
*B01D 15/04* (2006.01)
*B01D 15/00* (2006.01)
*C13J 1/06* (2006.01)
*C13J 1/02* (2006.01)
*C13D 3/16* (2006.01)

(52) U.S. Cl. ........ 210/670; 210/638; 210/660; 210/661; 210/673; 210/674; 127/46.2; 127/46.3; 127/50; 127/51

(58) Field of Classification Search
USPC ............... 210/638, 660, 661, 670, 673, 674; 127/43, 46.2, 46.3, 50, 51
See application file for complete search history.

(56) References Cited

U.S. PATENT DOCUMENTS

| 4,102,705 A | 7/1978 | Pfeiffer et al. |
| 4,237,110 A * | 12/1980 | Forster et al. ............ 423/488 |

(Continued)

FOREIGN PATENT DOCUMENTS

| CA | 2 479 248 | 9/2003 |
| EP | 0 106 466 | 4/1984 |

(Continued)

OTHER PUBLICATIONS

Wooley et al. A Nine-Zone Simulating Moving Bed for the Recovery of Gulcose and Xylose from Biomass Hydrolyzate. Ind. Eng. Chem. Res. 1998, 37, p. 3699-3709.*

(Continued)

*Primary Examiner* — Karl E Group
*Assistant Examiner* — Noah S Wiese
(74) *Attorney, Agent, or Firm* — Fitzpatrick, Cella, Harper & Scinto

(57) ABSTRACT

A process for obtaining one or more than one salt of an organic acid(s), or organic acid(s), from an aqueous sugar stream comprising one or more than one mineral acid and the organic acid(s) is provided. The process comprises introducing the aqueous sugar stream to a separation system comprising one or more beds of anion exchange resin and obtaining a stream therefrom comprising the sugar. The one or more beds of anion exchange resin are then regenerated in one or more stages to produce at least one product stream comprising the organic acid, a salt of the organic acid, or a combination thereof, and a separate outlet stream comprising the mineral acid, a salt of the mineral acid, or a combination thereof. The product stream is then recovered. The separation may be conducted with two separation units, or using a single anion exchange unit.

47 Claims, 11 Drawing Sheets

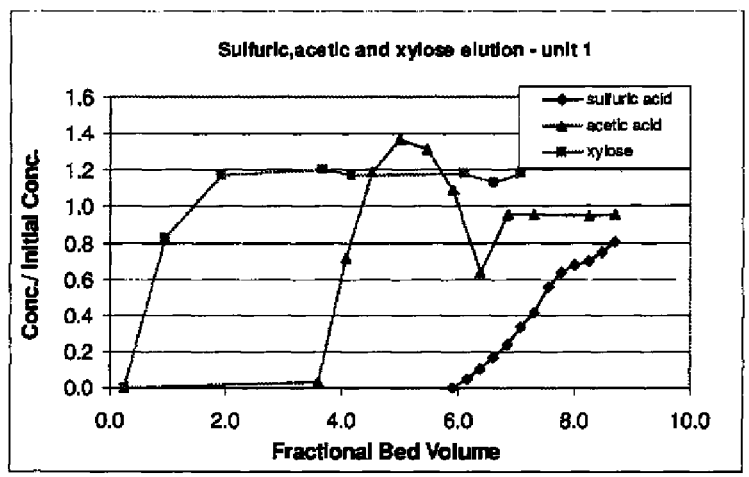

(56) References Cited

U.S. PATENT DOCUMENTS

| | | | |
|---|---|---|---|
| 4,461,648 A | | 7/1984 | Foody et al. |
| 4,818,409 A | | 4/1989 | Puetter et al. |
| 4,851,573 A | | 7/1989 | Kulprathipangja et al. |
| 4,968,353 A | * | 11/1990 | Kawasaki et al. ............ 127/46.2 |
| 5,175,357 A | * | 12/1992 | Van Brunt ..................... 562/513 |
| 5,434,255 A | * | 7/1995 | Katayama et al. ............ 536/117 |
| 5,789,210 A | | 8/1998 | Ho et al. |
| 6,419,828 B1 | * | 7/2002 | Russo, Jr. ..................... 210/635 |
| 6,451,123 B1 | | 9/2002 | Saska et al. |
| 2004/0231661 A1 | * | 11/2004 | Griffin et al. .................... 127/1 |
| 2005/0244934 A1 | * | 11/2005 | Foody et al. .................. 435/101 |

FOREIGN PATENT DOCUMENTS

| | | |
|---|---|---|
| JP | 1-127049 | 5/1989 |
| WO | WO 03/095627 | 11/2003 |
| WO | WO 2006/007691 | 1/2006 |

OTHER PUBLICATIONS

Anderson, et al., "Sulfate-Bisulfate Equilibrium on Anion Exchange Resins", Industrial and Engineering Chemistry, vol. 47, No. 8 (1955) 1620-23.

Wooley, et al., "Lignocellulosic Biomass to Ethanol Process Design and Economics Utilizing . . . ", NREL (National Renewable Energy Laboratory), (1999) 16-17.

Wooley, et al., "A Nine-Zone Simulating Moving Bed for the Recovery of Glucose and Xylose from Biomass Hydrolyzate", Ind. Eng. Chem. Res., vol. 37 (1998), 3699-709.

Barrier, et al., "Acid hydrolysis with corn stover at TVA's experimental Plant" (1985).

Barrier, et al., "Integrated Fuel Alcohol Production Systems for Agriculture Feedstocks, Phase III", Quarterly Technical Report for the period Apr.-Jun. 1985.

* cited by examiner

METHOD OF OBTAINING AN ORGANIC SALT OR ACID FROM AN AQUEOUS SUGAR STREAM

CROSS REFERENCE TO RELATED APPLICATIONS

This application claims priority to, and the benefit of, U.S. Provisional Patent Application Ser. No. 60/822,783, filed Aug. 18, 2006, which is hereby incorporated by reference in its entirety.

BACKGROUND OF THE INVENTION

1. Field of the Invention

The present invention provides a process for obtaining one or more than one organic salt or organic acid from an aqueous sugar stream. More particularly, the invention relates to a process for obtaining one or more than one organic salt or organic acid from an aqueous sugar stream comprising one or more than one mineral acid and a sugar(s).

2. Related Art

Fuel ethanol is currently produced from feedstocks such as corn starch, sugar cane, and sugar beets. However, the potential for production of ethanol from these sources is limited as most of the farmland which is suitable for the production of these crops is already in use as a food source for humans. Furthermore, the production of ethanol from these feedstocks has a negative impact on the environment because fossil fuels used in the conversion process produce carbon dioxide and other byproducts.

The production of ethanol from cellulose-containing feedstocks, such as agricultural wastes, grasses, and forestry wastes, has received much attention in recent years. The reasons for this are that these feedstocks are widely available and inexpensive and their use for ethanol production provides an alternative to burning or landfilling lignocellulosic waste materials. Moreover, a byproduct of cellulose conversion, lignin, can be used as a fuel to power the process instead of fossil fuels. Several studies have concluded that, when the entire production and consumption cycle is taken into account, the use of ethanol produced from cellulose generates close to nil greenhouse gases.

The lignocellulosic feedstocks that are the most promising for ethanol production include (1) agricultural wastes such as corn stover, wheat straw, barley straw, oat straw, rice straw, canola straw, and soybean stover; (2) grasses such as switch grass, miscanthus, cord grass, and reed canary grass; and (3) forestry wastes such as aspen wood and sawdust.

The three primary constituents of lignocellulosic feedstocks are cellulose, which comprises 30% to 50% of most of the key feedstocks; hemicellulose, which comprises 15% to 35% of most feedstocks, and lignin, which comprises 15% to 30% of most feedstocks. Cellulose and hemicellulose are comprised primarily of carbohydrates and are the source of sugars that can potentially be fermented to ethanol. Lignin is a phenylpropane lattice that is not converted to ethanol.

Cellulose is a polymer of glucose with beta-1,4 linkages and this structure is common among the feedstocks of interest. Hemicellulose has a more complex structure that varies among the feedstocks. For the feedstocks of interest, the hemicellulose typically consists of a backbone polymer of xylose with beta-1,4 linkages, with side chains of 1 to 5 arabinose units with alpha-1,3 linkages, or acetyl moieties, or other organic acid moieties such as glucuronyl groups.

The first process step for converting lignocellulosic feedstock to ethanol involves breaking down the fibrous material. The two primary processes are acid hydrolysis, which involves the hydrolysis of the feedstock using a single step of acid treatment, and enzymatic hydrolysis, which involves an acid pretreatment followed by hydrolysis with cellulase enzymes.

In the acid hydrolysis process, the feedstock is subjected to steam and a mineral acid, such as sulfuric acid, hydrochloric acid, or phosphoric acid. The temperature, acid concentration and duration of the hydrolysis are sufficient to hydrolyze the cellulose and hemicellulose to their monomeric constituents, which is glucose from cellulose and xylose, galactose, mannose, arabinose, acetic acid, galacturonic acid, and glucuronic acid from hemicellulose. Sulfuric acid is the most common mineral acid for this process. The sulfuric acid can be concentrated (25-80% w/w) or dilute (3-8% w/w). The resulting aqueous slurry contains unhydrolyzed fiber that is primarily lignin, and an aqueous solution of glucose, xylose, organic acids, including primarily acetic acid, but also glucuronic acid, formic acid, lactic acid and galacturonic acid, and the mineral acid. The aqueous solution is separated from the fiber solids to produce a sugar hydrolyzate stream.

In the enzymatic hydrolysis process, the steam temperature, mineral acid (typically sulfuric acid) concentration and treatment time of the acid pretreatment step are chosen to be milder than that in the acid hydrolysis process. Similar to the acid hydrolysis process, the hemicellulose is hydrolyzed to xylose, galactose, mannose, arabinose, acetic acid, glucuronic acid, formic acid and galacturonic acid. However, the milder pretreatment does not hydrolyze a large portion of the cellulose, but rather increases the cellulose surface area as the fibrous feedstock is converted to a muddy texture. The pretreated cellulose is then hydrolyzed to glucose in a subsequent step that uses cellulase enzymes. Prior to the addition of enzyme, the pH of the acidic feedstock is adjusted to a value that is suitable for the enzymatic hydrolysis reaction. Typically, this involves the addition of alkali to a pH of between about 4 and about 6, which is the optimal pH range for cellulases, although the pH can be higher if alkalophilic cellulases are used.

In one type of pretreatment process, the pressure produced by the steam is brought down rapidly with explosive decompression, which is known as steam explosion. Foody, (U.S. Pat. No. 4,461,648) describes the equipment and conditions used in steam explosion pretreatment. Steam explosion with sulfuric acid added at a pH of 0.4 to 2.0 has been the standard pretreatment process for two decades. It produces pretreated material that is uniform and requires less cellulase enzyme to hydrolyze cellulose than other pretreatment processes.

Regardless of whether acid hydrolysis or enzymatic hydrolysis is carried out, the resulting aqueous hydrolyzate stream is likely to contain glucose, xylose, arabinose, galactose, mannose, and organic acids, such as acetic acid, glucuronic acid, formic acid and galacturonic acid and the mineral acid, such as sulfuric acid. However, it will be appreciated that salts of the mineral acid and organic acid may be present and that the fraction of these acids in the salt form will increase with increasing pH. The glucose in this stream can be readily fermented to ethanol by conventional yeast or to butanol by bacteria. The pentose sugars can be fermented to ethanol by recombinant yeast (see U.S. Pat. No. 5,789,210 (Ho et al.) and WO 03/095627 (Boles and Becker)) or bacteria. Alternatively, the pentose sugars may be used as starting materials for the generation of other high value products using chemical, microbial or enzymatic means or simply recovered. For example, xylitol may be produced by the fermentation or hydrogenation of xylose or the xylose may be simply recovered.

The presence of the organic acid and mineral acid, or the corresponding salts, in a hydrolyzate stream decrease the efficiency of processes for converting glucose or other sugars to ethanol or other valuable products. In particular, during any neutralization conducted prior to enzymatic hydrolysis or fermentation (both of which take place at moderate pH values such as at pH values of about 4.0 to about 6.0), these compounds will consume alkali, such as sodium hydroxide, ammonium hydroxide, or potassium hydroxide. In addition, the mineral acids and organic acids, and their salts, may be inhibitory to yeast, bacteria and, to a lesser extent, cellulase enzymes. Any such inhibition can decrease the efficiency of the fermentation and enzymatic hydrolysis operations by lengthening the time required for carrying out the fermentation or enzyme hydrolysis, increasing the amount of yeast or enzyme catalyst required and/or decreasing the final yields. It therefore may be desirable to remove these compounds from the hydrolyzate to produce a clean sugar stream. In addition it may also be advantageous to remove these compounds from sugar streams obtained from other than hydrolysis, depending on the circumstances.

Pfeiffer (U.S. Pat. No. 4,102,705) discloses the deacidification of xylose streams by the removal of acetic acid and the mineral acids of sulfuric, hydrochloric, or nitric acid by using a two-stage ion exchange process. Pfeiffer feeds the aqueous stream to the first anion exchange system to bind the mineral acid and allow xylose and acetic acid to pass through. The resin is regenerated with sodium hydroxide, thereby producing sodium chloride, sodium sulfate, or sodium nitrate salt. The stream containing xylose and acetic acid is evaporated to remove 90% of the acetic acid. The resulting xylose stream with the remaining acetic acid is fed to a second ion exchange system, which binds the acetic acid and allows the deacidified xylose stream to pass through. The ion exchange resin is regenerated with sodium hydroxide to generate sodium acetate salt.

The evaporation taught by Pfeiffer would be very extensive in order to remove 90% of the acetic acid from the aqueous stream. Acetic acid is less volatile than water, so this evaporation would dewater the stream almost to dryness. It is very difficult to carry out such an evaporation as the presence of precipitated solids leads to scale deposition and fouling of heat exchange surfaces.

Wooley et al. (In Lignocellulosic Biomass to Ethanol Process Design and Economics Utilizing Co-Current Dilute Acid Prehydrolysis and Enzyme Hydrolysis Current and Future Scenarios, (1999) Technical Report, National Renewable Energy Laboratory pp. 16-17), reports removing 88% of the acetic acid and 100% of the sulfuric acid from a sugar hydrolyzate stream by using a continuous ion exchange separations unit. The ion exchange media is a weak base anion exchange resin and the resin is regenerated with ammonia. The acetic acid and sulfuric acid are discharged from the unit in the same stream and disposed of in a wastewater treatment unit.

WO 2006/007691 (Foody and Tolan) discloses the use of ion exclusion chromatography at pH 5.0 to 10.0 to separate ammonium acetate and ammonium sulfate salts from sugar streams prior to fermentation of the sugar. This separation method relies on the use of a cation exchange resin in the ammonium form.

Wooley et al., (Ind. Eng. Chem. Res., 1998, 37:3699-3709) discloses the use of ion exclusion chromatography with cation exchange resins in the hydronium form to separate acetic acid and sulfuric acid from sugar hydrolyzate streams. In this process, sulfuric acid is excluded from the resin and passes through the resin first while the non-ionic sugars move more slowly through the resin. The feed streams are at pH 3.0 and below, and the resulting process separates the stream into sulfuric acid, sugar, and acetic acid streams. However, control and recovery of the three product streams in the process would be difficult and costly.

Anderson et al. (Ind. Eng. Chem., 1955, 47:1620-1623) discloses the use of strong base anion exchange resins as a means of separating a strong mineral acid from water soluble organic material. In this process, the strong base anion exchange resin is first converted to the sulfate form. The mineral acid is retained by the resin bed and the water soluble organic material passes through the resin bed and is not bound. The method is useful for binding and recovering strong acids such as sulfuric and hydrochloric acids and relies on the absence of a significant interaction between the water soluble organic material and the resin bed. As long as the sulfate form of the resin is available, the mineral acid will bind the resin. However, the process does not result in the separation of an organic acid or its salt from an aqueous sugar stream.

Barrier et al. (Integrated Fuel Alcohol Production Systems for Agricultural Feedstocks, Phase III, Quarterly Technical Report for the Period April-June 1995. Submitted by Tennessee Valley Authority Office of Agricultural and Chemical Development, TVA Contract No. TV-540881, 1985) discloses the use of anion exchange resins, including weak base anion exchange resins, to recover sulfuric acid from a hydrolyzate stream. The method is useful for the recovery of sulfuric acid but results in a mixed sugar-organic acid stream. The mixed sugar-organic acid stream is sent directly to a yeast fermentation to produce ethanol. Caustic is added to adjust the fermentation pH and yeast media components are also added. The ethanol containing solution is subsequently distilled to produce a fuel ethanol. However, there is no disclosure of recovery of the organic acid which is understood to remain in the still bottoms after ethanol distillation and is not recovered.

Therefore, there is not a satisfactory process for recovering organic acids, or their corresponding salts, from aqueous sugar streams. The ability to remove organic acids, or their salts, from sugar streams remains a critical requirement to improve the efficiency of converting sugar to ethanol or other valuable products.

SUMMARY OF THE INVENTION

The present invention provides a process for obtaining one or more than one organic salt or organic acid from an aqueous sugar stream. More particularly, the invention relates to a process for obtaining one or more than one organic salt or organic acid from an aqueous sugar stream comprising one or more than one mineral acid and a sugar.

It is an object of the present invention to provide an improved method of obtaining an organic acid or salt from an aqueous sugar stream.

According to a first aspect of the invention, there is provided a process (A) for obtaining an organic salt or organic acid from an aqueous sugar stream comprising a mineral acid, an organic acid, and a sugar selected from the group consisting of xylose, glucose, arabinose, galactose, mannose and a combination thereof, said process comprising the steps of:

(i) introducing the aqueous sugar stream to a separation system comprising one or more beds of anion exchange resin and obtaining at least one stream therefrom comprising the sugar;

(ii) regenerating the one or more beds of anion exchange resin in one or more stages, thereby producing at least one stream comprising the mineral acid, a salt of the mineral acid, or a combination thereof, and at least one separate product stream comprising the organic acid, a salt of the organic acid, or a combination thereof; and (iii) recovering the at least one product stream.

According to this aspect of the invention, the anion exchange separation system may comprise separate first and second anion exchange units as described below. Alternatively, steps (i)-(iii) may be carried out in a single anion exchange unit comprising at least one resin bed. When the separation is carried out in a single anion exchange unit, the mineral acid, organic acid, and/or anions of these acids, bind to the resin bed(s) of the unit and the resin bed(s) is subsequently regenerated to displace the bound species.

According to a second aspect of the invention, there is provided a process (B) for obtaining one or more than one organic salt or organic acid from an aqueous sugar stream comprising one or more than one mineral acid, the one or more than one organic acid, and a sugar selected from the group consisting of xylose, glucose, arabinose, galactose, mannose and a combination thereof, said process comprising:

(i) introducing the aqueous sugar stream to a first anion exchange unit comprising one or more than one bed comprising an anion exchange resin, wherein the mineral acid, an anion of the mineral acid or a combination thereof binds to the resin;

(ii) producing an effluent stream comprising the sugar and the organic acid from the first anion exchange unit and regenerating the anion exchange resin with one or more regenerants, thereby producing one or more outlet streams comprising the mineral acid, a salt of the mineral acid or a combination thereof;

(iii) feeding the effluent stream comprising the sugar and the organic acid to a second anion exchange unit comprising one or more than one bed comprising an anion exchange resin, wherein the organic acid or an anion of the organic acid binds to the resin;

(iv) obtaining a stream from the second anion exchange unit comprising the sugar, which stream is substantially free of the mineral acid and the organic acid and regenerating the second anion exchange unit with one or more regenerants, thereby producing one or more product streams comprising a salt of the organic acid, the organic acid or a combination thereof; and (v) recovering the one or more product streams.

The present invention also pertains to the process (B) defined above, wherein, in the step of feeding (step (iii)), at least about 70% of the organic acid present in the aqueous stream is fed to the second anion exchange unit.

The anion exchange resin bed in the first anion exchange unit, the second anion exchange unit or both the first and the second anion exchange units may comprise a weak or a strong base anion exchange resin. Preferably, the anion exchange resin is a weak base resin.

The present invention also pertains to the processes (A or B) as defined above which further comprise a step of recovering the salt of the mineral acid, the mineral acid or a combination thereof.

The present invention also pertains to the processes (A or B) as defined above, wherein the mineral acid is selected from the group consisting of sulfuric acid, sulfurous acid, hydrochloric acid, phosphoric acid and a combination thereof. Preferably, the mineral acid is sulfuric acid.

Furthermore, the present invention relates to the processes (A or B) as defined above, wherein the organic acid is selected from the group consisting of acetic acid, formic acid, galacturonic acid, glucuronic acid and a combination thereof. Preferably, the organic acid is acetic acid.

The present invention also relates to the processes (A or B) as defined above, wherein the acetic acid is recovered from the one or more product streams. Acetic acid may be recovered from the product stream by distillation, by liquid-liquid extraction or by stripping with air or steam. In one embodiment of the invention, the one or more product streams comprise a salt of acetic acid and the pH of the product stream(s) is adjusted to 4 or lower by the addition of acid prior to recovering the acetic acid.

The present invention also relates to the processes (A or B) as defined above, wherein the regenerant(s) is an aqueous solution selected from an acid solution, an alkali solution or water. Preferably, the regenerant is an alkali or acid solution. If the regenerant is alkali, it is preferably an alkali solution selected from the group consisting of aqueous ammonia (also referred to as ammonium hydroxide), a sodium hydroxide solution and a potassium hydroxide solution. Most preferably, the base is aqueous ammonia or ammonium hydroxide.

The present invention also relates to the processes (A or B) as defined above, wherein the anion exchange is a Simulated Moving Bed (SMB) system or an Improved Simulated Moving Bed (ISMB) system.

The present invention also relates to the processes (A or B) as defined above, wherein the aqueous sugar stream is obtained by pretreating a lignocellulosic feedstock at a pH of about 0.4 to about 5.0 by adding one or more than one acid to the lignocellulosic feedstock to hydrolyze at least a portion of the hemicellulose in the feedstock. The present invention also relates to the processes (A or B) as defined above, wherein the aqueous sugar stream is at a pH of 0.4 to about 5.0. Alternatively, the aqueous sugar stream is a hydrolyzate stream resulting from adding an acid to a lignocellulosic feedstock to hydrolyze both hemicellulose and cellulose present in said lignocellulosic feedstock to their respective sugar monomers.

According to another aspect of the invention, there is provided a process (C) for obtaining acetate salt, acetic acid or a combination thereof, from a lignocellulosic feedstock comprising the steps of:

(i) obtaining an aqueous sugar stream resulting from hydrolysis of the lignocellulosic feedstock, said hydrolysis comprising one or more stages of sulfuric acid addition, said sugar stream comprising acetic acid, acetate salt, or a combination thereof, sulfuric acid and one or more sugars selected from xylose, glucose, arabinose, galactose, mannose or a combination thereof;

(ii) introducing the aqueous sugar stream to a Simulated Moving Bed separation system comprising one or more beds of anion exchange resin and obtaining at least one product stream therefrom comprising the one or more sugars;

(iii) regenerating the one or more beds of anion exchange resin with sulfuric acid, thereby producing at least one organic acid product stream comprising the acetic acid and thereafter, regenerating the one or more beds of anion exchange resin with ammonium hydroxide to produce at least one separate outlet stream comprising ammonium sulfate; and (iv) recovering the product stream.

The present invention also relates to the process (C) as defined above, wherein the sulfuric acid addition is conducted to pretreat the lignocellulosic feedstock, thereby hydrolyzing at least a portion of hemicellulose present in said lignocellulosic feedstock to sugar monomers. Alternatively, the sulfuric acid addition is conducted to hydrolyze both the hemicellulose and cellulose present in said lignocellulosic feedstock to their respective sugar monomers.

The present invention overcomes the limitations of the prior art. The ion exchange process is suitable for acidic hydrolyzate streams, unlike ion exclusion processes. Moreover, the anion exchange process of the invention typically does not require large amounts of dilution water typical of ion exclusion operations, but rather the mineral and organic salts or their acids can be obtained in their concentrated form. The process of the invention does not depend on the use of evaporation to remove the organic acid, and therefore can avoid this cost. Furthermore, the process of the invention can produce mineral salt and organic salt, or their respective acids, in separate streams at higher concentrations than present in the original feed stream. The separate and concentrated nature of the mineral and organic salt or acid streams facilitates recovery and further processing of these compounds.

The invention therefore represents a significant step forward in the processing of lignocellulosic feedstocks for the production of ethanol or other products.

BRIEF DESCRIPTION OF THE DRAWINGS

These and other features of the invention will become more apparent from the following description in which reference is made to the appended drawings wherein:

FIG. 1 shows the elution profiles of sulfuric acid, acetic acid and xylose from a weak base anion exchange column. The column was fed with an aqueous sugar stream obtained from the pretreatment of wheat straw.

FIG. 2 shows the regeneration profile of the weak base anion exchange column subsequent to feeding 8.7 bed volumes of an aqueous sugar stream obtained from the pretreatment of wheat straw. Aqueous ammonia (5% w/v) was used as the regenerant.

FIG. 3 shows the elution profiles of xylose and acetic acid from a weak base anion exchange column. The column was fed with a stream comprising xylose and acetic acid obtained from processing the aqueous sugar stream from the pretreatment of wheat straw through a first weak base anion exchange column.

FIG. 4 shows the regeneration profile of a weak base anion exchange column subsequent to feeding 12 bed volumes of an aqueous sugar feed obtained from the pretreatment of wheat straw which had been processed through a first weak base anion exchange column. Aqueous ammonia (5% w/v) was used as the regenerant.

FIG. 5 shows the conductivity, pH and acetic acid elution profiles from a first weak base anion exchange column.

FIG. 6 shows the regeneration profile for the first and second weak base anion exchange columns subsequent to the feeding of 7.32 bed volumes of feed directly through a two-unit anion exchange system. The bound sulfuric and acetic acids are recovered as the organic salts using aqueous ammonia as a regenerant.

FIG. 7 shows the regeneration profile of a weak base anion exchange column subsequent to feeding an aqueous stream comprising acetic acid up to the 1% breakthrough point. Sulfuric acid (11.5 wt %) was used as the regenerant.

FIGS. 8A and 8B show the separation of sulfuric acid, acetic acid and xylose in a single anion exchange unit. FIG. 8A shows the xylose elution profile from a weak base anion exchange resin bed subsequent to feeding an aqueous stream comprising xylose, sulfuric acid and acetic acid. The aqueous stream was fed until just prior to 1% breakthrough of acetic acid. FIG. 8B shows the regeneration profiles of acetate, sulfate and ammonium after two regeneration stages, wherein each of the regeneration stages involved the addition of aqueous ammonia.

FIG. 9 shows the elution profile for acetic acid and xylose from a strong base anion exchange column.

FIG. 10 shows the regeneration profile of a strong base anion exchange column subsequent to feeding an aqueous stream comprising acetic acid and xylose to the 1% breakthrough of acetic acid. After feeding the aqueous stream, the column was first washed with two fractional bed volumes of water then treated with a 8.3 wt % sodium hydroxide solution.

DETAILED DESCRIPTION OF THE INVENTION

The present invention provides a process for obtaining one or more than one organic salt or organic acid from an aqueous sugar stream. More particularly, the invention relates to a process for obtaining one or more than one organic salt or organic acid from an aqueous sugar stream comprising one or more than one mineral acid and a sugar monomer, for example, selected from xylose, glucose, arabinose, galactose, mannose or a combination thereof.

The following description is of a preferred embodiment.

The process of the invention involves the use of anion exchange resins to achieve separation of the mineral acid and organic acid from the aqueous sugar stream. This comprises the exchange of anions in the aqueous stream with anions on the resin (strong base anion exchange) or acid adsorption onto the resin (weak base anion exchange), followed by a subsequent regeneration step to displace the bound species. Sugars have low affinity for the resin and elute from the resin first while the mineral acid and organic acid or their anions are retained. The process of the invention is distinguished from ion exclusion chromatographic separation techniques which rely on a different mechanism of separation. Ion exclusion uses ion exchange resins in a form such that the target ionic compounds are excluded from the resin due to charge repulsion. The excluded compounds elute from the column quickly, while uncharged compounds absorb into the resin and elute from the column more slowly.

The aqueous stream may originate from the processing of a lignocellulosic feedstock. Representative lignocellulosic feedstocks are (1) agricultural wastes such as corn stover, wheat straw, barley straw, oat straw, rice straw, canola straw, and soybean stover; (2) grasses such as switch grass, miscanthus, cord grass, and reed canary grass; and (3) forestry wastes such as aspen wood and sawdust. These feedstocks contain high concentrations of cellulose and hemicellulose that are the source of the sugar, including sugar monomers, for example glucose and xylose, in the aqueous stream. However, the practice of the invention is not limited by the feedstock used.

The aqueous sugar stream used in the practice of the invention comprises mineral acid(s), organic acid(s), and sugar(s). Preferably, the aqueous sugar stream is produced by subjecting the feedstock to acid hydrolysis or pretreatment, with the acid used being a mineral acid. The acid hydrolysis or pretreatment processes can be any that are familiar to those of skill in the art. In one embodiment of the invention, the pretreatment is conducted at pH 0.4 to 5.0 to hydrolyze hemicellulose present in the feedstock. For example, the pretreatment may be conducted at 0.4, 0.5, 1.0, 1.5, 2.0, 2.5, 3.0, 3.5, 4.0, 4.5 or 5.0. However, the practice of the invention is not limited to the use of acid hydrolysis or pretreatment, or a specific process used to produce the aqueous sugar stream.

The sugar may include a sugar monomer, for example, a sugar monomer selected from xylose, glucose, arabinose, galactose, mannose or a combination thereof.

The mineral acid preferably arises from an acid hydrolysis or pretreatment process, and is carried into the aqueous sugar stream. Regardless of its source, the mineral acid may be selected from, but is not limited to, sulfuric acid, sulfurous acid, hydrochloric acid, or phosphoric acid. Preferably, the mineral acid is sulfuric acid. Although the sugar stream for use in the invention may comprise hydrochloric acid, this acid suffers from the disadvantage that it introduces chloride ions into solution. Thus, for certain applications, it may be preferred that the aqueous sugar stream does not comprise hydrochloric acid, especially in cases where the metallurgy of the system must be protected from the corrosive effect of this acid.

The organic acids may include acetic acid, galacturonic acid, formic acid, lactic acid, glucuronic acid or a combination thereof. The group of organic acids preferably includes acetic acid. Acetic acid may be generated by acid hydrolysis or pretreatment of the lignocellulosic feedstock. Many lignocellulosic feedstocks contain hemicellulose with acetyl groups attached to xylan. The acid hydrolysis or pretreatment processes liberate acetic acid from the acetyl groups. However, the practice of the invention is not limited to the use of sugar hydrolyzate streams which comprise acetic acid formed by the hydrolysis of acetyl groups.

The aqueous sugar stream may be subjected to cation exchange prior to being fed to an anion exchange separation system. Cation exchange can be employed to remove potassium, calcium, magnesium, sodium, and other cations that are present in the sugar stream. Removal of these cations reduces the likelihood of precipitation of compounds of low solubility, for example calcium hydroxide and calcium sulfate. Removal of the cations can also benefit the subsequent anion exchange.

The aqueous sugar stream is preferably substantially free of undissolved or suspended solids. This may be achieved by filtration, centrifugation, or other processes for removing fiber solids or suspended solids from aqueous streams that are familiar to those skilled in the art. Optionally, the aqueous sugar stream is concentrated, for example, by evaporation or with membranes, or the like. It is also contemplated that a portion of the mineral acid is removed from the aqueous sugar stream prior to feeding it to the anion exchange separation system, for example, by chromatographic separation or other means.

The mineral acid may be present in the aqueous sugar stream at a concentration of about 0.5 g/L to about 100 g/L, or any concentration range therebetween. A more preferred mineral acid concentration is about 1 g/L to about 50 g/L, or any concentration range therebetween.

The organic acids concentration in the aqueous sugar stream may be about 1 g/L to about 60 g/L, or any concentration range therebetween. In a more preferred embodiment, the organic acids concentration is about 2 g/L to about 50 g/L, or any concentration range therebetween. Preferably, the aqueous sugar stream comprises acetic acid and sulfuric acid. The concentration of acetic acid can be less than or greater than sulfuric acid. The ratio of the concentration of acetic acid to that of sulfuric acid may be less than about 4.0:1.0.

The combined concentration of sugars in the aqueous sugar stream may be about 10 g/L to about 250 g/L, or any concentration range therebetween. In a more preferred embodiment, the combined concentration of sugars is 25 g/L to 100 g/L, or any concentration range therebetween. With respect to the glucose and xylose in the aqueous sugar stream, the weight ratio of glucose to xylose may range from 0:100 to 100:0, or any ratio therebetween; for example, the weight ratio of glucose to xylose may be 0:100, 5:95, 10:90, 20:80, 30:70, 40:60, 50:50, 60:40, 70:30, 80:20, 90:10 or 100:0 or any ratio therebetween.

The total solutes concentration in the aqueous sugar stream may be as low as about 20 g/L and as high as about 600 g/L, or any concentration range therebetween. For example, the total solutes concentration may be about 30 g/L to about 400 g/L, or any range therebetween. Preferably, the total solutes concentration is about 40 g/L to about 300 g/L, or any range therebetween.

The aqueous stream is at an acidic pH for effective processing by anion exchange. In a non-limiting example, the aqueous stream is at a pH of 0.4 to about 5.0, or any pH range therebetween, as it is fed to the anion exchange separation system. In this pH range, the pH is approximately equal to, or lower than, the pKa of the organic acids present. For example, the pKa of acetic acid is 4.75. In a more preferred embodiment, the aqueous stream is at a pH of 0.4 to about 4.0, or any pH range therebetween. In a most preferred embodiment, the aqueous stream is at a pH of 0.4 to about 3.0, or any pH range therebetween. For example, the pH may be 0.4, 0.5, 1.0, 1.5, 2.0, 2.5, 3.0, 3.5, 4.0, 4.5 or 5.0, or any pH range therebetween.

The aqueous stream is preferably at a temperature of about 20° C. to about 90° C., or any temperature therebetween. More preferably, the temperature is about 45° C. to about 75° C., or about 55° C. to about 70° C., or any temperature therebetween. For example, the temperature may be 20, 25, 30, 35, 40, 45, 50, 55, 60, 65, 70, 75, 80, 85 or 90° C., or any temperature therebetween.

The aqueous sugar stream may comprise compounds other than the mineral acids, organic acids and sugars. For example, the aqueous sugar stream may comprise other inorganic compounds, including, but not limited to, potassium sulfate, calcium sulfate, magnesium sulfate, or sodium sulfate. The aqueous sugar stream may also contain other organic compounds, including but not limited to, furfural, hydroxymethyl furfural, dissolved lignin, and the like. The concentration of these compounds may be from about 0% to about 75% of the total solutes present in the aqueous stream, or from about 0% to about 50% of the total solutes present in the aqueous sugar stream.

The anion exchange resin may be a weak base anion exchange resin. By a weak base anion exchange resin, it is meant a resin with a polymeric structure comprising a weak base functional group. A common weak base functional group found in weak base anion exchange resins is a tertiary amine. Amines such as trialkyl amines and pyridine are found commonly in weak base anion exchange resins, although it should be appreciated that other functional groups may be used.

Alternatively, the anion exchange resin is a strong base anion exchange resin. By a strong base anion exchange resin, it is meant a resin with a polymeric structure comprising a strong base functional group. A common strong base functional group found in strong base anion exchange resins is a quaternary amine, although it should be appreciated that other functional groups may be used. The strong base anion exchange resin may be a Type I or Type II (Dianion Manual of Ion Exchange Resins and Synthetic Adsorbent, Mitsubishi Chemical Corporation, $2^{nd}$ edition, 1995) strong base anion exchange resin. Type I strong base anion exchange resins comprise a stronger base functional group than Type II resins. Typically, a Type II resin comprises a quartenary ammonium functional group where one of the four nitrogen substituents comprises an aminoethanol group. However, any functional group that renders the quaternary ammonium functional group less basic may be present in Type II strong base anion exchange resins.

A common polymeric structure for a strong or weak base resin is formed using divinyl benzene cross-linked polystyrene; however, any suitable polymer or cross-linking agent known to those skilled in the art can be used. For example, anion exchange resins may also be formed using an acrylic polymeric support. A polymeric backbone can also be formed using various levels of cross-linking agent to control the porosity of the polymeric structure.

The weak base or strong base anion exchange resins may be macroporous, i.e., containing discrete pores, microporous (gel resins) or may contain elements of both these structures. Weak or strong base anion exchange resins may be prepared to contain a narrow range of particle shape and size or a wide range of particle shape and sizes. The total operating capacity of the anion exchange resin may vary depending on the process used to prepare the resin. Furthermore, anion exchange resins can vary depending on the nature of the polymeric structure, supplier, lots, synthesis methods, process parameters, or functional group. This results in resins that differ in certain parameters such as pressure drop, swelling and shrinking, moisture holding capacity, diameter, porosity, thermal stability, physical stability, and the like. However, it is to be understood that the invention is not limited by the specific physical and chemical properties of the resin employed.

Although the use of weak and strong base resins falls within the scope of the invention, weak base resins are preferred over strong base resins for various reasons. A weak base resin typically consumes lower quantities of alkali when regeneration is carried out compared to strong base resins. In addition, weak base resins can be regenerated using a weak base, such as ammonium hydroxide, which can be advantageous for recovering the mineral and organic acids from the regenerated salts. Furthermore, a weak base resin does not increase the pH of the sugar streams in the resin bed to highly alkaline values. Such highly alkaline conditions can cause the degradation of sugars (for example xylose) and the ionization of sugars which can bind to strong base anion exchange resins reducing yields.

In one embodiment of the invention, the process comprises two anion exchange units to achieve separation of the mineral acid and organic acid from the aqueous sugar stream. According to this embodiment, the aqueous sugar stream is fed to the first anion exchange unit comprising a resin bed that binds the mineral acid or its anion. A low-affinity effluent stream is obtained from the first unit that comprises the organic acid(s) and the sugar(s) which, in turn, is fed to the second anion exchange unit. The resin of the first anion exchange unit is then regenerated by an aqueous regenerant, which may be water, to obtain an outlet stream comprising the mineral acid, the mineral salt, or a combination thereof. The resin is preferably regenerated by an alkali, including, but not limited to, ammonium hydroxide, potassium hydroxide, or sodium hydroxide to produce a mineral salt. The mineral salt may be recovered or may be processed and recovered as the mineral acid.

The second anion exchange unit uses an anion exchange resin to bind the organic acid or an anion of the organic acid. Preferably, more than about 70% of the organic acid in the aqueous sugar stream proceeds to the second unit. The stream obtained from the second anion exchange unit is then a stream comprising, but not limited to, a sugar monomer, for example, xylose, glucose, or a combination thereof, that is essentially free of organic acid and mineral acid. The resin is subsequently regenerated with an aqueous regenerant, which may be water, to obtain a product stream comprising the organic acid, the organic salt, or a combination thereof. In one embodiment, the resin is regenerated by an alkali, including, but not limited to, ammonium hydroxide, potassium hydroxide, or sodium hydroxide to produce an organic salt. The organic salt may then be recovered or is processed and recovered as the organic acid.

The anion exchange resin(s) are typically packed in vertical columns, horizontal beds, or a combination thereof. The first and/or the second anion exchange units may comprise multiple beds which are arranged in parallel, in series, or may include a combination of beds arranged in series and in parallel. However, the practice of the invention is not limited by the arrangement of beds. As would be apparent to one of skill in the art, in either case, the volume of the resin bed is typically chosen based on the flow rate and the concentration of acids or anions in the aqueous stream. The sizing of resin beds may be carried out by combining the data from laboratory, or other experiments, on the aqueous sugar stream with design principles that are familiar to those skilled in the art.

The mineral acid, or its anion, binds to the resin since it has the highest affinity for the resin of the major compounds present. Without wishing to be bound by theory, if a strong base anion exchange resin is used, the anion of the mineral acid will bind to the resin and if a weak base anion exchange resin is used, the mineral acid will bind to the resin. The sugars and most other inorganic and organic compounds have limited affinity for the resin and pass through the resin bed. The organic acids have an intermediate level of affinity for the resin and bind to the resin initially, but are displaced by the mineral acid and desorb. The effluent stream from the resin bed of the first anion exchange unit comprising the sugar and organic acids may be fed directly to the second anion exchange unit, or may be collected and pooled, and subsequently fed to the second anion exchange unit.

Preferably, the aqueous feed continues until the mineral acids are detected in the effluent stream. This is the point at which, if the feed was continued, a significant concentration of mineral acid would exit the resin bed. The amount of feed that can be added prior to mineral acid leakage can be determined by bed overload experiments familiar to those skilled in the art and shown in Examples 1 and 2. In a non-limiting example, the aqueous sugar stream is fed to one or more than one resin bed in the first anion exchange unit until the mineral acids are first detected in the effluent. The detection can be carried out by a direct measurement of the amount of mineral acid in the effluent or other indicators known to those of skill in the art, for example, conductivity, pH or other means. Once the mineral acids are detected, the feed is stopped. However, it should be appreciated that if the beds are arranged in series, the leaked acids would, in practice, be detected from the final bed in the series. The liquid held up in the bed is optionally removed by rinsing, draining, or blowing out. The resin bed(s) is then regenerated with a suitable regenerant, including, but not limited to, an aqueous regenerant, including, but not limited to an alkali, for example, ammonium hydroxide, sodium hydroxide, or potassium hydroxide. The feeding of the regenerant with alkali produces salts of the mineral acids and any of the remaining organic acids. For example, if sulfuric acid is present in the aqueous stream, a sulfate salt of ammonium, sodium, or potassium is produced after the addition of ammonium hydroxide, sodium hydroxide or potassium hydroxide, respectively. If a sulfate salt is produced, it may be collected and can be recovered, for example for use as fertilizer. Alternatively, the sulfate salt can be processed, for example by cation exchange, to produce sulfuric acid.

The present invention is not limited by the amount or number of regenerants applied to the first anion exchange unit. It will be understood by those of skill in the art that the resin may be regenerated with one or more regenerants introduced in one or more separate steps and that it may be advantageous to use the minimum amount of regenerant necessary to displace a desired amount of bound acid or anion. Accordingly, it is preferred to use aqueous solutions comprising acids or alkali as the regenerants since they produce more concentrated streams resulting from the regeneration.

The concentration of the regenerant is about 2 g/L to about 250 g/L, or any concentration range therebetween. In the case of bound sulfuric acid, when the regenerant is alkali, a high regenerant concentration produces concentrated sulfate salts. Thus, the choice of operating conditions may be selected to avoid precipitation of sulfate salts. More preferably, the regenerant concentration is about 10 g/L to about 150 g/L, or any concentration range therebetween.

Preferably, the regenerant is fed until the mineral acid is completely desorbed from the resin bed. The regenerant may be fed until more than about 80%, or, preferably, more than about 90% of the mineral acid is desorbed from the resin bed.

The regenerant can be fed to the column(s) in the same direction as the aqueous feed, known as a co-current regeneration. Alternatively, the regenerant may be fed counter-current, i.e., in the opposite direction to the aqueous feed. Following regeneration, the column(s) are optionally rinsed with water or other aqueous streams prior to resuming feed of the aqueous stream.

The stream with the lowest affinity for the resin, or effluent stream, comprising sugar and the organic acids is fed to the second anion exchange unit. This stream may optionally be concentrated by other means prior to feeding to the second unit. If evaporation is employed, then it should be carried out so that a substantial portion of the organic acids is carried forward. For example, it is preferred that at least about 70% of the organic acids, and more preferably greater than 70% of the acetic acid, present in the aqueous stream fed to the first stage are present in the second stage feed. Preferably, at least about 90% of the organic acids are fed to the second unit. More preferably, at least about 95% of the organic acids are fed to the second unit.

Although evaporation of the effluent from the first unit of the anion exchange falls within the scope of the invention, it is preferred that such an evaporation step is not carried out.

Preferably, at least about 90% of the sugars in the feed to the first unit pass through to the second unit. More preferably at least about 95%, or even more preferably about 98%, of the sugar passes through to the second unit.

Like the first anion exchange unit, the second anion exchange unit comprises a resin bed with an anion exchange resin. The first and the second anion exchange units may employ either a strong or a weak base anion exchange resin. For example, both anion exchange units may comprise strong base anion exchange resins or weak base anion exchange resins or either one of the two units may employ a strong base anion exchange resin with the other using a weak base anion exchange resin.

As the effluent stream from the first unit is fed to the second anion exchange unit, the organic acids bind to the resin while sugars and other organics which have a low affinity for the resin pass through the resin bed. Without wishing to be bound by theory, if a strong base anion exchange resin is used, the anion of the organic acid binds to the resin and if a weak base anion exchange resin is used, the organic acid binds to the resin. The sugar stream from the second anion exchange unit may be fed to fermentation or other processing. This stream may be optionally concentrated by membrane filtration or other methods known to those skilled in the art prior to fermentation or to further processing.

Preferably, the effluent stream from the first anion exchange unit is fed to the second anion exchange unit until the organic acids are detected in the effluent stream from the second unit. The detection can be carried out by a direct measurement of the amount of organic acid in the effluent or by other indicators known to those of skill in the art, for example, conductivity, pH or other means. The amount of feed that can be added prior to organic acid leakage is determined by bed overload experiments familiar to those skilled in the art and shown in Examples 1 and 2. Preferably, once the organic acids are detected, the feed is stopped. However, it should be appreciated that if the beds are arranged in series, the leaked acids would, in practice, be detected from the final bed in the series. If the beds are arranged in parallel, the leaked acids are typically detected in the effluent from each column. The liquid held up in the bed is optionally removed by rinsing, draining, or blowing out.

The resin bed is then regenerated with one or more suitable regenerants, which may be any aqueous regenerant, which may be water, to obtain a stream comprising the organic acid, the organic salt, or a combination thereof. If the regenerant is alkali, it is preferably ammonium hydroxide, sodium hydroxide, or potassium hydroxide. In the case of acetic acid, if ammonium hydroxide, sodium hydroxide or potassium hydroxide are used as regenerants, their respective acetate salts are produced, namely ammonium acetate, sodium acetate, or potassium acetate. The acetate salt is then recovered. The concentration of regenerant may be about 2 g/L to about 250 g/L, or any concentration range therebetween. More preferably, the regenerant concentration is about 10 g/L to about 150 g/L, or any concentration range therebetween.

Similar to the first anion exchange unit, the second anion exchange unit may be regenerated using more than one regenerant in separate steps. Although any regenerant may be utilized, it may be advantageous to use an aqueous solution comprising acid or alkali to minimize the amount of regenerant necessary to displace a desired amount of bound acid or anion.

In a non-limiting example, the regenerant is fed until the organic acid is completely or substantially desorbed from the resin bed. The regenerant may be fed until more than about 80% of the organic acid is desorbed from the resin bed, or, preferably, more than about 90% of the organic acid is desorbed from the resin bed.

If an acetate salt is produced during regeneration, this salt may be recovered or further processed. The salt may also be recovered as acetic acid. The acetic acid may be recovered from the acetate salt by distilling the acetate salt, preferably after adjustment of the pH to below about 4.0 with a nonvolatile acid such as sulfuric acid. In one embodiment, the pH is adjusted to below about 3.5, 3.0, 2.5, 2.0 or 1.5 with a non-volatile acid. Alternatively, the acetic acid may be recovered from the acetate salt solution by liquid-liquid extraction or by stripping the acetic acid with air or steam.

The process of the invention may be carried out using a Simulated Moving Bed (SMB) system. By the term "SMB system", it is meant any continuous chromatographic technique which simulates a flow of a liquid mobile phase moving countercurrent to a flow of a solid stationary phase, i.e., the SMB system simulates movement of the resin bed in a direction opposite to that of the liquid flow. Typically, an SMB system comprises a set of fixed beds connected in a closed circuit with two or more inlet and two or more outlet streams. The simulated movement may be carried out by periodically shifting four or more flow locations by some fraction of the total bed. A description of the operation of an SMB system is provided in WO 2006/007691 (Foody and Tolan), to which the reader is directed for reference and which is incorporated herein by reference. Improved SMB ("ISMB") systems (available for example from Eurodia Industrie S.A., Wissous, France; Applexion S.A., Epone, France; or Amalgamated Research Inc., Twin Falls, Id.) may also be used in the practice of the invention.

Although the use of a two-unit anion exchange separation system has been described, the process of the invention may alternatively comprise carrying out the separation on a single anion exchange unit. Similar to using a two-unit system, this embodiment relies on the differential affinity of the sugar(s), the organic acid(s) and the mineral acid(s) for the anion exchange resin. The aqueous feed is passed through the resin bed and the sugars and most other inorganic and organic compounds pass through the resin bed. Since the organic acids or the anions of the organic acids have an intermediate level of affinity for the resin, they bind to the resin initially. The mineral acid or the anion of the mineral acid, which has the highest affinity for the resin of the major compounds present, bind to the resin, displacing the organic acids which subsequently bind to another region of the resin bed. Preferably the feed is passed through the single anion exchange unit until the organic acids are first detected in the product stream. This is the point at which, if the feeding was continued, a significant concentration of organic acid would exit the resin bed. The amount of feed that can be added prior to organic acid leakage can be determined by bed overload experiments familiar to those skilled in the art and as set forth in the examples. The liquid held up in the bed is optionally removed by rinsing, draining or blowing out.

After the resin bed is loaded with both the organic acid and the mineral acid (or anions of these acids), it is regenerated. Similar to the process employing two-anion exchange units, when using a single anion exchange unit, the regeneration is conducted to produce two separate outlet streams, one comprising the organic acid or salts thereof, and one comprising the mineral acid, or salts thereof. However, in this embodiment, both arise from the same anion exchange unit rather than separate units as described previously.

The product stream comprising the organic acid or its salts may be obtained by regenerating the resin bed(s) with an aqueous regenerant, which may be water. The aqueous regenerant preferentially desorbs the organic acids or anions of the organic acids. The liquid held up in the bed is then optionally removed by rinsing, draining or blowing out. The resin bed(s) of the anion exchange unit comprising the bound mineral acid or anion of the mineral acid is subsequently regenerated with additional aqueous regenerant, which may be water, to obtain an outlet stream comprising the mineral acid or the mineral salt.

The preferred conditions and process equipment employed for the separation on a single anion exchange unit are as described in connection with the anion exchange system utilizing two separate units. Similar to the two-unit process, it is preferred that the regenerant(s) is selected from acid or alkali in order to minimize the amount of regenerant necessary to displace a desired amount of bound acid or anion. Furthermore, it should be appreciated that a different regenerant may be used in each regeneration stage. For example, the resin may be regenerated with acid, followed by the addition of alkali. Alternatively, the same regenerant is used to obtain both the product stream(s) containing the organic acid, or a salt thereof, and the outlet stream(s) comprising the mineral acid, or a salt thereof. The resin bed is typically a vertical column, horizontal bed, or a combination thereof, filled with anion exchange resin.

Although the process involves obtaining both the product and outlet streams from a single anion exchange unit, the system may further comprise multiple units arranged in parallel, with each unit being loaded with the organic acid and mineral acid (or their anions) and each subsequently regenerated to obtain separate product and outlet streams. The invention may also be practiced with a single unit comprising more than one resin bed in series.

The present invention will be further illustrated in the following examples.

EXAMPLES

Example 1

Separation of Sulfuric Acid from a Xylose Stream Using the First Unit of a Two-Unit Anion Exchange System An aqueous stream comprising xylose, sulfuric acid and acetic acid was prepared from wheat straw by using a steam and sulfuric acid pretreatment as described by Foody (U.S. Pat. No. 4,461,648, which is incorporated herein by reference). The pretreated wheat straw washed with water and the resulting sugar stream comprised the components shown in Table 1. The stream had a pH of 1.2. The sugar stream also comprised other organic acids, hexoses and other pentose sugars. Sulfuric and acetic acid concentration was measured using a Dionex ICS-2500 HPLC equipped with Chromeleon® software (version 6.6), an IonPac® AS11-HC column (4×250 mm), an AG11-HC guard column (4×50 mm), a conductivity detector and an anion self-regenerating suppression ultra-II system (ASRS-Ultra II). The method used an isocratic 1 mM NaOH mobile phase from 1 to 15 minutes, a 1 to 60 mM NaOH gradient mobile phase from 15 to 21 minutes and finally an isocratic 60 mM NaOH mobile phase from 25 to 30 minutes. Xylose was measured using the above HPLC system using a CarboPac™ PA1 column (4×250 mm) and guard (4×50 mm) column with pulsed amperometric detection. The method used a 10 mM NaOH isocratic mobile phase for fourteen minutes, an isocratic, 250 mM NaOH mobile phase from 14.1 to 16.7 minutes followed by an isocratic 10 mM NaOH mobile phase from 16.8 to 20 minutes.

TABLE 1

Aqueous stream feed to first unit of a two-unit anion exchange system

| Component | Concentration (g/L) |
| --- | --- |
| Sulfuric acid | 12.5 |
| Acetic acid | 4.82 |
| Xylose | 33.8 |

This aqueous stream was fed to the first unit of an anion exchange system. This first unit comprised a weak base anion exchange resin, DOWEX MARATHON WBA, which comprised a tertiary amine functional group and a styrene-divinylbenzene macroporous matrix. The mean particle size of this resin is 525 microns. The resin was first prepared by soaking in 85% methanol for 15 minutes and then rinsing with water. This wetting procedure is not necessary after the first time the resin is used and is not required for all weak base anion exchange resins. One hundred millilitres (100 mL) of prepared resin was used in a d=1.2 cm glass column. The stream was fed at a rate of 5.0 mL/minute through the column and samples of 23 mL were collected at the column exit. The first stage weak base anion exchange column was run at ambient temperature.

The elution profiles of xylose, acetic acid and sulfuric acid from the column are shown in FIG. 1. The xylose eluted from the bed almost immediately after the void volume exited the column. The void volume liquid (38 mL) is present in the column at the start of the experiment and is pushed out by the feed. The acetic acid bound to the resin until a volume of feed corresponding to nearly four times the volume of the resin bed had passed through the column. Beyond this point, acetic acid was detected in the effluent at concentrations up to 1.4 times the feed concentration.

Sulfuric acid has the highest affinity for the resin and was not detected in the effluent until 5.9 bed volumes had been fed. The 1% breakthrough capacity (point at which the effluent has 1% of the original concentration of sulfuric acid in the feed stream) of the resin for sulfuric acid was calculated to be 0.75 equivalents of sulfuric acid/L of resin (Equation 1). Feeding continued to 8.7 bed volumes to obtain a sufficient elution profile for sulfuric acid. In the process of the invention, wherein the effluent is fed into a second unit, feeding would stop when sulfuric acid is detected. The point at which feeding is stopped may be greater than or less than the 1% breakthrough point. The theoretical capacity for the MARATHON WBA resin used is 1.3 equivalents/L of resin.

(5.9 bed volumes)(0.1 L bed volume)(12.5 g/L sulfuric acid)/(98 g/equivalent)(0.1 L resin)=0.75 equivalents/Liter.    Equation 1

After the feeding of 8.7 bed volumes of feed stream, the column was washed with one bed volume of water. The resin was then regenerated with 5 w/v % aqueous ammonia, which was fed at a rate of 5 mL/min. The amount of base used was 1.2 equivalents relative to the amount of sulfuric acid equivalents bound to the column. After feeding the base, water was used to wash the mineral salt off of the column. FIG. 2 shows the amount of sulfate obtained in g/L as a function of the fractional bed volume of combined liquid fed to the column. The bound sulfate was substantially removed from the column after 1.83 bed volumes of aqueous ammonia solution and wash water were fed. Table 2 indicates the concentration and yield of bound sulfate obtainable when sub-portions of the outlet streams are pooled. The pools are composed of the total volume collected between the indicated, initial (from fbv) and final (to fbv) outlet-stream fractional bed volume. The outlet streams contained sulfate (as ammonium sulfate) at higher concentrations than present (as sulfuric acid) in the original streams.

TABLE 2

Concentration and yield of sulfate in the outlet stream

| From fbv | To fbv | % Recovery | Concentration (g/L) |
|---|---|---|---|
| 1.4 | 1.5 | 32 | 50.2 |
| 0.66 | 1.5 | 91 | 26.4 |
| 0.66 | 1.83 | 97 | 20.2 |

Example 2

Separation of Acetic Acid from Xylose in the Second Unit of a Two-Unit Anion Exchange System An aqueous stream comprising xylose, sulfuric acid and acetic acid was produced from wheat straw by using a steam and sulfuric acid pretreatment as described by Foody in U.S. Pat. No. 4,461,648 and the pretreated wheat straw washed with water to produce a sugar stream which was then fed to a first unit of a two-unit anion exchange separation system as described in Example 1. The resulting aqueous sugar stream obtained from a pooled effluent of the first unit comprised the components reported in Table 3 below. The sugar stream also comprised other organic acids, hexoses and other pentose sugars. The pH of this stream was 3.5. This sugar stream was fed to the second unit of the two-unit system containing the same resin as in Example 1. This column had a bed volume of 50 mL and a diameter of 1.2 centimeters. The second weak base anion exchange column was run at ambient temperature.

TABLE 3

Feed to the second unit of a two-unit anion exchange system

| Component | Concentration (g/L) |
|---|---|
| Sulfuric acid | 0.23 |
| Acetic acid* | 6.57 |
| Xylose | 33.8 |

*Concentration is reported as acetic acid and corresponds to the total concentration of acetic acid and acetate in the feed.

The elution profile from the second unit of the anion exchange system is shown in FIG. 3. The acetic acid bound to the column and the 1% breakthrough for acetic acid was reached when approximately 5.9 bed volumes of the sugar stream was fed. The effluent from the column up to 5.9 bed volume comprised xylose and was substantially free of acetic acid. The 1% breakthrough capacity of the resin for acetic acid was calculated to be 0.65 equivalents of acetic acid per litre of resin (Equation 2). Typically in the process of the invention, if the product stream from the second unit comprising sugars were being collected or further processed, feeding to the column would stop at the first detection of acetic acid in the effluent stream. The point at which feeding is stopped can be greater than or less than the 1% breakthrough point. The theoretical capacity for the Marathon WBA resin used is 1.3 equivalents/L of resin.

(6.57 g/L acetic acid)(5.9 bed volumes)(0.05 L/bed volume)/(60 g/equivalent)(0.05 L bed volume)=0.65 equiv/L resin.    Equation 2

The resin was regenerated with 5% w/v aqueous ammonia which was added at a rate of 5 mL/min. The amount of base used was 1.2 equivalents relative to the amount of acetic acid equivalents bound to the column. After feeding the base, water was used to wash the salt off the column. FIG. 4 shows the amount of acetate obtained in g/L as a function of the fractional bed volume of combined liquid fed to the column. The acetate was substantially removed from the column after 1.9 bed volumes of ammonium hydroxide solution and wash water were fed. Table 4 indicates the concentration and yields of acetate obtainable when sub-portions of the outlet stream are pooled. The regeneration streams contained acetate (as ammonium acetate) at higher concentrations than the combined concentration of acetic acid and acetate in the original streams.

TABLE 4

Concentration and yield of acetate in the outlet stream

| From fbv | To fbv | % Recovery | Concentration (g/L) |
|---|---|---|---|
| 0.7 | 1.0 | 46.6 | 45.9 |
| 0.4 | 1.4 | 91.7 | 29.1 |
| 0.4 | 1.7 | 96.9 | 23.1 |

Example 3

Separation of Sulfuric Acid and Acetic Acid from Xylose in a Two-Unit Anion Exchange System An aqueous sugar stream comprising xylose, sulfuric acid and acetic acid was made from wheat straw by using a steam and sulfuric acid pretreatment as described by Foody (U.S. Pat. No. 4,461,648, which is incorporated herein by reference). The pretreated wheat straw washed with water and the resulting sugar stream comprised the components shown in Table 5. The sugar stream also comprised other organic acids, hexoses and other pentose sugars. The stream had a pH of 1.2.

TABLE 5

Feed to a two-unit anion exchange system

| Component | Concentration (g/L) |
|---|---|
| Sulfuric acid | 18.62 |
| Acetic acid | 9.81 |
| Xylose | 50.25 |

The stream was fed to the first unit of a two-unit anion exchange system prepared as described in Example 1. The effluent from the first unit was allowed to feed directly onto the second unit without first collecting in fractions or pooling the effluent from the first unit. The second unit was prepared as described in Example 2. The stream was fed at a rate of 5.0 mL/minute through the columns and samples of 10-13 mL were collected at the second column exit. Small aliquots were removed from the first column effluent to monitor conductivity and pH and to measure xylose, acetic and sulfuric acid. The results of the first column effluent monitoring are shown in FIG. 5. Conductivity rose to around 1000 μS when acetic acid entered the effluent stream then rose again when sulfuric acid began to enter the effluent stream. The pH decreased as acetic acid entered the effluent stream and then decreased further when sulfuric acid began to enter the effluent stream. Feeding continued until the second conductivity increase was detected. This took place after 3.28 bed volumes of feed had passed through the first column. After the two-unit anion exchange system, the sugar stream was substantially free of sulfuric and acetic acid. The fractions collected from the second column effluent comprised xylose, acetic and sulfuric acid as provided in Table 6. Where indicated, (<0.05) the acids could not be detected above the limit of detection using the HPLC procedure described above.

TABLE 6

Composition of fractions from the second column

| Fractional bed volume (L of feed/L of resin bed) | Xylose (g/L) | Acetic acid (g/L) | Sulfuric acid (g/L) |
|---|---|---|---|
| 2.17 | 50.54 | <0.05 | <0.05 |
| 3.93 | 51.53 | <0.05 | <0.05 |
| 5.44 | 51.60 | 0.01 | <0.05 |

After the feeding of 3.28 bed volumes of feed stream (based on first column), the columns were separated and washed with one bed volume of water. Each column was then regenerated with 7% w/v aqueous ammonia, which was fed at a rate of 5 mL/min. FIG. 6 shows that the majority (>97%) of bound acetic acid can be recovered from the second column as ammonium acetate when 2.6 excess equivalents of aqueous ammonia are used (excess equivalents are calculated by dividing the number of equivalents of used aqueous ammonia by the theoretical capacity of the resin (capacity=1.3 equivalents/L of resin for MARATHON WBA)). The majority (>97%) of bound sulfuric acid can be recovered from the first column as ammonium sulfate when 3.0 excess equivalents of aqueous ammonia are used.

Example 4

Regeneration of Bound Acetic Acid with Aqueous Regenerants

An aqueous stream comprising acetic acid was prepared by diluting glacial acetic acid in deionized water. The aqueous stream comprised 11.64 g/L acetic acid. The aqueous stream was fed to a resin bed comprising the weak base anion exchange resin, Purolite® A103S. Purolite® A103S comprises a tertiary amine functional group and a stryrene-divinylbenzene macroporous polymer matrix. The typical particle size of this resin is 650-900 microns. One hundred millilitres (100 mL) of prepared resin was used in a d=1.2 cm glass column. The resin was first prepared by soaking in 85% methanol for 15 minutes, rinsing with water, conditioning with three bed volumes of a 7% w/v aqueous ammonia followed by a rinsing with water. Pre-washing with ammonia or a stronger base such as sodium hydroxide ensures that all tertiary amine functional groups in a weak base resin are available to bind acids and removes the small proportion of anions that can be bound to weak base anion exchange resins on functional groups other than the major tertiary amine group functionality.

The aqueous stream comprising acetic acid was fed at a rate of 5.0 mL/minute until just prior to acetic 1% breakthrough (1.21 eq/L of resin). The 1% breakthrough capacity of this resin for acetic acid had been previously measured to be about 1.24 eq/L. The liquid held up in the resin bed was removed by rinsing with de-ionized water. In this example, one bed volume of wash water was used. Following the rinsing, a separate 11.5 wt % sulfuric acid solution was used to desorb the bound acetic acid from the resin bed. The product stream comprising acetic acid was collected in fractions for analysis. FIG. 7 shows the amount of acetic acid obtained in g/L as a function of the fractional bed volume of combined regeneration liquid fed to the column. Table 7 indicates the concentration and yields of bound acetic acid obtainable when sub-portions of the outlet stream are pooled. The product stream contained acetic acid at higher concentrations than in the original feed stream. The resin-bound mineral acid can be displaced using an additional aqueous regenerant such as, for example, aqueous ammonia as outlined in Example 1 and 3.

TABLE 7

Concentration and yield of acetic acid in the outlet stream

| From fbv | To fbv | Volume (mL) | % Recovery | Concentration (g/L) |
|---|---|---|---|---|
| 0.86 | 2.11 | 124.3 | 79.9 | 81.9 |
| 0.51 | 2.11 | 160.1 | 91.0 | 93.3 |
| 0.0 | 2.11 | 210.8 | 32.7 | 97.1 |

Example 5

Separation of Sulfuric Acid and Acetic Acid in a Single Anion Exchange Unit

An aqueous stream comprising xylose, sulfuric acid, and acetic acid was made from pure chemicals by dissolving the chemicals in deionized water.

TABLE 8

Feed to a single anion exchange unit

| Component | Concentration (g/L) |
|---|---|
| Sulfuric acid | 7.56 |
| Acetic acid | 8.27 |
| Xylose | 47.7 |

The aqueous stream was fed to a resin bed comprising the weak base anion exchange resin Dowex Marathon WBA. One hundred millilitres (100 mL) of prepared resin was used in a d=1.2 cm glass column. The resin was first prepared by treatment with 5-10 bed volumes of 7% w/v aqueous ammonia followed by rinsing with water.

The aqueous stream was fed at a rate of 6-7 mL/minute until just prior to acetic 1% breakthrough (1.03 eq/L of resin). The liquid held up in the resin bed was removed by rinsing with de-ionized water. In this example, one bed volume of wash water was used. Following the rinsing, a separate 9.1 mL pulse of 7% aqueous ammonia was added to the top of the bed followed by a "water push" that was followed by one bed volume of water wash through the column. This amount of aqueous ammonia was sufficient to completely release acetic acid and insufficient for complete release of sulfuric acid. An additional bed volume of water was added after this to ensure all of the liquid held up in the bed during the regeneration step had eluted. Finally, a second regeneration step was performed using one full bed volume of 7% aqueous ammonia. This excess amount of aqueous ammonia was sufficient for complete release of sulfuric acid. The resin effluent during all of the feeding, washing, and regeneration steps was collected in fractions for analysis. These fractions were analyzed for sulfate, ammonium, acetate, and/or xylose content.

The elution profile for xylose is shown in FIG. 8A. The xylose eluted from the bed almost immediately after the void volume exited the column and elutes at about its feed concentration between about 2 and 5 fractional bed volumes. Shortly after the feeding is stopped, any residual xylose is completely removed from the bed with the first water wash.

The regeneration profiles for acetic acid and sulfuric acid are shown in FIG. 8B. Shortly after the first ammonia aliquot is fed to the column, acetate and ammonium elute from the column at the same time, starting at about 6.5 bed volumes. This indicates the formation of ammonium acetate, which can be collected in discrete fractions. All of the ammonium acetate is collected during the water push. The ammonium and acetate elute in about a 1:1 molar ratio, which confirms the formation of ammonium acetate. Very little sulfuric acid is removed from the column during the first regeneration step.

Shortly after the bed is regenerated a second time with aqueous ammonia, sulfate and ammonium elute from the column at the same time, starting at about 8.5 bed volumes. This indicates the formation of ammonium sulfate, which can be collected in discrete fractions. All of the sulfate can be collected during this second regeneration step as ammonium sulfate. The ammonium and sulfate elute in about a 2:1 molar ratio, which confirms the formation of ammonium sulfate.

Example 6

Separation of Acetic Acid from Xylose in the Second Unit of a Two-Unit Anion Exchange System Comprising a Strong Base Anion Exchange Resin An aqueous stream comprising xylose and acetic acid was prepared from pure chemicals by dissolving the chemicals in deionized water (Table 9).

TABLE 9

Feed to the second unit of a two-unit anion exchange system

| Component | Concentration (g/L) |
|---|---|
| Acetic acid | 6.6 |
| Xylose | 49.48 |

The aqueous stream was fed to the second unit of an anion exchange system comprising the strong base anion exchange resin LEWATIT MonoPlus™ MP500. This resin comprises a quaternary amine functional group and a styrene-divinylbenzene macroporous matrix. The mean particle size of the resin is 600 microns. One hundred millilitres (100 mL) of prepared resin was used in a d=1.2 cm glass column. The resin was first prepared by rinsing with water and conditioning with 2 L of a 8.3 wt % sodium hydroxide at 5 mL/min to ensure that all the quaternary amine functional groups were in the hydroxide form. The resin is supplied from the manufacturer in the Cl⁻ form.

The aqueous stream was fed at a rate of 5 mL/min until the column was fully saturated with acetate ion. This occurred at 0.99 eq/L of resin. FIG. 9 shows the elution profile for xylose and acetic acid. The 1% breakthrough of xylose occurs after only 2 fractional bed volumes and xylose elutes at approximately feed concentration after only 3 fractional bed volumes. Between 3 and 8.33 fractional bed volumes, xylose elutes while acetate ion is held back by the resin. The acetic acid 1% breakthrough occurs after 8.33 fractional bed volumes (0.89 eq/L of resin) of the aqueous stream have been fed.

A second column comprising 100 mL of LEWATIT Mono-Plus™ MP500 resin was prepared as described above in Example 6. The aqueous feed stream described above in Table 9 was fed to the column until the 1% acetic acid breakthrough point. The liquid held up in the resin bed was removed by rinsing with de-ionized water. In this example, two bed volumes of water was used. Following the rinsing, a separate 8.3 wt % sodium hydroxide solution was used to recover the bound acetate from the column. The outlet stream comprising acetate was collected in fractions for analysis. FIG. 10 shows the amount of xylose and acetate obtained in g/L as a function of the fractional bed volume of combined rinse and regeneration liquid fed to the column. In the initial water rinse the void liquid (first ~38 mL or 0.38 fbv) contains some xylose that is un-retained. A small amount (~14%) of very weakly bound xylose elutes with the first 1.2 fbv of rinse water that is fed through the column. Table 10 indicates the concentration and yields of bound acetate obtainable when sub-portions of the outlet stream are pooled. The outlet stream contained acetate at higher concentrations than in the original feed stream.

TABLE 10

Concentration and yield of acetate in the outlet stream from unit 2 of an anion exchange system comprising a strong base anion exchange resin

| From fbv | To fbv | Volume (mL) | % Recovery | Concentration (g/L) |
|---|---|---|---|---|
| 2.08 | 4.33 | 225 | 99.9 | 24.62 |
| 2.25 | 4.15 | 190 | 97.2 | 28.8 |
| 2.25 | 3.61 | 136 | 90.4 | 36.9 |

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A process for obtaining one or more than one organic salt or organic acid from an aqueous sugar stream comprising one or more than one mineral acid, one or more than one organic acid, and a sugar selected from the group consisting of xylose, glucose, arabinose, galactose, mannose and a combination thereof, said process comprising:
   (i) introducing the aqueous sugar stream to a first anion exchange unit comprising one or more than one bed comprising an anion exchange resin, wherein the mineral acid, an anion of the mineral acid, or a combination thereof, binds to the resin;
   (ii) producing an effluent stream comprising the sugar and the organic acid from the first anion exchange unit and regenerating the anion exchange resin with one or more regenerants, thereby producing one or more outlet streams comprising the mineral acid, a salt of the mineral acid or a combination thereof;
   (iii) feeding the effluent stream comprising the sugar and the organic acid to a second anion exchange unit comprising one or more than one bed comprising an anion exchange resin, wherein the organic acid or an anion of the organic acid binds to the resin;
   (iv) obtaining a stream from the second anion exchange unit comprising the sugar, which stream is substantially free of the mineral acid and the organic acid and regenerating the second anion exchange unit with one or more regenerants, thereby producing one or more product streams comprising a salt of the organic acid, the organic acid or a combination thereof; and
   (v) recovering the one or more product streams, wherein the organic acid is selected from the group consisting of acetic acid, formic acid, glucuronic acid, galacturonic acid and a combination thereof and the mineral acid is selected from the group consisting of sulfuric acid, hydrochloric acid, sulfurous acid, phosphoric acid and a combination thereof.

2. The process according to claim 1, further comprising a step of recovering the mineral acid, the salt of the mineral acid or a combination thereof.

3. The process according to claim 1, wherein, in the step of feeding (step (iii)), at least about 70% of the organic acid present in the aqueous sugar stream is fed to the second anion exchange unit.

4. The process according to claim 1, wherein the anion exchange resin in the first anion exchange unit, the second anion exchange unit or both the first and the second anion exchange unit comprises a weak base anion exchange resin.

5. The process according to claim 4, wherein the anion exchange resin in both the first and the second anion exchange unit comprises a weak base anion exchange resin.

6. The process according to claim 1, wherein the anion exchange resin in the first anion exchange unit, the second anion exchange unit or both the first and the second anion exchange unit comprises a strong base anion exchange resin.

7. The process according to claim 1, wherein the mineral acid is sulfuric acid.

8. The process according to claim 1, wherein the organic acid is acetic acid.

9. The process according to claim 1, wherein the one or more regenerants in step (ii), step (iv) or both step (ii) and step (iv) is an alkali solution selected from the group consisting of an ammonium hydroxide solution, a sodium hydroxide solution and a potassium hydroxide solution.

10. The process according to claim 9, wherein the alkali solution is an ammonium hydroxide solution.

11. The process according to claim 1, wherein the first anion exchange unit, the second anion exchange unit or both the first anion exchange unit and the second anion exchange unit is a Simulated Moving Bed (SMB) system or an Improved Simulated Moving Bed (ISMB) system.

12. The process according to claim 1, wherein the organic acid is acetic acid and further comprising recovering the acetic acid from the one or more product streams by distillation.

13. The process according to claim 1, wherein the organic acid is acetic acid and further comprising recovering the acetic acid from the one or more product streams by liquid-liquid extraction.

14. The process according to claim 1, wherein the organic acid is acetic acid and further comprising recovering the acetic acid from the one or more product streams by stripping the acetic acid with air or steam.

15. The process according to claim 12, 13 or 14, wherein the one or more product streams comprise a salt of acetic acid and further comprising adjusting the pH of the one or more product streams to about 4 or lower by the addition of a second acid prior to recovering the acetic acid.

16. The process according to claim 1, wherein the aqueous sugar stream is at a pH of about 0.4 to about 5.0.

17. The process according to claim 1, wherein the aqueous sugar stream is obtained by pretreating a lignocellulosic feedstock at a pH of about 0.4 to about 5.0 by adding one or more than one acid to the lignocellulosic feedstock to hydrolyze at least a portion of the hemicellulose in the feedstock.

18. The process according to claim 1, wherein the aqueous sugar stream is a hydrolyzate stream obtained from adding one or more than one acid to a lignocellulosic feedstock to hydrolyze both hemicellulose and cellulose present in said lignocellulosic feedstock to their respective sugar monomers.

19. The process according to claim 1, wherein one or more regenerants in either or both of step (ii) and (iv) is an aqueous solution independently selected from the group consisting of an alkali solution, an acid solution and water.

20. The process according to claim 19, wherein one or more regenerants in either or both step (ii) and (iv) is an aqueous solution independently selected from the group consisting of an alkali solution and an acid solution.

21. A process for obtaining an organic salt or organic acid from an aqueous sugar stream comprising a mineral acid, an organic acid, and a sugar selected from the group consisting of xylose, glucose, arabinose, galactose, mannose and a combination thereof, said process comprising the steps of:
  (i) introducing the aqueous sugar stream to a separation system comprising one or more beds of anion exchange resin and obtaining at least one stream therefrom comprising the sugar;
  (ii) regenerating the one or more beds of anion exchange resin in one or more stages, thereby producing at least one stream comprising the mineral acid, a salt of the mineral acid, or a combination thereof, and at least one separate product stream comprising the organic acid, a salt of the organic acid, or a combination thereof; and
  (iii) recovering the at least one product stream, wherein the organic acid is selected from the group consisting of acetic acid, formic acid, glucuronic acid, galacturonic acid and a combination thereof and the mineral acid is selected from the group consisting of sulfuric acid, hydrochloric acid, sulfurous acid, phosphoric acid and a combination thereof,
  wherein steps (i) and (ii) are carried out by anion exchange.

22. The process of claim 21, wherein the anion exchange system comprises a first and a second anion exchange unit.

23. The process of claim 22, wherein said step of introducing comprises feeding the aqueous sugar stream to the first anion exchange unit, wherein the mineral acid, an anion of the mineral acid, or a combination thereof, binds to the resin of the first anion exchange unit;
  said process further comprising obtaining an effluent stream comprising the sugar and the organic acid, a salt of the organic acid, or a combination thereof, from said first anion exchange unit and then feeding the effluent stream to the second anion exchange unit and said organic acid, an anion of the organic acid, or a combination thereof, binds to the resin of the second anion exchange unit; and wherein
  said step of regenerating comprises adding at least one regenerant to the first anion exchange unit to produce the at least one stream comprising the mineral acid, a salt of the mineral acid, or a combination thereof, and adding at least one regenerant to the second anion exchange unit to produce the at least one product stream comprising the organic acid, a salt of the organic acid, or a combination thereof.

24. The process of claim 23, wherein at least about 70% of the organic acid present in the aqueous sugar stream is fed to the second anion exchange unit.

25. The process of claim 21, wherein steps (i)-(iii) are carried out in a single anion exchange unit.

26. The process of claim 23, wherein in said step of introducing, the mineral acid, organic acid, or anions thereof, bind to the resin.

27. The process according to claim 21, further comprising a step of recovering the mineral acid, a salt of the mineral acid, or a combination thereof.

28. The process according to claim 21, wherein the separation system comprises a weak base anion exchange resin.

29. The process according to claim 21, wherein the separation system comprises a strong base anion exchange resin.

30. The process according to claim 21, wherein the mineral acid is sulfuric acid.

31. The process according to claim 21, wherein the organic acid is acetic acid.

32. The process according to claim 23, wherein the organic acid is acetic acid.

33. The process according to claim 21, wherein the regeneration comprises adding one or more regenerants to the one or more resin beds to regenerate the anion exchange resin, and the one or more regenerants is an aqueous solution selected from the group consisting of an alkali solution, an acid solution, water and a combination thereof.

34. The process according to claim 33, wherein the one or more regenerants is an aqueous solution selected from the group consisting of an alkali solution, an acid solution and a combination thereof.

35. The process according to claim 34, wherein the alkali solution is selected from the group consisting of an ammonium hydroxide solution, a sodium hydroxide solution, a potassium hydroxide solution, and a combination thereof.

36. The process according to claim 35, wherein the alkali solution is an ammonium hydroxide solution.

37. The process according to claim 21, wherein the separation system is a Simulated Moving Bed System or an Improved Simulated Moving Bed system.

38. The process according to claim 31, further comprising recovering the acetic acid from the at least one product stream by distillation.

39. The process according to claim 31, further comprising recovering the acetic acid from the at least one product stream by liquid-liquid extraction.

40. The process according to claim 31, further comprising recovering the acetic acid from the at least one product stream by stripping the acetic acid with air or steam.

41. The process according to claim 38, 39 or 40, wherein the at least one product stream comprises a salt of acetic acid and further comprising adjusting the pH of the at least one product stream to about 4 or lower by the addition of an acid prior to recovering the acetic acid.

42. The process according to claim 21, wherein the aqueous sugar stream is at a pH of about 0.4 to about 5.0.

43. The process according to claim 21, wherein the aqueous sugar stream is a hydrolyzate stream resulting from pretreating a lignocellulosic feedstock at a pH of about 0.4 to about 5.0, to hydrolyze at least a portion of hemicellulose present in the feedstock.

44. The process according to claim 21, wherein the aqueous sugar stream is a hydrolyzate stream resulting from adding an acid to a lignocellulosic feedstock, to hydrolyze both hemicellulose and cellulose present in said lignocellulosic feedstock to their respective sugar monomers.

45. A process for obtaining acetate salt, acetic acid or a combination thereof, from a lignocellulosic feedstock, comprising the steps of:
  (i) obtaining an aqueous sugar stream resulting from hydrolysis of the lignocellulosic feedstock, said hydrolysis comprising one or more stages of sulfuric acid addition, said sugar stream comprising acetic acid, acetate salt, or a combination thereof, sulfuric acid and one or more sugars selected from xylose, glucose, arabinose, galactose, mannose and a combination thereof;
  (ii) introducing the aqueous sugar stream to a Simulated Moving Bed separation system comprising one or more beds of anion exchange resin and obtaining at least one stream therefrom comprising the one or more sugars;
  (iii) regenerating the one or more beds of anion exchange resin with sulfuric acid, thereby producing at least one organic acid product stream comprising the acetic acid and, thereafter, regenerating the one or more beds of anion exchange resin with ammonium hydroxide to produce at least one separate outlet stream comprising ammonium sulfate; and (iv) recovering the at least one product stream.

46. The process according to claim 45, wherein the sulfuric acid addition is conducted to pretreat the lignocellulosic feedstock, thereby hydrolyzing at least a portion of hemicellulose present in said lignocellulosic feedstock to sugar monomers.

47. The process according to claim 45, wherein the sulfuric acid addition is conducted to hydrolyze both hemicellulose and cellulose present in said lignocellulosic feedstock to their respective sugar monomers.

* * * * *